US009006225B2

(12) United States Patent
Suzuki

(10) Patent No.: US 9,006,225 B2
(45) Date of Patent: Apr. 14, 2015

(54) STABLE PHARMACEUTICAL COMPOSITION

(75) Inventor: Kazumi Suzuki, Tokyo (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 697 days.

(21) Appl. No.: 12/355,143

(22) Filed: Jan. 16, 2009

(65) Prior Publication Data

US 2010/0041725 A1 Feb. 18, 2010

Related U.S. Application Data

(60) Provisional application No. 61/021,910, filed on Jan. 18, 2008.

(51) Int. Cl.
| | | |
|---|---|---|
| *A01N 43/00* | (2006.01) | |
| *A61K 31/33* | (2006.01) | |
| *C07C 27/00* | (2006.01) | |
| *A61K 31/196* | (2006.01) | |
| *A61K 9/20* | (2006.01) | |
| *A61K 31/404* | (2006.01) | |
| *A61K 31/416* | (2006.01) | |
| *A61K 31/4365* | (2006.01) | |
| *A61K 31/60* | (2006.01) | |
| *A61K 47/36* | (2006.01) | |
| *A61K 47/38* | (2006.01) | |

(52) U.S. Cl.
CPC ............. *A61K 31/196* (2013.01); *A61K 9/2018* (2013.01); *A61K 9/2027* (2013.01); *A61K 9/2054* (2013.01); *A61K 9/2059* (2013.01); *A61K 31/404* (2013.01); *A61K 31/416* (2013.01); *A61K 31/4365* (2013.01); *A61K 31/60* (2013.01); *A61K 47/36* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 2004/0044258 A1* | 3/2004 | Shoda et al. .................. 568/959 |
| 2004/0138180 A1 | 7/2004 | Ahmed et al. | |
| 2005/0032787 A1 | 2/2005 | Giannessi et al. | |
| 2006/0093631 A1 | 5/2006 | Buehler | |
| 2007/0213333 A1 | 9/2007 | Shoda et al. | |
| 2008/0070967 A1 | 3/2008 | Arimoto et al. | |

FOREIGN PATENT DOCUMENTS

| | | |
|---|---|---|
| AU | 2007274477 B2 | 1/2008 |
| EP | 1 477 472 A1 | 11/2004 |
| EP | 0 879 048 B2 | 7/2009 |
| JP | 10-505591 A | 6/1998 |
| JP | 2000-505801 A | 5/2000 |
| JP | 2004-513093 A | 4/2004 |
| MX | 2009000448 A | 1/2009 |
| WO | WO-96/05809 A1 | 2/1996 |
| WO | WO-97/28788 A1 | 8/1997 |
| WO | WO-02/32402 A1 | 4/2002 |
| WO | WO-03/070686 A1 | 8/2003 |
| WO | WO-2005/016862 A1 | 2/2005 |
| WO | WO-2008/010448 A1 | 1/2008 |

OTHER PUBLICATIONS

Chowhan et al. (Journal of Pharmaceutical Sciences, vol. 71, No. 12, pp. 1371-1375; Dec. 1982).*
FMC BioPolymer [Retrieved on Jan. 13, 2012 from the Internet: <URL: http://www.fmcbiopolymer.com/Portals/Pharm/Content/Docs/avicelrcclmsds.pdf].*
"Handbook of Pharmaceutical Excipients", fifth edition, 2007, excerpts include: (Fructose) pp. 193-196 with an English translation thereof, (Dextrose) pp. 596-599 with an English translation thereof, (Lactose, Monohydrate) pp. 650-658 with an English translation thereof. (Maltose) pp. 926-928 with an English translation thereof.
Japanese Office Action for Japanese Application No. 2009-550051 dated Feb. 19, 2013 with partial English translation.
Korean Office Action dated Jun. 10, 2012, for Korean Application No. 10-2010-7015203.
Australian Office Action, dated Aug. 22, 2011, for Australian Application No. 2009205073.
Beacham et al., "Some Observations on the Browning Reaction", Journal of Food Science, vol. 16, Issue 1-6, pp. 439-445, 1951, XP-002669516.
Byrn et al., "Chemical reactivity in solid-state pharmaceuticals: formulation implications", Advanced Drug Delivery Reviews, vol. 48, pp. 115-136, 2001, XP-002628347.
Canadian Office Action, dated Mar. 14, 2012, for Canadian Application No. 2,712,170.
Chinese Office Action, dated Feb. 14, 2012, for Chinese Application No. 200980102378.X.
Crowley et al., "Drug-Excipient Interactions", Pharmaceutical Technology Europe, Mar. 2001 (Article Reprinted, 6 pages).
DiFeo, "Drug Product Development: A Technical Review of Chemistry, Manufacturing, and Controls Information for the Support of Pharmaceutical Compound Licensing Activities", Drug Development and Industrial Pharmacy, vol. 29, No. 9, pp. 939-958, 2003, XP-002669515.

(Continued)

*Primary Examiner* — Jeffrey S. Lundgren
*Assistant Examiner* — Tori M Strong
(74) *Attorney, Agent, or Firm* — Birch, Stewart, Kolasch & Birch, LLP

(57) ABSTRACT

A pharmaceutical composition which includes a compound represented by the general formula (I):

(I)

$$Rs\diagdown C^5{=}C^6\diagdown$$
$$C^4\,(E)\!\!-\!\!Link\text{-}COOY$$
$$AR\diagup C^3{-}C^2\diagup$$

or a salt thereof, and a pharmaceutically acceptable carrier, wherein the composition does not substantially contain a reducing sugar and/or a carrier containing a reducing sugar as an ingredient as the pharmaceutically acceptable carrier, or when the composition contains a reducing sugar and/or a carrier containing a reducing sugar as an ingredient as the pharmaceutically acceptable carrier, contact of the reducing sugar and the compound represented by the general formula (I) or a salt thereof is eliminated.

4 Claims, 5 Drawing Sheets

(56) References Cited

OTHER PUBLICATIONS

Extended European Search Report, dated Apr. 2, 2012, for European Application No. 09702201.6.

Fraser-Reid et al., "Glycoscience: chemistry and chemical biology", Springer-Verlag Berlin Heidelberg, pp. 396-397, 2001.

Hodge, "Chemistry of Browning Reactions in Model Systems", Agricultural and Food Chemistry, vol. 1, No. 15, pp. 928-943, Oct. 14, 1953.

Chinese Office Action for Chinese Application No. 200980102378.X dated Aug. 20, 2012 with English translation.

Mexican Office Action for Mexican Application No. MX/a/2010/007632, dated Aug. 13, 2013, with a partial English translation.

Canadian Office Action dated Oct. 3, 2012 for Canadian Application No. 2,712,170.

"Biochemical Dictionary" (Second Edition, page 1325 with an English translation thereof, Edited by Kazutomo Imabori et al.) was published on Nov. 22, 1990 by Tokyo Kagaku Dojin, Japan.

"Chemical Dictionary", (First Edition, Edited by Michinori Ohki et al.), English translation of an excerpt from page 1413 was published on Oct. 1, 1994 by Tokyo Kagaku Dojin, Japan.

European Office Action for European Application No. 09702201.6 dated Dec. 12, 2013.

Ghugare et al., "Solid state investigation and characterization of the polymorphic and pseudopolymorphic forms of indapamide", Journal of Pharmaceutical and Biomedical Analysis, vol. 51, 2010, pp. 532-540.

Korean Office Action for corresponding Application No. 10-2010-7015203 dated Dec. 27, 2012 (with English translation).

Japanese Office Action, dated Dec. 4, 2012, for Japanese Application No. 2009-550051, along with an English translation.

Canadian Office Action for corresponding Application No. 2,712,170 dated Jun. 21, 2013.

Chinese Office Action and Search Report, dated Apr. 11, 2014, for Chinese Application No. 201310052266.6 with an English translation.

Japanese Office Action, dated May 20, 2014, for Japanese Application No. 2013-101787 with an English translation.

Mexican Office Action, dated Mar. 28, 2014, for Mexican Application No. MX/a/2010/007632 with an English translation.

Second Office Action issued Dec. 9, 2014, in Chinese Patent Application No. 201310052266.6, with English translation.

\* cited by examiner

STABLE PHARMACEUTICAL COMPOSITION

This Non-provisional application claims priority under 35 U.S.C. §119(e) on U.S. Provisional Application No. 61/021,910 filed on Jan. 18, 2008, the entire contents of which is hereby incorporated by reference into the present application.

TECHNICAL FIELD

The present invention relates to a stable pharmaceutical composition comprising a compound represented by the following general formula (I) or a salt thereof as an active ingredient.

BACKGROUND ART

The compounds represented by the following general formula (I) and salts thereof have prostaglandin and leukotriene production-suppressing action, and are known as medicaments extremely useful for therapeutic and/or prophylactic treatment of various diseases resulting from the lipid mediators, for example, inflammatory diseases, autoimmune diseases, allergic diseases, pain, and the like. Methods for producing the compounds represented by the general formula (I) or salts thereof are also reported in detail (Patent documents 1 and 2). However, sufficient information of pharmaceutical compositions containing a compound represented by aforementioned general formula (I) or a salt thereof is not disclosed in the aforementioned publications.

Patent document 1: International Patent Publication WO03/070686
Patent document 2: International Patent Publication WO2005/016862

DISCLOSURE OF THE INVENTION

Object to be Achieved by the Invention

The inventors of the present invention prepared pharmaceutical compositions comprising a compound represented by the aforementioned general formula (I) or a salt thereof as an active ingredient, and examined stability thereof. In the examination, they found that a novel problem that when a pharmaceutical composition comprising a compound represented by the aforementioned general formula (I) or a salt thereof was prepared by using a pharmaceutically acceptable carrier, decomposition or coloring of the active ingredient occurred depending on a type of a carrier, and poor stability was observed as a pharmaceutical composition. The aforementioned problem has not been reported so far.

Therefore, an object of the present invention is to provide a stable pharmaceutical composition comprising a compound represented by the aforementioned general formula (I) or a salt thereof as an active ingredient, a method for preparing thereof, and a method for stabilizing a pharmaceutical composition comprising a compound represented by the aforementioned general formula (I) or a salt thereof as an active ingredient.

Means for Achieving the Object

The inventors of the present invention conducted various researches to solve the aforementioned novel problem, and as a result, they found that generation of decomposition products or coloring of the compounds represented by the general formula (I) and salts thereof occurred when they were brought into contact with a reducing sugar among pharmaceutically acceptable carriers, and when a pharmaceutical composition was prepared without using reducing sugar, or alternatively when a pharmaceutical composition was prepared so that a compound represented by the general formula (I) or a salt thereof and a reducing sugar should not be contacted with each other in case that a reducing sugar was used, the decomposition or coloring of the active ingredient was successfully reduced or eliminated, and a stable pharmaceutical composition was successfully provided. The present invention was accomplished on the basis of the above finding.

The present invention thus includes the followings.
[A1] A pharmaceutical composition comprising a compound represented by the general formula (I):

[Formula 1]

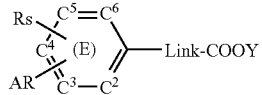

(I)

[In the formula, Link represents a saturated or unsaturated straight hydrocarbon chain having 1 to 3 carbon atoms.

$C^2$, $C^3$, $C^4$, $C^5$, and $C^6$ in the aromatic ring (E) independently represent a ring-constituting carbon atom. One of the ring-constituting carbon atoms to which Rs and AR do not bind represents a carbon atom substituted with amino group.

Rs represents -D-Rx or —N(Ry)(Rz).

D represents a single bond, oxygen atom, sulfur atom, —S(O)—, —S(O)$_2$—, or —C(O)—.

Rx represents a linear or branched saturated alkyl group having 3 to 8 carbon atoms, or represents Ra represented by the following formula:

$$R^1(CH_2)_k—$$ (Ra)

Rb represented by the following formula:

[Formula 2]

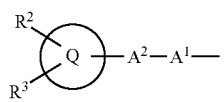

(Rb)

or Rc represented by the following formula:

[Formula 3]

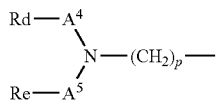

(Rc)

k in Ra represents 0 or an integer of 1 to 3. $R^1$ represents a saturated cyclic alkyl group having 3 to 7 carbon atoms, or a condensed saturated cyclic alkyl group having 6 to 8 carbon atoms, and $R^1$ may be substituted with one of lower alkyl group having 1 to 4 carbon atoms or two or more of the same or different lower alkyl groups having 1 to 4 carbon atoms. Q in Rb represents a partially unsaturated or completely unsaturated monocyclic or condensed bicyclic carbon ring or a heterocyclic ring (q), and binds to $A^2$ at an arbitrary position on the ring. The heterocyclic ring (q) contains the same or different 1 to 4 ring-constituting heteroatoms selected from the group consisting of nitrogen atom, oxygen atom, and sulfur atom. $A^1$ represents a single bond or an alkylene (a) having 1 to 3 carbon atoms, and the alkylene (a) may be substituted with a lower alkyl group having 1 to 4 carbon atoms or phenyl group. A2 represents a single bond, oxygen atom, sulfur atom, —S(O)—, —S(O)$_2$—, or —N(R$^4$)— (provided that when $A^2$ represents oxygen atom, sulfur atom, —S(O)—, —S(O)$_2$— or —N(R$^4$)—, $A^1$ represents ethylene or trimethylene). $R^2$ and $R^3$ independently represent hydrogen atom, a linear or branched saturated alkyl group having 1 to 4 carbon atoms, oxo group, thioxo group, fluorine atom, chlorine atom, bromine atom, trifluoromethyl group, —OR$^5$, —N(R$^6$)(R$^{6'}$), —NHCOR$^7$, —NHSO$_2$R$^8$, or -A$^6$-Qa, or they bind to each other to represent methylenedioxy group. $A^6$ represents a single bond or methylene. Qa represents a partially unsaturated or completely unsaturated monocyclic or condensed bicyclic carbon ring or a heterocyclic ring (qa), binds to $A^6$ at an arbitrary position on the ring, and may be substituted with one of $T^1$ or two or more of the same or different $T^1$. $T^1$ represents a linear or branched saturated alkyl group having 1 to 4 carbon atoms, hydroxyl group, fluorine atom, chlorine atom, bromine atom, trifluoromethyl group, nitro group, an alkoxy group having 1 to 4 carbon atoms, or a mono- or dialkylamino group having 1 to 4 carbon atoms. The heterocyclic ring (qa) contains the same or different 1 to 4 ring-constituting heteroatoms selected from the group consisting of nitrogen atom, oxygen atom, and sulfur atom. $R^4$ and $R^6$ independently represent hydrogen atom or a lower alkyl group having 1 to 4 carbon atoms. $R^5$ and $R^7$ independently represent hydrogen atom, a lower alkyl group having 1 to 4 carbon atoms, or -A$^6$-Qa. $R^8$ represents a lower alkyl group having 1 to 4 carbon atoms. $R^{6'}$ has the same meaning as $R^6$, or binds to $R^6$ to form a 3- to 6-membered ring together with the nitrogen atom to which they bind to represent a saturated nitrogen-containing cycloalkyl group or morpholino group. p in Rc represents an integer of 2 to 4. $A^4$ represents a single bond, methylene, or ethylene. $A^5$ represents —C(O)—, —C(S)—, or —S(O)$_2$—. Rd represents hydrogen atom, an alkyl group having 1 to 8 carbon atoms, or Qa. Re represents an alkyl group having 1 to 8 carbon atoms, -A$^6$-Qa, —(CH$_2$)$_i$R$^{14}$, —OR$^{28}$, —SR$^{28}$, or —N(R$^{29}$)(R$^{30}$). i represents an integer of 1 to 3, R$^{14}$ represents hydroxyl group, an alkoxy group having 1 to 4 carbon atoms, carboxyl group, or an N,N-dialkylcarbamoyl group having 1 to 4 carbon atoms. R$^{28}$ represents an alkyl group having 1 to 8 carbon atoms, or -A$^6$-Qa. R$^{29}$ represents an alkyl group having 1 to 8 carbon atoms, an alkoxycarbonyl group having 1 to 4 carbon atoms, or -A$^6$-Qa. R$^{30}$ represents hydrogen atom or a lower alkyl group having 1 to 4 carbon atoms, or binds to R$^{29}$ to form a 3- to 6-membered ring together with the nitrogen atom to which they bind to represent a saturated nitrogen-containing cycloalkyl group or morpholino group.

Rz has the same meaning as Rx, or Rz represents methyl group, ethyl group, or -A$^5$-Re. Ry represents hydrogen atom, an alkyl group having 1 to 8 carbon atoms, or -A$^6$-Qp, or Ry may bind to Rz to form, together with a nitrogen atom to which they bind, a saturated or unsaturated nitrogen-containing cyclic substituent having 3 to 7 atoms, wherein said nitrogen-containing cyclic substituent may optionally be substituted with one or two lower alkyl groups having 1 to 4 carbon atoms wherein said two alkyl groups may be the same or different. Qp represents phenyl group, and this phenyl group may be substituted with one of $T^1$ or two or more of the same or different $T^1$.

AR represents a partially unsaturated or completely unsaturated condensed bicyclic carbon ring or a heterocyclic ring (ar), and may be substituted with one of Xa or two or more of the same or different Xa. The heterocyclic ring (ar) contains the same or different 1 to 4 ring-constituting heteroatoms selected from the group consisting of nitrogen atom, oxygen atom, and sulfur atom. Xa represents a linear or branched saturated alkyl group having 1 to 4 carbon atoms, a saturated cyclic alkyl group having 3 to 7 carbon atoms, oxo group, thioxo group, fluorine atom, chlorine atom, trifluoromethyl group, —(CH$_2$)$_i$R$^{14}$, —OR$^{10}$, —N(R$^{11}$)(R$^{12}$), —SO$_2$R$^{13}$, or —COR$^{27}$. R$^{10}$ represents hydrogen atom, a lower alkyl group having 1 to 4 carbon atoms, or —(CH$_2$)$_i$R$^{14}$. R$^{11}$ represents hydrogen atom or a lower alkyl group having 1 to 4 carbon atoms. R$^{12}$ represents hydrogen atom, a lower alkyl group having 1 to 4 carbon atoms, a hydroxyalkyl group having 2 to 4 carbon atoms, —COR$^{15}$, or —SO$_2$R$^{16}$, or binds to R$^{11}$ to form a 3- to 6-membered ring together with the nitrogen atom to which they bind to represent a saturated nitrogen-containing cycloalkyl group or morpholino group. R$^{15}$ represents a lower alkyl group having 1 to 4 carbon atoms, a hydroxyalkyl group having 2 to 4 carbon atoms, amino group, a mono- or dialkylamino group having 1 to 4 carbon atoms, or -A$^6$-Qa. R$^{13}$ and R$^{16}$ independently represent a lower alkyl group having 1 to 4 carbon atoms, amino group, or a mono- or dialkylamino group having 1 to 4 carbon atoms. R$^{27}$ represents hydrogen atom, hydroxyl group, an alkoxy group having 1 to 4 carbon atoms, a lower alkyl group having 1 to 4 carbon atoms, amino group, or a mono- or dialkylamino group having 1 to 4 carbon atoms.

Y represents hydrogen atom, a lower alkyl group having 1 to 4 carbon atoms, —(CH$_2$)$_m$N(R$^{18}$)(R$^{19}$), or —C(R$^{20}$)$_2$OC(O)A$^3$R$^{21}$. Symbol m represents an integer of 2 or 3. R$^{18}$ is the same as R$^{19}$, or binds to R$^{19}$ to form a 3- to 6-membered ring together with the nitrogen atom to which they bind to represent a saturated nitrogen-containing cycloalkyl group or morpholino group. R$^{19}$ represents methyl group, ethyl group, or propyl group. R$^{20}$ represents hydrogen atom, methyl group, ethyl group, or propyl group. R$^{21}$ represents a lower alkyl group having 1 to 4 carbon atoms, a cyclic saturated alkyl group having 3 to 6 carbon atoms, or phenyl group, and $A^3$ represents a single bond, or oxygen atom] or a salt thereof as an active ingredient, and a pharmaceutically acceptable carrier, wherein the composition does not substantially contain any reducing sugar and/or a carrier containing a reducing sugar as an ingredient as the pharmaceutically acceptable carrier, or when the composition contains a reducing sugar and/or a carrier containing a reducing sugar as an ingredient as the pharmaceutically acceptable carrier, contact of the reducing sugar and the compound represented by the general formula (I) or a salt thereof is eliminated.

[A1-2] The pharmaceutical composition according to [A1] mentioned above (except for a pharmaceutical composition comprising only methylcellulose as the pharmaceutically acceptable carrier, and a pharmaceutical composition comprising only carboxymethylcellulose as the pharmaceutically acceptable carrier).

[A1-3] The pharmaceutical composition according to [A1] mentioned above (except for a pharmaceutical composition comprising only methylcellulose as the pharmaceutically acceptable carrier, a pharmaceutical composition comprising only methylcellulose and water as the pharmaceutically acceptable carrier, a pharmaceutical composition comprising only carboxymethylcellulose as the pharmaceutically acceptable carrier, and a pharmaceutical composition comprising only carboxymethylcellulose and water as the pharmaceutically acceptable carrier).

[A2] The pharmaceutical composition according to any one of [A1] to [A1-3] mentioned above, which does not substantially contain any reducing sugar and/or carrier containing a reducing sugar as an ingredient as the pharmaceutically acceptable carrier.

[A2-2] The pharmaceutical composition according to any one of [A1] to [A1-3] mentioned above, which contains a reducing sugar as the pharmaceutically acceptable carrier, but comprises a means for eliminating contact of the compound represented by the general formula (I) or a salt thereof and the reducing sugar.

[A2-3] The pharmaceutical composition according to any one of [A1] to [A2] mentioned above, wherein reducing sugar content is 5 weight % or less in terms of glucose.

When the cited item numbers are indicated with a certain range such as [A1] to [A2] mentioned above, and the range include numbers having a subnumber such as [A1-2], it is meant that the items having a subnumber such as [A1-2] are also cited. The same shall apply to the following items.

[A3] The pharmaceutical composition according to any one of [A1] to [A2-3] mentioned above, wherein pharmaceutical composition is a pharmaceutical composition in a dry form.

[A3-2] The pharmaceutical composition according to any one of [A1] to [3] mentioned above, wherein the pharmaceutically acceptable carrier is a dry carrier.

[A3-3] The pharmaceutical composition according to any one of [A1] to [A3-2] mentioned above, wherein moisture content is 10 weight % or less.

[A4] The pharmaceutical composition according to any one of [A1] to [A3-3] mentioned above, which does not substantially contain as the pharmaceutically acceptable carrier any reducing sugar selected from the group consisting of fructose, xylose, lactose, glucose, maltose, and maltitol and/or carrier containing such a reducing sugar as an ingredient.

[A4-2] The pharmaceutical composition according to any one of [A1] to [A3-3] mentioned above, which does not substantially contain as the pharmaceutically acceptable carrier any reducing sugar which gives a difference of 50 mV or less between oxidation reduction potential of a 0.1 moL/L aqueous solution of the reducing sugar and oxidation reduction potential of water used for dissolving the reducing sugar and/or carrier containing such a reducing sugar as an ingredient.

[A5] The pharmaceutical composition according to any one of [A1] to [A4-2] mentioned above, wherein the pharmaceutically acceptable carrier consists of one or more kinds of carriers selected from the group consisting of cellulose derivatives, starches, starch derivatives, synthetic polymer compounds, non-reducing sugars, polyhydric alcohols, fatty acid derivatives, and inorganic substances.

[A5-2] The pharmaceutical composition according to any one of [A1] to [A4-2] mentioned above, wherein the pharmaceutically acceptable carrier consists of one or more kinds of carriers selected from the group consisting of crystalline cellulose, mannitol, methylcellulose, croscarmellose sodium, corn starch, anhydrous calcium hydrogenphosphate, hydroxypropylcellulose, crospovidone, sucrose, povidone, sodium carboxymethyl starch, low substituted hydroxypropylcellulose, partially pregelatinized starch, hydroxypropylmethylcellulose, erythritol, carmellose, polyvinyl alcohol, trehalose, carmellose calcium, magnesium stearate, and carmellose sodium.

[A5-3] The pharmaceutical composition according to any one of [A1] to [A4-2] mentioned above, wherein the pharmaceutically acceptable carrier consists of one or more kinds of carriers selected from the group consisting of crystalline cellulose, mannitol, croscarmellose sodium, corn starch, anhydrous calcium hydrogenphosphate, sucrose, povidone, sodium carboxymethyl starch, low substituted hydroxypropylcellulose, partially pregelatinized starch, hydroxypropylmethylcellulose, erythritol, polyvinyl alcohol, magnesium stearate, and carmellose calcium.

[A5-4] The pharmaceutical composition according to any one of [A1] to [A4-2] mentioned above, wherein the pharmaceutically acceptable carrier consists of one or more kinds of carriers selected from the group consisting of crystalline cellulose, mannitol, croscarmellose sodium, corn starch, anhydrous calcium hydrogenphosphate, sucrose, sodium carboxymethyl starch, low substituted hydroxypropylcellulose, partially pregelatinized starch, hydroxypropylmethylcellulose, erythritol, polyvinyl alcohol, and carmellose calcium.

[A5-5] The pharmaceutical composition according to any one of [A1] to [A4-2] mentioned above, wherein the pharmaceutically acceptable carrier consists of one or more kinds of carriers selected from the group consisting of erythritol, trehalose, mannitol, and sucrose.

[A5-6] The pharmaceutical composition according to any one of [A1] to [A4-2] mentioned above, wherein the pharmaceutically acceptable carrier consists of one or more kinds of carriers selected from the group consisting of mannitol, crystalline cellulose, povidone, and sodium carboxymethyl starch.

[A6] The pharmaceutical composition according to any one of [A1] to [A5-6] mentioned above, wherein, in the formula (I), Link is —$(CH_2)_n$—, n is an integer of 1 to 3, Rz has the same meaning as that of Rx or represents -$A^5$-Re when Rs is —N(Ry)(Rz), and Ry is hydrogen atom, an alkyl group having 1 to 8 carbon atoms, or -$A^6$-Qp, or Ry binds to Rz to form, together with a nitrogen atom to which they bind, a saturated or unsaturated nitrogen-containing cyclic substituent having 3 to 7 atoms.

[A7] The pharmaceutical composition according to [A6] mentioned above, wherein, in the formula (I), AR is a residue of naphthalene, benzofuran, benzo[b]thiophene, indole, benzothiazole, dihydro-3H-benzothiazole, quinoline, dihydro-1H-quinoline, benzo[d]isothiazole, 1H-indazole, benzo[c]isothiazole, 2H-indazole, imidazo[1,2-a]pyridine, 1H-pyrrolo[2,3-b]pyridine, isoquinoline, dihydro-2H-isoquinoline, cinnoline, quinazoline, quinoxaline, 1H-benzimidazole, benzoxazole, 1H-pyrrolo[3,2-b]pyridine, benzo[1,2,5] thiadiazole, 1H-benzotriazole, 1,3-dihydropyrrolo[2,3-b]pyridine, 1,3-dihydrobenzimidazole, dihydro-3H-benzoxazole, phthalazine, [1,8] naphthalidine, [1,5] naphthalidine, 1H-pyrrolo[3,2-c]pyridine, 1H-pyrrolo[2,3-c]pyridine, 1H-pyrazolo[4,3-b]pyridine, 1H-pyrazolo[4,3-c]pyridine, 1H-pyrazolo[3,4-c]pyridine, 1H-pyrazolo[3,4-b]pyridine, [1,2,4]triazolo[4,3-a]pyridine, thieno[3,2-c]pyridine, thieno[3,2-b]pyridine, 1H-thieno[3,2-c]pyrazole, benzo[d] isoxazole, benzo[c]isoxazole, indolizine, 1,3-dihydroindole, 1H-pyrazolo[3,4-d]thiazole, 2H-isoindole, [1,2,4]triazolo[1,5-a]pyrimidine, 1H-pyrazolo[3,4-b]pyrazine, 1H-imidazo[4,5-b]pyrazine, 7H-purine, or 4H-chromene (the aforementioned residues may be substituted with one of Xa or two or more of the same or different Xa).

[A8] The pharmaceutical composition according to [A6] mentioned above wherein, in the formula (I), AR is naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthylidin-3-yl group, [1,8]naphthylidin-4-yl group, [1,5]naphthylidin-3-yl group, [1,5]naphthylidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizin-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, or 4H-chromen-5-yl group (the aforementioned groups may be substituted with one of Xa or two or more of the same or different Xa).

[A9] The pharmaceutical composition according to any one of [A6] to [A8] mentioned above, wherein, in the formula (I), Rs is -D-Rx or —N(Ry)(Rz), D is a single bond, oxygen atom, sulfur atom, —S(O)—, —S(O)$_2$—, or —C(O)—, Rx is a linear or branched saturated alkyl group having 3 to 8 carbon atoms, or Ra, Rb, or Rc, k in Ra is 0 or an integer of 1 to 3, $R^1$ is a saturated cycloalkyl group having 3 to 7 carbon atoms or a condensed saturated cycloalkyl group having 6 to 8 carbon atoms, $R^1$ may be substituted with one of lower alkyl group having 1 to 4 carbon atoms or two or more of the same or different lower alkyl groups having 1 to 4 carbon atoms, Q in Rb is phenyl group, thienyl group, furyl group, pyrrolyl group, pyridyl group, oxazolyl group, isoxazolyl group, thiazolyl group, isothiazolyl group, imidazolyl group, pyrazolyl group, oxadiazolyl group, thiadiazolyl group, triazolyl group, tetrazolyl group, naphthyl group, tetrahydronaphthyl group, indanyl group, indenyl group, quinolyl group, isoquinolyl group, indolyl group, benzofuryl group, benzothienyl group, benzimidazolyl group, benzoxazolyl group, benzothiazolyl group, indazolyl group, 4H-chromenyl group, dihydrobenzodioxyl group, benzoisoxazolyl group, pyrrolopyridinyl group, pyrazolopyridinyl group, triazolopyridinyl group, thienopyridinyl group, thienopyrazolyl group, 1,3-dihydrobenzimidazole group, dihydro-3H-benzoxazole group, or dihydro-3H-benzothiazole group (the aforementioned groups binds to $A^2$ at an arbitrary position), $A^1$ is a single bond or an alkylene (a) having 1 to 3 carbon atoms, the alkylene (a) may be substituted with a lower alkyl group having 1 to 4 carbon atoms or phenyl group, $A^2$ is a single bond, oxygen atom, sulfur atom, S(O)—, —S(O)$_2$—, or —N($R^4$)— (provided that when $A^2$ represents oxygen atom, sulfur atom, —S(O)—, —S(O)$_2$—, or —N($R^4$)—, $A^1$ represents ethylene or trimethylene), $R^2$ and $R^3$ independently represent hydrogen atom, a linear or branched saturated alkyl group having 1 to 4 carbon atoms, oxo group, thioxo group, fluorine atom, chlorine atom, bromine atom, trifluoromethyl group, —O$R^5$, —N($R^6$)($R^{6'}$), —NHCO$R^7$, —NHSO$_2R^8$, or -$A^6$-Qa, or they bind to each other to represent methylenedioxy group, Qa is phenyl group, pyridyl group, oxazolyl group, isoxazolyl group, thiazolyl group, isothiazolyl group, imidazolyl group, pyrazolyl group, oxadiazolyl group, thiadiazolyl group, triazolyl group, tetrazolyl group, naphthyl group, indanyl group, indenyl group, quinolyl group, isoquinolyl group, indolyl group, benzofuryl group, benzothienyl group, benzimidazolyl group, benzoxazolyl group, benzothiazolyl group, or indazolyl group (these groups may be substituted with one of $T^1$ or two or more of the same or different $T^1$, and bind to $A^6$ at an arbitrary position on the ring), $R^4$ and $R^6$ independently represent hydrogen atom or a lower alkyl group having 1 to 4 carbon atoms, $R^5$ and $R^7$ independently represent hydrogen atom, a lower alkyl group having 1 to 4 carbon atoms, or -$A^6$-Qa, $R^8$ is a lower alkyl group having 1 to 4 carbon atoms, $R^{6'}$ has the same meaning as $R^6$, or binds to $R^6$ to form a 3- to 6-membered ring together with the nitrogen atom to which they bind to form a saturated nitrogen-containing cycloalkyl group or morpholino group, p in Rc is an integer of 2 to 4, $A^4$ is a single bond or methylene or ethylene, $A^5$ is —C(O)—, —C(S)—, or —S(O)$_2$—, Rd is hydrogen atom, an alkyl group having 1 to 8 carbon atoms, or Qa, Re is an alkyl group having 1 to 8 carbon atoms, -$A^6$-Qa, —(CH$_2$)$_iR^{14}$, —O$R^{28}$, —S$R^{28}$, or —N($R^{29}$)($R^{30}$), i is an integer of 1 to 3, $R^{14}$ is hydroxyl group, an alkoxy group having 1 to 4 carbon atoms, carboxyl group, or an N,N-dialkylcarbamoyl group having 1 to 4 carbon atoms, $R^{28}$ is an alkyl group having 1 to 8 carbon atoms or -$A^6$-Qa, $R^{29}$ is an alkyl group having 1 to 8 carbon atoms, an alkoxycarbonyl group having 1 to 4 carbon atoms, or -$A^6$-Qa, $R^{30}$ is hydrogen atom or a lower alkyl group having 1 to 4 carbon atoms, or binds to $R^{29}$ to form a 3- to 6-membered ring together with the nitrogen atom to which they bind to form a saturated nitrogen-containing cycloalkyl group or morpholino group, Rz has the same meaning as Rx, or is -$A^5$-Re, and Ry is hydrogen atom, an alkyl group having 1 to 8 carbon atoms, or -$A^6$-Qp, or binds to Rz to form a saturated or unsaturated nitrogen-containing cyclic substituent having 3 to 7 atoms together with nitrogen atom to which they binds.

[A10] The pharmaceutical composition according to any one of [A6] to [A9] mentioned above, wherein, in the general formula (I), Rs is —O-Rx.

[A11] The pharmaceutical composition according to [A6] mentioned above, wherein, in the formula (I), AR binds at the position of $C^3$ in the aromatic ring (E), and Rs binds to one of the ring-constituting carbon atoms $C^4$, $C^5$, and $C^6$.

[A12] The pharmaceutical composition according to [A6] mentioned above, wherein, in the formula (I), AR binds at the position of $C^2$ in the aromatic ring (E), and Rs binds to one of ring-constituting carbon atoms $C^3$, $C^4$ and $C^5$.

[A13] The pharmaceutical composition according to [A12] mentioned above, wherein, in the general formula (I), n is an integer of 2, and Y is hydrogen atom or a lower alkyl group having 1 to 4 carbon atoms.

[A14] The pharmaceutical composition according to [A11] mentioned above, wherein, in the general formula (I), Rs binds to one of ring-constituting carbon atoms $C^5$ and $C^6$ in the aromatic ring (E).

[A15] The pharmaceutical composition according to [A11] mentioned above, wherein, in the general formula (I), Rs binds to $C^4$ in the aromatic ring (E), and $C^6$ is a carbon atom substituted with amino group.

[A16] The pharmaceutical composition according to [A15] mentioned above, wherein, in the general formula (I), n is an integer of 2, D is oxygen atom, and Y is hydrogen atom or a lower alkyl group having 1 to 4 carbon atoms.

[A17] The pharmaceutical composition according to [A11] mentioned above, wherein, in the general formula (I), Rs binds to $C^4$ in the aromatic ring (E), $C^5$ is a carbon atom substituted with amino group, $C^2$ and $C^6$ are unsubstituted ring-constituting carbon atoms, and Rs is —N(Ry)(Rz).

[A18] The pharmaceutical composition according to any one of [A1] to [A5-6] mentioned above, wherein, in the general formula (I), Link is —(CH$_2$)$_n$—, n is an integer of 1 to 3, $C^2$ and $C^6$ in the aromatic ring (E) are unsubstituted ring-constituting carbon atoms, AR binds at the position of $C^3$ in the aromatic ring (E), Rs is —N(Ry)(Rz), and binds at the position of $C^4$ in the aromatic ring (E).

[A19] The pharmaceutical composition according to [A18] mentioned above, wherein, in the general formula (I), n is an integer of 2, and $C^5$ is a carbon atom substituted with amino group.

[A20] The pharmaceutical composition according to [A11] mentioned above, wherein, in the general formula (I), Rs binds to $C^4$ in the aromatic ring (E), $C^5$ is a carbon atom substituted with amino group, $C^2$ and $C^6$ are unsubstituted ring-constituting carbon atoms, Rs is -D-Rx, and D is a single bond, sulfur atom, —S(O)—, —S(O)$_2$—, or —C(O)—.

[A21] The pharmaceutical composition according to [A11] mentioned above, wherein, in the general formula (I), n is an integer of 2, Rs binds to $C^4$ in the aromatic ring (E), $C^5$ is a carbon atom substituted with amino group, $C^2$ and $C^6$ are unsubstituted ring-constituting carbon atoms, Rs is —O-Rx, and Y is hydrogen atom or a lower alkyl group having 1 to 4 carbon atoms.

[A22] The pharmaceutical composition according to [A11] mentioned above, wherein, in the general formula (I), n is an integer of 2, Rs binds to $C^4$ in the aromatic ring (E), $C^5$ is a carbon atom substituted with amino group, $C^2$ and $C^6$ are unsubstituted ring-constituting carbon atoms, Rs is —O-Rc, and Y is hydrogen atom or a lower alkyl group having 1 to 4 carbon atoms.

[A23] The pharmaceutical composition according to [A6] mentioned above, wherein, in the general formula (I), AR binds at the position of $C^3$ in the aromatic ring (E), Rs binds at the position of $C^4$ in the aromatic ring (E), $C^5$ is a carbon atom substituted with amino group, Rs is -D-Rx, D is oxygen atom, Rx is a linear or branched saturated alkyl group having 3 to 8 carbon atoms, or Ra or Rb, k in Ra is 0 or an integer of 1 to 3, $R^1$ is a saturated cycloalkyl group having 3 to 7 carbon atoms or a condensed saturated cycloalkyl group having 6 to 8 carbon atoms, $R^1$ may be substituted with one of lower alkyl group having 1 to 4 carbon atoms or two or more of the same or different lower alkyl groups having 1 to 4 carbon atoms, Q in Rb represents a partially unsaturated or completely unsaturated monocyclic or condensed bicyclic carbon ring or a heterocyclic ring (q) (Q binds to $A^2$ at an arbitrary position on the ring), $A^1$ is a single bond or an alkylene (a) having 1 to 3 carbon atoms, the alkylene (a) may be substituted with a lower alkyl group having 1 to 4 carbon atoms or phenyl group, $A^2$ represents a single bond, oxygen atom, sulfur atom, —S(O)—, —S(O)$_2$—, or —N(R$^4$)— (provided that when $A^2$ represents oxygen atom, sulfur atom, —S(O)—, —S(O)$_2$—, or —N(R$^4$)—, $A^1$ is ethylene or trimethylene), $R^2$ and $R^3$ independently represent hydrogen atom, a linear or branched saturated alkyl group having 1 to 4 carbon atoms, fluorine atom, chlorine atom, bromine atom, trifluoromethyl group, —OR$^6$, —N(R$^6$)(R$^{6'}$), —NHCOR$^7$, —NHSO$_2$R$^8$, or -$A^6$-Qa, or they bind to each other to form methylenedioxy group, Qa is a partially unsaturated or completely unsaturated monocyclic or condensed bicyclic carbon ring or a heterocyclic ring (qa) (Qa may be substituted with one of T$^1$ or two or more of the same or different T$^1$, and binds to $A^6$ at an arbitrary position on the ring), $R^4$, $R^6$ and $R^7$ independently represent hydrogen atom or a lower alkyl group having 1 to 4 carbon atoms, $R^5$ and $R^8$ are lower alkyl groups having 1 to 4 carbon atoms, and $R^{6'}$ has the same meaning as that of $R^6$, or binds to $R^6$ to form a 3- to 6-membered ring together with the nitrogen atom to which they bind to form a saturated nitrogen-containing cycloalkyl group or morpholino group.

[A24] The pharmaceutical composition according to [A23] mentioned above, wherein, in the general formula (I), AR is a residue of naphthalene, benzofuran, benzo[b]thiophene, indole, benzothiazole, dihydro-3H-benzothiazole, quinoline, dihydro-1H-quinoline, benzo[d]isothiazole, 1H-indazole, benzo[c]isothiazole, 2H-indazole, imidazo[1,2-a]pyridine, 1H-pyrrolo[2,3-b]pyridine, isoquinoline, dihydro-2H-isoquinoline, cinnoline, quinazoline, quinoxaline, 1H-benzimidazole, benzoxazole, 1H-pyrrolo[3,2-b]pyridine, benzo[1,2,5]thiadiazole, 1H-benzotriazole, 1,3-dihydropyrrolo[2,3-b]pyridine, 1,3-dihydrobenzimidazole, dihydro-3H-benzoxazole, phthalazine, [1,8]naphthylidine, [1,5]naphthylidine, 1H-pyrrolo[3,2-c]pyridine, 1H-pyrrolo[2,3-c]pyridine, 1H-pyrazolo[4,3-b]pyridine, 1H-pyrazolo[4,3-c]pyridine, 1H-pyrazolo[3,4-c]pyridine, 1H-pyrazolo[3,4-b]pyridine, [1,2,4]triazolo[4,3-a]pyridine, thieno[3,2-c]pyridine, thieno[3,2-b]pyridine, 1H-thieno[3,2-c]pyrazole, benzo[d]isoxazole, benzo[c]isoxazole, indolizine, 1,3-dihydroindole, 1H-pyrazolo[3,4-d]thiazole, 2H-isoindole, [1,2,4]triazolo[1,5-a]pyrimidine, 1H-pyrazolo[3,4-b]pyrazine, 1H-imidazo[4,5-b]pyrazine, 7H-purine, or 4H-chromene (the aforementioned residue may be substituted with one of Xa or two or more of the same or different Xa).

[A25] The pharmaceutical composition according to [A23] mentioned above, wherein, in the general formula (I), AR is naphthalen-2-yl group, naphthalen-1-yl group, benzofuran- 5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthylidin-3-yl group, [1,8]naphthylidin-4-yl group, [1,5]naphthylidin-3-yl group, [1,5]naphthylidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizin-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, or 4H-chromen-5-yl group (the aforementioned groups may be substituted with one of Xa or two or more of the same or different Xa).

[A26] The pharmaceutical composition according to [A24] or [A25] mentioned above, wherein, in the general formula (I), Rx is a linear or branched saturated alkyl group having 3 to 8 carbon atoms, or Ra, $R^1$ is a saturated cycloalkyl group having 3 to 7 carbon atoms or a condensed saturated cycloalkyl group having 6 to 8 carbon atoms, and $R^1$ is a group which may be substituted with one of lower alkyl group having 1 to 4 carbon atoms or two or more of the same or different lower alkyl groups having 1 to 4 carbon atoms.

[A27] The pharmaceutical composition according to [A24] or [A25] mentioned above, wherein, in the general formula (I), Rx is Rb; Q in Rb is phenyl group or indanyl group; when Q is phenyl group, $A^1$ is a single bond or unsubstituted methylene, and when $A^2$ is a single bond, one of $R^2$ and $R^3$ is a substituent other than hydrogen atom.

[A28] The pharmaceutical composition according to [A23] mentioned above, wherein, in the general formula (I), n is an integer of 2; Rx is butyl group, isobutyl group, 2-ethylbutyl group, cyclopentyl group, cyclohexyl group, cyclopentylmethyl group, or cyclohexylmethyl group, or the substituent Rb, provided that the group Q in Rb is phenyl group or indanyl group; $A^1$ is a single bond, a methylene group substituted with 1 to 3 methyl groups or ethyl groups or unsubstituted methylene group, or an ethylene group substituted with 1 to 3 methyl groups or ethyl groups or unsubstituted ethylene group; $A^2$ is a single bond; $R^2$ and $R^3$ are both hydrogen atoms, or independently represent methyl group, fluorine atom, chlorine atom, trifluoromethyl group, methoxy group, or dimethylamino group, provided that when Q is phenyl group, $A^1$ is a single bond, or unsubstituted methylene, one of $R^2$ and $R^3$ is a substituent other than hydrogen atom; the substituent AR is naphthalen-2-yl group, benzofuran-5-yl group, benzo[b]thiophen-5-yl group, indol-5-yl group, benzothiazol-6-yl group, quinolin-6-yl group, quinolin-3-yl group, isoquinolin-6-yl group, or 1H-indazol-5-yl group (the aforementioned residue may be substituted with one of Xa or two or more of the same or different Xa, and Xa represents a linear or branched saturated alkyl group having 1 to 4 carbon atoms); and Y is hydrogen atom, methyl group or ethyl group.

[A29] The pharmaceutical composition according to [A23] mentioned above, wherein, in the general formula (I), n is an integer of 2; Rx is butyl group, isobutyl group, 2-ethylbutyl group, cyclopentyl group, cyclohexyl group, cyclopentylmethyl group, or cyclohexylmethyl group, or the substituent Rb, provided that Q in the group Rb is phenyl group; $A^1$ is a single bond, a methylene group substituted with 1 to 3 methyl groups or ethyl groups or unsubstituted methylene group, or an ethylene group substituted with 1 to 3 methyl groups or ethyl groups or unsubstituted ethylene group; $A^2$ is a single bond; $R^2$ and $R^3$ are both hydrogen atoms, or independently represent methyl group, fluorine atom, chlorine atom, trifluoromethyl group, methoxy group, or dimethylamino group, provided that $A^1$ is a single bond, or unsubstituted methylene, and one of $R^2$ and $R^3$ is a substituent other than hydrogen atom; the substituent AR is naphthalen-2-yl group, benzofuran-5-yl group, benzo[b]thiophen-5-yl group, indol-5-yl group, benzothiazol-6-yl group, quinolin-6-yl group, quinolin-3-yl group, isoquinolin-6-yl group, or 1H-indazol-5-yl group (the aforementioned residue may be substituted with one of Xa or two or more of the same or different Xa, and Xa represents a linear or branched saturated alkyl group having 1 to 4 carbon atoms); and Y is hydrogen atom, methyl group or ethyl group.

[A30] The pharmaceutical composition according to [A23] mentioned above, wherein, in the general formula (I), n is an integer of 2; Rx is butyl group, isobutyl group, 2-ethylbutyl group, cyclopentyl group, cyclohexyl group, cyclopentylmethyl group, or cyclohexylmethyl group, or the substituent Rb, provided that Q in the group Rb is indan-2-yl group; $A^1$ is a single bond, a methylene group substituted with 1 to 3 methyl groups or ethyl groups or unsubstituted methylene group, or an ethylene group substituted with 1 to 3 methyl groups or ethyl groups or unsubstituted ethylene group; $A^2$ is a single bond; $R^2$ and $R^3$ are both hydrogen atoms, or independently represent methyl group, fluorine atom, chlorine atom, trifluoromethyl group, methoxy group, or dimethylamino group; the substituent AR is naphthalen-2-yl group, benzofuran-5-yl group, benzo[b]thiophen-5-yl group, indol-5-yl group, benzothiazol-6-yl group, quinolin-6-yl group, quinolin-3-yl group, isoquinolin-6-yl group, or 1H-indazol-5-yl group (the aforementioned residue may be substituted with one of Xa or two or more of the same or different Xa, and Xa represents a linear or branched saturated alkyl group having 1 to 4 carbon atoms); and Y is hydrogen atom, methyl group or ethyl group.

[A31] The pharmaceutical composition according to any one of [A1] to [A30] mentioned above, wherein the compound represented by the general formula (I) or a salt thereof is any one of 3-[3-amino-4-(indan-2-yloxy)-5-(1-methyl-1H-indazol-5-yl)phenyl]propionic acid, 3-{3-amino-4-[2-(4-methylphenyl)ethyloxy]-5-(naphthalen-2-yl)phenyl}propionic acid, 3-[3-amino-4-cyclopentylmethyloxy-5-(1H-indol-5-yl)phenyl]propionic acid, 3-[3-amino-4-cyclopentylmethyloxy-5-(1-methyl-1H-indol-5-yl)phenyl]propionic acid, and 3-[3-amino-4-(indan-2-yloxy)-5-(1H-indazol-5-yl)phenyl]propionic acid.

[A32] The pharmaceutical composition according to any one of [A1] to [A30] mentioned above, wherein the compound represented by the general formula (I) or a salt thereof is 3-[3-amino-4-(indan-2-yloxy)-5-(1-methyl-1H-indazol-5-yl)phenyl]propionic acid.

[A33] The pharmaceutical composition according to any one of [A1] to [A32] mentioned above, which is in the form of a solid preparation.

[A33-2] The pharmaceutical composition according to any one of [A1] to [A33] mentioned above, wherein decomposition of the compound represented by the general formula (I) or a salt thereof is prevented.

[A33-3] The pharmaceutical composition according to any one of [A1] to [A33] mentioned above, wherein coloring of the compound represented by the general formula (I) or a salt thereof is prevented.

[A34] A method for preparing a pharmaceutical composition comprising a compound represented by the general formula (I) or a salt thereof according to [A1] mentioned above as an active ingredient, and a pharmaceutically acceptable carrier, which comprises the step of preparing the pharmaceutical composition by using a carrier other than a reducing sugar and/or a carrier containing a reducing sugar as an ingredient as the pharmaceutically acceptable carrier, or when a reducing sugar and/or a carrier containing a reducing sugar as an ingredient is used as the pharmaceutically acceptable carrier, with eliminating contact of the reducing sugar and the compound represented by the general formula (I) or a salt thereof.

[A34-2] A method for preparing the pharmaceutical composition according to [A1-2] mentioned above, which comprises the step of preparing the pharmaceutical composition by using a carrier other than a reducing sugar and/or a carrier containing a reducing sugar as an ingredient as the pharmaceutically acceptable carrier, or when a reducing sugar and/or a carrier containing a reducing sugar as an ingredient is used as the pharmaceutically acceptable carrier, by eliminating contact of the reducing sugar and the compound represented by the general formula (I) or a salt thereof.

[A34-3] A method for preparing the pharmaceutical composition according to [A1-3] mentioned above, which comprises the step of preparing the pharmaceutical composition by using a carrier other than a ducing sugar and/or a rrier containing a reducing sugar as an ingredient as the pharmaceutically acceptable carrier, or when a reducing sugar and/or a carrier containing a reducing sugar as an ingredient is used as the pharmaceutically acceptable carrier, by eliminating contact of the reducing sugar and the compound represented by the general formula (I) or a salt thereof.

[A35] The preparation method according to any one of [A34] to [A34-3] mentioned above, which comprises the step of preparing the pharmaceutical composition by using a carrier other than a reducing sugar and/or a carrier containing a reducing sugar as an ingredient.

[A35-2] The preparation method according to any one of [A34] to [A34-3] mentioned above, which comprises the step of preparing the pharmaceutical composition by using a reducing sugar and/or a carrier containing a reducing sugar as an ingredient, with eliminating contact of the reducing sugar and the compound represented by the general formula (I) or a salt thereof.

[A35-3] The preparation method according to any one of [A34] to [A35] mentioned above, wherein reducing sugar content in the pharmaceutical composition is 5 weight % or less in terms of glucose.

[A36] The preparation method according to any one of [A34] to [A35-3] mentioned above, wherein the pharmaceutical composition is a pharmaceutical composition in a dry form.

[A36-2] The preparation method according to any one of [A34] to [A36] mentioned above, wherein the pharmaceutically acceptable carrier is a dry carrier.

[A36-3] The preparation method according to any one of [A34] to [A36-2] mentioned above, wherein moisture content in the pharmaceutical composition is 10 weight % or less.

[A37] The method according to any one of [A34] to [A36-3] mentioned above, which does not use a reducing sugar selected from the group consisting of fructose, xylose, lactose, glucose, maltose, and maltitol and/or a carrier containing such a reducing sugar as an ingredient as the pharmaceutically acceptable carrier.

[A38] The preparation method according to any one of [A34] to [A37] mentioned above, wherein the pharmaceutically acceptable carrier consists of one or more kinds of carriers selected from the group consisting of cellulose derivatives, starches, starch derivatives, synthetic polymer compounds, non-reducing sugar, polyhydric alcohols, fatty acid derivatives, and inorganic substances.

[A38-2] The preparation method according to any one of [A34] to [A37] mentioned above, wherein the pharmaceutically acceptable carrier consists of one or more kinds of carriers selected from the group consisting of crystalline cellulose, mannitol, methylcellulose, croscarmellose sodium, corn starch, anhydrous calcium hydrogenphosphate, hydroxypropylcellulose, crospovidone, sucrose, povidone, sodium carboxymethyl starch, low substituted hydroxypropylcellulose, partially pregelatinized starch, hydroxypropylmethylcellulose, erythritol, carmellose, polyvinyl alcohol, trehalose, carmellose calcium, magnesium stearate, and carmellose sodium.

[A39] The preparation method according to any one of [A34] to [A38-2] mentioned above, wherein the compound represented by the general formula (I) or a salt thereof is the compound or a salt thereof according to any one of [A6] to [A32] mentioned above.

[A40] A method for stabilizing a pharmaceutical composition comprising a compound represented by the general formula (I) or a salt thereof according to [A1] mentioned above as an active ingredient, and a pharmaceutically acceptable carrier, which comprises the step of preparing the pharmaceutical composition by using a carrier other than a reducing sugar and/or a carrier containing a reducing sugar as an ingredient as the pharmaceutically acceptable carrier, or when a reducing sugar and/or a carrier containing a reducing sugar as an ingredient is used as the pharmaceutically acceptable carrier, with eliminating contact of the reducing sugar and the compound represented by the general formula (I) or a salt thereof.

[A40-2] A method for stabilizing the pharmaceutical composition according to [A1-2] mentioned above, which comprises the step of preparing the pharmaceutical composition by using a carrier other than a reducing sugar and/or a carrier containing a reducing sugar as an ingredient as the pharmaceutically acceptable carrier, or when a reducing sugar and/or a carrier containing a reducing sugar as an ingredient is used as the pharmaceutically acceptable carrier, with eliminating contact of the reducing sugar and the compound represented by the general formula (I) or a salt thereof.

[A40-3] A method for stabilizing the pharmaceutical composition according to [A1-3] mentioned above, which comprises the step of preparing the pharmaceutical composition by using a carrier other than a reducing sugar and/or a carrier containing a reducing sugar as an ingredient as the pharmaceutically acceptable carrier, or when a reducing sugar and/or a carrier containing a reducing sugar as an ingredient is used as the pharmaceutically acceptable carrier, with eliminating contact of the reducing sugar and the compound represented by the general formula (I) or a salt thereof.

[A41] The stabilization method according to any one of [A40] to [A40-3] mentioned above, which comprises the step of preparing the pharmaceutical composition by using a carrier other than a reducing sugar and/or a carrier containing a reducing sugar as an ingredient.

[A41-2] The stabilization method according to any one of [A40] to [A40-3] mentioned above, which comprises the step of preparing the pharmaceutical composition by using a reducing sugar and/or a carrier containing a reducing sugar as an ingredient, with eliminating contact of the reducing sugar and the compound represented by the general formula (I) or a salt thereof.

[A41-3] The stabilization method according to any one of [A40] to [A41] mentioned above, wherein reducing sugar content in the pharmaceutical composition is 5 weight % or less in terms of glucose.

[A42] The stabilization method according to any one of [A40] to [A41-3] mentioned above, wherein the pharmaceutical composition is a pharmaceutical composition in a dry form.

[A42-2] The stabilization method according to any one of [A40] to [A42] mentioned above, wherein the pharmaceutically acceptable carrier is a dry carrier.

[A42-3] The stabilization method according to any one of [A40] to [A42-2] mentioned above, wherein moisture content in the pharmaceutical composition is 10 weight % or less.

[A43] The stabilization method according to any one of [A40] to [A42-3] mentioned above, wherein the pharmaceutical composition is prepared by using a carrier other than a reducing sugar selected from the group consisting of fructose, xylose, lactose, glucose, maltose, and maltitol and/or a carrier containing such a reducing sugar as an ingredient as the pharmaceutically acceptable carrier.

[A44] The stabilization method according to any one of [A40] to [A43] mentioned above, wherein the pharmaceutically acceptable carrier consists of one or more kinds of carriers selected from the group consisting of cellulose derivatives, starches, starch derivatives, synthetic polymer compounds, non-reducing sugar, polyhydric alcohols, fatty acid derivatives, and inorganic substances.

[A44-2] The stabilization method according to any one of [A40] to [A43] mentioned above, wherein the pharmaceutically acceptable carrier consists of one or more kinds of carriers selected from the group consisting of crystalline cellulose, mannitol, methylcellulose, croscarmellose sodium, corn starch, anhydrous calcium hydrogenphosphate, hydroxypropylcellulose, crospovidone, sucrose, povidone, sodium carboxymethyl starch, low substituted hydroxypropylcellulose, partially pregelatinized starch, hydroxypropylmethylcellulose, erythritol, carmellose, polyvinyl alcohol, trehalose, carmellose calcium, magnesium stearate, and carmellose sodium.

[A44-3] The stabilization method according to any one of [A40] to [A43] mentioned above, wherein the pharmaceutically acceptable carrier consists of one or more kinds of carriers selected from the group consisting of crystalline cellulose, mannitol, croscarmellose sodium, corn starch, anhydrous calcium hydrogenphosphate, sucrose, povidone, sodium carboxymethyl starch, low substituted hydroxypropylcellulose, partially pregelatinized starch, hydroxypropylmethylcellulose, erythritol, polyvinyl alcohol, magnesium stearate, and carmellose calcium.

[A44-4] The stabilization method according to any one of [A40] to [A43] mentioned above, wherein the pharmaceutically acceptable carrier consists of one or more kinds of carriers selected from the group consisting of crystalline cellulose, mannitol, croscarmellose sodium, corn starch, anhydrous calcium hydrogenphosphate, sucrose, sodium carboxymethyl starch, low substituted hydroxypropylcellulose, partially pregelatinized starch, hydroxypropylmethylcellulose, erythritol, polyvinyl alcohol, and carmellose calcium.

[A45] The stabilization method according to any one of [A40] to [A44-4] mentioned above, wherein the compound represented by the general formula (I) or a salt thereof is the compound or a salt thereof according to any one of [A6] to [A32] mentioned above.

[A46] The stabilization method according to any one of [A40] to [A45] mentioned above, which is performed for prevention of coloring of the compound represented by the general formula (I) or a salt thereof.

[A47] The stabilization method according to any one of [A40] to [A45] mentioned above, which is performed for prevention of decomposition of the compound represented by the general formula (I) or a salt thereof.

[A48] A method for storing and/or distributing a pharmaceutical composition comprising the compound represented by the general formula (I) or a salt thereof according to [A1] mentioned above as an active ingredient, and a pharmaceutically acceptable carrier, wherein the pharmaceutical composition is stored and/or distributed after the pharmaceutical composition is prepared by using a carrier other than a reducing sugar and/or a carrier containing a reducing sugar as an ingredient, or when a reducing sugar and/or a carrier containing a reducing sugar as an ingredient is used as the pharmaceutically acceptable carrier, with eliminating contact of the reducing sugar and the compound represented by the general formula (I) or a salt thereof.

[A48-2] The method for storing and/or distributing the pharmaceutical composition according to [A1-2] mentioned above, wherein the pharmaceutical composition is stored and/or distributed after the pharmaceutical composition is prepared by using a carrier other than a reducing sugar and/or a carrier containing a reducing sugar as an ingredient, or when a reducing sugar and/or a carrier containing a reducing sugar as an ingredient is used as the pharmaceutically acceptable carrier, with eliminating contact of the reducing sugar and the compound represented by the general formula (I) or a salt thereof.
[A48-3] The method for storing and/or distributing the pharmaceutical composition according to [A1-3] mentioned above, wherein the pharmaceutical composition is stored and/or distributed after the pharmaceutical composition is prepared by using a carrier other than a reducing sugar and/or a carrier containing a reducing sugar as an ingredient, or when a reducing sugar and/or a carrier containing a reducing sugar as an ingredient is used as the pharmaceutically acceptable carrier, with eliminating contact of the reducing sugar and the compound represented by the general formula (I) or a salt thereof.
[A49] The method according to any one of [A48] to [A48-3] mentioned above, wherein the pharmaceutical composition is stored and/or distributed after the pharmaceutical composition is prepared by using a carrier other than a reducing sugar and/or a carrier containing a reducing sugar as an ingredient.
[A49-2] The method according to any one of [A48] to [A48-3] mentioned above, wherein the pharmaceutical composition is stored and/or distributed after the pharmaceutical composition is prepared by using a reducing sugar and/or a carrier containing a reducing sugar as an ingredient as the pharmaceutically acceptable carrier, with eliminating contact of the reducing sugar and the compound represented by the general formula (I) or a salt thereof.
[A49-3] The method according to any one of [A48] to [A49] mentioned above, wherein reducing sugar content in the pharmaceutical composition is 5 weight % or less in terms of glucose.
[A50] The method according to any one of [A48] to [A49-3] mentioned above, wherein the pharmaceutical composition is a pharmaceutical composition in a dry form.
[A50-2] The method according to any one of [A48] to [50] mentioned above, wherein the pharmaceutically acceptable carrier is a dry carrier.
[A50-3] The method according to any one of [A48] to [A50-2] mentioned above, wherein moisture content in the pharmaceutical composition is 10 weight % or less.
[A51] The method according to any one of [A48] to [A50-3] mentioned above, wherein the pharmaceutical composition prepared by using a carrier other than a reducing sugar selected from the group consisting of fructose, xylose, lactose, glucose, maltose, and maltitol and/or a carrier containing such a reducing sugar as an ingredient as the pharmaceutically acceptable carrier is stored and/or distributed.
[A52] The method according to any one of [A48] to [A51] mentioned above, wherein the pharmaceutically acceptable carrier consists of one or more kinds of carriers selected from the group consisting of cellulose derivatives, starches, starch derivatives, synthetic polymer compounds, non-reducing sugar, polyhydric alcohols, fatty acid derivatives, and inorganic substances.
[A52-2] The method according to any one of [A48] to [A51] mentioned above, wherein the pharmaceutically acceptable carrier consists of one or more kinds of carriers selected from the group consisting of crystalline cellulose, mannitol, methylcellulose, croscarmellose sodium, corn starch, anhydrous calcium hydrogenphosphate, hydroxypropylcellulose, crospovidone, sucrose, povidone, sodium carboxymethyl starch, low substituted hydroxypropylcellulose, partially pregelatinized starch, hydroxypropylmethylcellulose, erythritol, carmellose, polyvinyl alcohol, trehalose, carmellose calcium, magnesium stearate, and carmellose sodium.
[A52-3] The method according to any one of [A48] to [A51] mentioned above, wherein the pharmaceutically acceptable carrier consists of one or more kinds of carriers selected from the group consisting of crystalline cellulose, mannitol, croscarmellose sodium, corn starch, anhydrous calcium hydrogenphosphate, sucrose, povidone, sodium carboxymethyl starch, low substituted hydroxypropylcellulose, partially pregelatinized starch, hydroxypropylmethylcellulose, erythritol, polyvinyl alcohol, magnesium stearate, and carmellose calcium.
[A52-4] The method according to any one of [A48] to [A51] mentioned above, wherein the pharmaceutically acceptable carrier consists of one or more kinds of carriers selected from the group consisting of crystalline cellulose, mannitol, croscarmellose sodium, corn starch, anhydrous calcium hydrogenphosphate, sucrose, sodium carboxymethyl starch, low substituted hydroxypropylcellulose, partially pregelatinized starch, hydroxypropylmethylcellulose, erythritol, polyvinyl alcohol, and carmellose calcium.
[A53] The method according to any one of [A48] to [A52-4] mentioned above, wherein the compound represented by the general formula (I) or a salt thereof is the compound or a salt thereof according to any one of [A6] to [A32] mentioned above.
[B1] A pharmaceutical composition comprising a compound represented by the general formula (I):

[Formula 4]

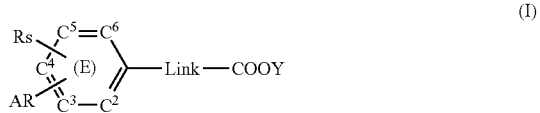

(I)

[In the formula, Link represents a saturated or unsaturated straight hydrocarbon chain having 1 to 3 carbon atoms.

$C^2$, $C^3$, $C^4$, $C^5$, and $C^6$ in the aromatic ring (E) independently represent a ring-constituting carbon atom. One of the ring-constituting carbon atoms to which Rs and AR do not bind represents a carbon atom substituted with amino group.

Rs represents -D-Rx or —N(Ry)(Rz).

D represents a single bond, oxygen atom, sulfur atom, —S(O)—, —S(O)$_2$—, or —C(O)—.

Rx represents a linear or branched saturated alkyl group having 3 to 8 carbon atoms, or represents Ra represented by the following formula:

$R^1(CH_2)_k$— (Ra)

Rb represented by the following formula:

[Formula 5]

(Rb)

or Rc represented by the following formula:

[Formula 6]

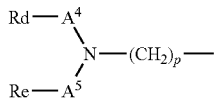

(Rc)

k in Ra represents 0 or an integer of 1 to 3. $R^1$ represents a saturated cyclic alkyl group having 3 to 7 carbon atoms, or a condensed saturated cyclic alkyl group having 6 to 8 carbon atoms, and $R^1$ may be substituted with one of lower alkyl group having 1 to 4 carbon atoms or two or more of the same or different lower alkyl groups having 1 to 4 carbon atoms. Q in Rb represents a partially unsaturated or completely unsaturated monocyclic or condensed bicyclic carbon ring or a heterocyclic ring (q), and binds to $A^2$ at an arbitrary position on the ring. The heterocyclic ring (q) contains the same or different 1 to 4 ring-constituting heteroatoms selected from the group consisting of nitrogen atom, oxygen atom, and sulfur atom. $A^1$ represents a single bond or an alkylene (a) having 1 to 3 carbon atoms, and the alkylene (a) may be substituted with a lower alkyl group having 1 to 4 carbon atoms or phenyl group. $A^2$ represents a single bond, oxygen atom, sulfur atom, —S(O)—, —S(O)$_2$—, or —N(R$^4$)— (provided that when $A^2$ represents oxygen atom, sulfur atom, —S(O)—, —S(O)$_2$— or —N(R$^4$)—, $A^1$ represents ethylene or trimethylene). $R^2$ and $R^3$ independently represent hydrogen atom, a linear or branched saturated alkyl group having 1 to 4 carbon atoms, oxo group, thioxo group, fluorine atom, chlorine atom, bromine atom, trifluoromethyl group, —OR$^5$, —N(R$^6$)(R$^6$'), —NHCOR$^7$, —NHSO$_2$R$^8$, or -A$^6$-Qa, or they bind to each other to represent methylenedioxy group. $A^6$ represents a single bond or methylene. Qa represents a partially unsaturated or completely unsaturated monocyclic or condensed bicyclic carbon ring or a heterocyclic ring (qa), binds to $A^6$ at an arbitrary position on the ring, and may be substituted with one of $T^1$ or two or more of the same or different $T^1$. $T^1$ represents a linear or branched saturated alkyl group having 1 to 4 carbon atoms, hydroxyl group, fluorine atom, chlorine atom, bromine atom, trifluoromethyl group, nitro group, an alkoxy group having 1 to 4 carbon atoms, or a mono- or dialkylamino group having 1 to 4 carbon atoms. The heterocyclic ring (qa) contains the same or different 1 to 4 ring-constituting heteroatoms selected from the group consisting of nitrogen atom, oxygen atom, and sulfur atom. $R^4$ and $R^6$ independently represent hydrogen atom or a lower alkyl group having 1 to 4 carbon atoms. $R^5$ and $R^7$ independently represent hydrogen atom, a lower alkyl group having 1 to 4 carbon atoms, or -A$^6$-Qa. Rs represents a lower alkyl group having 1 to 4 carbon atoms. $R^6$' has the same meaning as $R^6$, or binds to $R^6$ to form a 3- to 6-membered ring together with the nitrogen atom to which they bind to represent a saturated nitrogen-containing cycloalkyl group or morpholino group. p in Rc represents an integer of 2 to 4. $A^4$ represents a single bond, methylene, or ethylene. $A^5$ represents —C(O)—, —C(S)—, or —S(O)$_2$—. Rd represents hydrogen atom, an alkyl group having 1 to 8 carbon atoms, or Qa. Re represents an alkyl group having 1 to 8 carbon atoms, -A$^6$-Qa, —(CH$_2$)$_i$R$^{14}$, —OR$^{28}$, —SR$^{28}$, or —N(R$^{29}$)(R$^{30}$). i represents an integer of 1 to 3, $R^{14}$ represents hydroxyl group, an alkoxy group having 1 to 4 carbon atoms, carboxyl group, or an N,N-dialkylcarbamoyl group having 1 to 4 carbon atoms. $R^{28}$ represents an alkyl group having 1 to 8 carbon atoms, or -A$^6$-Qa. $R^{29}$ represents an alkyl group having 1 to 8 carbon atoms, an alkoxycarbonyl group having 1 to 4 carbon atoms, or -A$^6$-Qa. $R^{30}$ represents hydrogen atom or a lower alkyl group having 1 to 4 carbon atoms, or binds to $R^{29}$ to form a 3- to 6-membered ring together with the nitrogen atom to which they bind to represent a saturated nitrogen-containing cycloalkyl group or morpholino group.

Rz has the same meaning as Rx, or Rz represents methyl group, ethyl group, or -A$^5$-Re. Ry represents hydrogen atom, an alkyl group having 1 to 8 carbon atoms, or -A$^6$-Qp, or Ry may bind to Rz to form, together with a nitrogen atom to which they bind, a saturated or unsaturated 3 to 7-membered nitrogen-containing cyclic substituent, wherein said nitrogen-containing cyclic substituent may optionally be substituted with one or two lower alkyl groups having 1 to 4 carbon atoms wherein said two alkyl groups may be the same or different. Qp represents phenyl group, and this phenyl group may be substituted with one of $T^1$ or two or more of the same or different $T^1$.

AR represents a partially unsaturated or completely unsaturated condensed bicyclic carbon ring or a heterocyclic ring (ar), and may be substituted with one of Xa or two or more of the same or different Xa. The heterocyclic ring (ar) contains the same or different 1 to 4 ring-constituting heteroatoms selected from the group consisting of nitrogen atom, oxygen atom, and sulfur atom. Xa represents a linear or branched saturated alkyl group having 1 to 4 carbon atoms, a saturated cyclic alkyl group having 3 to 7 carbon atoms, oxo group, thioxo group, fluorine atom, chlorine atom, trifluoromethyl group, —(CH$_2$)$_i$R$^{14}$, —OR$^{10}$, —N(R$^{11}$)(R$^{12}$), —SO$_2$R$^{13}$, or —COR$^{27}$. $R^{10}$ represents hydrogen atom, a lower alkyl group having 1 to 4 carbon atoms, or —(CH$_2$)$_i$R$^{14}$. $R^{11}$ represents hydrogen atom or a lower alkyl group having 1 to 4 carbon atoms. $R^{12}$ represents hydrogen atom, a lower alkyl group having 1 to 4 carbon atoms, a hydroxyalkyl group having 2 to 4 carbon atoms, —COR$^{15}$, or —SO$_2$R$^{16}$, or binds to $R^{11}$ to form a 3- to 6-membered ring together with the nitrogen atom to which they bind to represent a saturated nitrogen-containing cycloalkyl group or morpholino group. $R^{15}$ represents a lower alkyl group having 1 to 4 carbon atoms, a hydroxyalkyl group having 2 to 4 carbon atoms, amino group, a mono- or dialkylamino group having 1 to 4 carbon atoms, or -A$^6$-Qa. $R^{13}$ and $R^{16}$ independently represent a lower alkyl group having 1 to 4 carbon atoms, amino group, or a mono- or dialkylamino group having 1 to 4 carbon atoms. $R^{27}$ represents hydrogen atom, hydroxyl group, an alkoxy group having 1 to 4 carbon atoms, a lower alkyl group having 1 to 4 carbon atoms, amino group, or a mono- or dialkylamino group having 1 to 4 carbon atoms.

Y represents hydrogen atom, a lower alkyl group having 1 to 4 carbon atoms, —(CH$_2$)$_m$N(R$^{18}$)(R$^{19}$), or —C(R$^{20}$)$_2$OC(O)A$^3$R$^{21}$. Symbol m represents an integer of 2 or 3. $R^{18}$ is the same as $R^{19}$, or binds to $R^{19}$ to form a 3- to 6-membered ring together with the nitrogen atom to which they bind to represent a saturated nitrogen-containing cycloalkyl group or morpholino group. $R^{19}$ represents methyl group, ethyl group, or propyl group. $R^{20}$ represents hydrogen atom, methyl group, ethyl group, or propyl group. $R^{21}$ represents a lower alkyl group having 1 to 4 carbon atoms, a cyclic saturated alkyl group having 3 to 6 carbon atoms, or phenyl group, and $A^3$ represents a single bond, or oxygen atom] or a salt thereof as an active ingredient, and a pharmaceutically acceptable carrier, wherein the composition does not substantially contain any reducing sugar and/or carrier containing a reducing sugar as an ingredient as the pharmaceutically acceptable carrier, or when the composition contains a reducing sugar and/or a carrier containing a reducing sugar as an ingredient as the pharmaceutically acceptable carrier, contact of the reducing sugar and the compound represented by the general formula (I) or a salt thereof is eliminated.

[B1-2] The pharmaceutical composition according to [1] mentioned above (except for a pharmaceutical composition comprising only methylcellulose as the pharmaceutically acceptable carrier, and a pharmaceutical composition comprising only carboxymethylcellulose as the pharmaceutically acceptable carrier).

[B1-3] The pharmaceutical composition according to [1] mentioned above (except for a pharmaceutical composition comprising only methylcellulose as the pharmaceutically acceptable carrier, a pharmaceutical composition comprising only methylcellulose and water as the pharmaceutically acceptable carrier, a pharmaceutical composition comprising only carboxymethylcellulose as the pharmaceutically acceptable carrier, and a pharmaceutical composition comprising only carboxymethylcellulose and water as the pharmaceutically acceptable carrier).

[B2] The pharmaceutical composition according to any one of [B1] to [B1-3] mentioned above, which does not substantially contain any reducing sugar and/or carrier containing a reducing sugar as an ingredient as the pharmaceutically acceptable carrier.

[B2-2] The pharmaceutical composition according to any one of [B1] to [B1-3] mentioned above, which contains a reducing sugar as the pharmaceutically acceptable carrier, but comprises a means for eliminating contact of the compound represented by the general formula (I) or a salt thereof and the reducing sugar.

[B3] The pharmaceutical composition according to any one of [B1] to [B2-2] mentioned above, wherein the pharmaceutical composition is a pharmaceutical composition in a dry form.

[B3-2] The pharmaceutical composition according to any one of [B1] to [B2-2] mentioned above, wherein the pharmaceutically acceptable carrier is a dry carrier.

[B4] The pharmaceutical composition according to any one of [B1] to [B3-2] mentioned above, which does not contain a reducing sugar selected from the group consisting of fructose, xylose, lactose, glucose, maltose, and maltitol and/or carrier containing such a reducing sugar as an ingredient as the pharmaceutically acceptable carrier.

[B4-2] The pharmaceutical composition according to any one of [B1] to [B3-2] mentioned above, which does not substantially contain any reducing sugar which gives a difference of 50 mV or less between oxidation reduction potential of a 0.1 moL/L aqueous solution of the reducing sugar and oxidation reduction potential of water used for dissolving the reducing sugar and/or carrier containing such a reducing sugar as an ingredient as the pharmaceutically acceptable carrier.

[B5] The pharmaceutical composition according to any one of [B1] to [B4-2] mentioned above, wherein the pharmaceutically acceptable carrier consists of one or more kinds of carriers selected from the group consisting of cellulose derivatives, starches, starch derivatives, synthetic polymer compounds, non-reducing sugars, polyhydric alcohols, fatty acid derivatives, and inorganic substances.

[B5-2] The pharmaceutical composition according to any one of [B1] to [B4-2] mentioned above, wherein the pharmaceutically acceptable carrier consists of one or more kinds of carriers selected from the group consisting of crystalline cellulose, mannitol, methylcellulose, croscarmellose sodium, corn starch, anhydrous calcium hydrogenphosphate, hydroxypropylcellulose, crospovidone, povidone, sucrose, sodium carboxymethyl starch, low substituted hydroxypropylcellulose, partially pregelatinized starch, hydroxypropylmethylcellulose, erythritol, carmellose, polyvinyl alcohol, trehalose, carmellose calcium, magnesium stearate, and carmellose sodium.

[B5-3] The pharmaceutical composition according to any one of [B1] to [B4-2] mentioned above, wherein the pharmaceutically acceptable carrier consists of one or more kinds of carriers selected from the group consisting of crystalline cellulose, mannitol, croscarmellose sodium, corn starch, anhydrous calcium hydrogenphosphate, sucrose, povidone, sodium carboxymethyl starch, low substituted hydroxypropylcellulose, partially pregelatinized starch, hydroxypropylmethylcellulose, erythritol, polyvinyl alcohol, magnesium stearate, and carmellose calcium.

[B5-4] The pharmaceutical composition according to any one of [B1] to [B4-2] mentioned above, wherein the pharmaceutically acceptable carrier consists of one or more kinds of carriers selected from the group consisting of crystalline cellulose, mannitol, croscarmellose sodium, corn starch, anhydrous calcium hydrogenphosphate, sucrose, sodium carboxymethyl starch, low substituted hydroxypropylcellulose, partially pregelatinized starch, hydroxypropylmethylcellulose, erythritol, polyvinyl alcohol, and carmellose calcium.

[B6] The pharmaceutical composition according to any one of [B1] to [B5-4] mentioned above, wherein, in the formula (I), Link is $—(CH_2)_n—$, n is an integer of 1 to 3, Rz has the same meaning as that of Rx or represents -$A^5$-Re when Rs is $—N(Ry)(Rz)$, and Ry is hydrogen atom, an alkyl group having 1 to 8 carbon atoms, or -$A^6$-Qp, or Ry binds to Rz to form, together with a nitrogen atom to which they bind, a saturated or unsaturated nitrogen-containing cyclic substituent having 3 to 7 atoms.

[B7] The pharmaceutical composition according to [B6] mentioned above, wherein, in the formula (I), AR is a residue of naphthalene, benzofuran, benzo[b]thiophene, indole, benzothiazole, dihydro-3H-benzothiazole, quinoline, dihydro-1H-quinoline, benzo[d]isothiazole, 1H-indazole, benzo[c]isothiazole, 2H-indazole, imidazo[1,2-a]pyridine, 1H-pyrrolo[2,3-b]pyridine, isoquinoline, dihydro-2H-isoquinoline, cinnoline, quinazoline, quinoxaline, 1H-benzimidazole, benzoxazole, 1H-pyrrolo[3,2-b]pyridine, benzo[1,2,5]thiadiazole, 1H-benzotriazole, 1,3-dihydropyrrolo[2,3-b]pyridine, 1,3-dihydrobenzimidazole, dihydro-3H-benzoxazole, phthalazine, [1,8]naphthylidine, [1,5]naphthylidine, 1H-pyrrolo[3,2-c]pyridine, 1H-pyrrolo[2,3-c]pyridine, 1H-pyrazolo[4,3-b]pyridine, 1H-pyrazolo[4,3-c]pyridine, 1H-pyrazolo[3,4-c]pyridine, 1H-pyrazolo[3,4-b]pyridine, [1,2,4]triazolo[4,3-a]pyridine, thieno[3,2-c]pyridine, thieno[3,2-b]pyridine, 1H-thieno[3,2-c]pyrazole, benzo[d]isoxazole, benzo[c]isoxazole, indolizine, 1,3-dihydroindole, 1H-pyrazolo[3,4-d]thiazole, 2H-isoindole, [1,2,4]triazolo[1,5-a]pyrimidine, 1H-pyrazolo[3,4-b]pyrazine, 1H-imidazo[4,5-b]pyrazine, 7H-purine, or 4H-chromene (the aforementioned residue may be substituted with one of Xa or two or more of the same or different Xa).

[B8] The pharmaceutical composition according to [B6] mentioned above wherein, in the formula (I), AR is naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthylidin-3-yl group, [1,8]naphthylidin-4-yl group, [1,5]naphthylidin-3-yl group, [1,5]naphthylidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-6-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizin-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, or 4H-chromen-5-yl group (the aforementioned groups may be substituted with one of Xa or two or more of the same or different Xa).

[B9] The pharmaceutical composition according to any one of [B6] to [B8] mentioned above, wherein, in the formula (I), Rs is -D-Rx or —N(Ry)(Rz), D is a single bond, oxygen atom, sulfur atom, —S(O)—, —S(O)$_2$—, or —C(O)—, Rx is a linear or branched saturated alkyl group having 3 to 8 carbon atoms, or Ra, Rb, or Rc, k in Ra is 0 or an integer of 1 to 3, $R^1$ is a saturated cycloalkyl group having 3 to 7 carbon atoms or a condensed saturated cycloalkyl group having 6 to 8 carbon atoms, $R^1$ may be substituted with one of lower alkyl group having 1 to 4 carbon atoms or two or more of the same or different lower alkyl groups having 1 to 4 carbon atoms, Q in Rb is phenyl group, thienyl group, furyl group, pyrrolyl group, pyridyl group, oxazolyl group, isoxazolyl group, thiazolyl group, isothiazolyl group, imidazolyl group, pyrazolyl group, oxadiazolyl group, thiadiazolyl group, triazolyl group, tetrazolyl group, naphthyl group, tetrahydronaphthyl group, indanyl group, indenyl group, quinolyl group, isoquinolyl group, indolyl group, benzofuryl group, benzothienyl group, benzimidazolyl group, benzoxazolyl group, benzothiazolyl group, indazolyl group, 4H-chromenyl group, dihydrobenzodioxyl group, benzoisoxazolyl group, pyrrolopyridinyl group, pyrazolopyridinyl group, triazolopyridinyl group, thienopyridinyl group, thienopyrazolyl group, 1,3-dihydrobenzimidazole group, dihydro-3H-benzoxazole group, or dihydro-3H-benzothiazole group (the aforementioned groups binds to $A^2$ at an arbitrary position), $A^1$ is a single bond or an alkylene (a) having 1 to 3 carbon atoms, the alkylene (a) may be substituted with a lower alkyl group having 1 to 4 carbon atoms or phenyl group, $A^2$ is a single bond, oxygen atom, sulfur atom, —S(O)—, —S(O)$_2$—, or —N($R^4$)— (provided that when $A^2$ represents oxygen atom, sulfur atom, —S(O)—, —S(O)$_2$—, or —N($R^4$)—, $A^1$ represents ethylene or trimethylene), $R^2$ and $R^3$ independently represent hydrogen atom, a linear or branched saturated alkyl group having 1 to 4 carbon atoms, oxo group, thioxo group, fluorine atom, chlorine atom, bromine atom, trifluoromethyl group, —$OR^6$, —N($R^6$)($R^{6'}$), —NHCO$R^7$, —NHSO$_2R^8$, or -$A^6$-Qa, or they bind to each other to represent methylenedioxy group, Qa is phenyl group, pyridyl group, oxazolyl group, isoxazolyl group, thiazolyl group, isothiazolyl group, imidazolyl group, pyrazolyl group, oxadiazolyl group, thiadiazolyl group, triazolyl group, tetrazolyl group, naphthyl group, indanyl group, indenyl group, quinolyl group, isoquinolyl group, indolyl group, benzofuryl group, benzothienyl group, benzimidazolyl group, benzoxazolyl group, benzothiazolyl group, or indazolyl group (these groups may be substituted with one of $T^1$ or two or more of the same or different $T^1$, and bind to $A^6$ at an arbitrary position on the ring), $R^4$ and $R^6$ independently represent hydrogen atom or a lower alkyl group having 1 to 4 carbon atoms, $R^5$ and $R^7$ independently represent hydrogen atom, a lower alkyl group having 1 to 4 carbon atoms, or -$A^6$-Qa, $R^8$ is a lower alkyl group having 1 to 4 carbon atoms, $R^{6'}$ has the same meaning as $R^6$, or binds to $R^6$ to form a 3- to 6-membered ring together with the nitrogen atom to which they bind to form a saturated nitrogen-containing cycloalkyl group or morpholino group, p in Rc is an integer of 2 to 4, $A^4$ is a single bond or methylene or ethylene, A5 is —C(O)—, —C(S)—, or —S(O)$_2$—, Rd is hydrogen atom, an alkyl group having 1 to 8 carbon atoms, or Qa, Re is an alkyl group having 1 to 8 carbon atoms, -$A^6$-Qa, —(CH$_2$)$_iR^{14}$, —$OR^{28}$, —$SR^{28}$, or —N($R^{29}$)($R^{30}$), i is an integer of 1 to 3, $R^{14}$ is hydroxyl group, an alkoxy group having 1 to 4 carbon atoms, carboxyl group, or an N,N-dialkylcarbamoyl group having 1 to 4 carbon atoms, $R^{28}$ is an alkyl group having 1 to 8 carbon atoms or -$A^6$-Qa, $R^{29}$ is an alkyl group having 1 to 8 carbon atoms, an alkoxycarbonyl group having 1 to 4 carbon atoms, or -$A^6$-Qa, $R^{30}$ is hydrogen atom or a lower alkyl group having 1 to 4 carbon atoms, or binds to $R^{29}$ to form a 3- to 6-membered ring together with the nitrogen atom to which they bind to form a saturated nitrogen-containing cycloalkyl group or morpholino group, Rz has the same meaning as Rx, or is -$A^5$-Re, and Ry is hydrogen atom, an alkyl group having 1 to 8 carbon atoms, or -$A^6$-Qp, or binds to Rz to form a saturated or unsaturated nitrogen-containing cyclic substituent having 3 to 7 atoms together with nitrogen atom to which they binds.

[B10] The pharmaceutical composition according to any one of [B6] to [B9] mentioned above, wherein, in the general formula (I), Rs is —O-Rx.

[B1] The pharmaceutical composition according to [B6] mentioned above, wherein, in the formula (I), AR binds at the position of $C^3$ in the aromatic ring (E), and Rs binds to one of the ring-constituting carbon atoms $C^4$, $C^5$, and $C^6$.

[B12] The pharmaceutical composition according to [B6] mentioned above, wherein, in the formula (I), AR binds at the position of $C^2$ in the aromatic ring (E), and Rs binds to one of ring-constituting carbon atoms $C^3$, $C^4$ and $C^5$.

[B131] The pharmaceutical composition according to [B12] mentioned above, wherein, in the general formula (I), n is an integer of 2, and Y is hydrogen atom or a lower alkyl group having 1 to 4 carbon atoms.

[B14] The pharmaceutical composition according to [B11] mentioned above, wherein, in the general formula (I), Rs binds to one of ring-constituting carbon atoms $C^5$ and $C^6$ in the aromatic ring (E).

[B15] The pharmaceutical composition according to [B11] mentioned above, wherein, in the general formula (I), Rs binds to $C^4$ in the aromatic ring (E), and $C^5$ is a carbon atom substituted with amino group.

[B16] The pharmaceutical composition according to [B15] mentioned above, wherein, in the general formula (I), n is an integer of 2, D is oxygen atom, and Y is hydrogen atom or a lower alkyl group having 1 to 4 carbon atoms.

[B17] The pharmaceutical composition according to [B11] mentioned above, wherein, in the general formula (I), Rs binds to $C^4$ in the aromatic ring (E), $C^5$ is a carbon atom substituted with amino group, $C^2$ and $C^6$ are unsubstituted ring-constituting carbon atoms, and Rs is —N(Ry)(Rz).

[B18] The pharmaceutical composition according to any one of [B11] to [B5] mentioned above, wherein, in the general formula (I), Link is —(CH$_2$)$_n$—, n is an integer of 1 to 3, $C^2$ and $C^6$ in the aromatic ring (E) are unsubstituted ring-constituting carbon atoms, AR binds at the position of $C^3$ in the aromatic ring (E), and Rs is —N(Ry)(Rz), and binds at the position of $C^4$ in the aromatic ring (E).

[B19] The pharmaceutical composition according to [B18] mentioned above, wherein, in the general formula (I), n is an integer of 2, and $C^6$ is a carbon atom substituted with amino group.

[B20] The pharmaceutical composition according to [B11] mentioned above, wherein, in the general formula (I), Rs binds to $C^4$ in the aromatic ring (E), $C^5$ is a carbon atom substituted with amino group, $C^2$ and $C^6$ are unsubstituted ring-constituting carbon atoms, Rs is -D-Rx, and D is a single bond, sulfur atom, —S(O)—, —S(O)$_2$—, or —C(O)—.

[B21] The pharmaceutical composition according to [B11] mentioned above, wherein, in the general formula (I), n is an integer of 2, Rs binds to $C^4$ in the aromatic ring (E), $C^5$ is a carbon atom substituted with amino group, $C^2$ and $C^6$ are unsubstituted ring-constituting carbon atoms, Rs is —O-Rx, and Y is hydrogen atom or a lower alkyl group having 1 to 4 carbon atoms.

[B22] The pharmaceutical composition according to [B11] mentioned above, wherein, in the general formula (I), n is an integer of 2, Rs binds to $C^4$ in the aromatic ring (E), $C^5$ is a carbon atom substituted with amino group, $C^2$ and $C^6$ are unsubstituted ring-constituting carbon atoms, Rs is —O-Rc, and Y is hydrogen atom or a lower alkyl group having 1 to 4 carbon atoms.

[B23] The pharmaceutical composition according to [B6] mentioned above, wherein, in the general formula (I), AR binds at the position of $C^3$ in the aromatic ring (E), Rs binds at the position of $C^4$ in the aromatic ring (E), $C^5$ is a carbon atom substituted with amino group, Rs is -D-Rx, D is oxygen atom, Rx is a linear or branched saturated alkyl group having 3 to 8 carbon atoms, or Ra or Rb, k in Ra is 0 or an integer of 1 to 3, $R^1$ is a saturated cycloalkyl group having 3 to 7 carbon atoms or a condensed saturated cycloalkyl group having 6 to 8 carbon atoms, $R^1$ may be substituted with one of lower alkyl group having 1 to 4 carbon atoms or two or more of the same or different lower alkyl groups having 1 to 4 carbon atoms, Q in Rb is a partially unsaturated or completely unsaturated monocyclic or condensed bicyclic carbon ring or a heterocyclic ring (q) (Q binds to $A^2$ at an arbitrary position on the ring), $A^1$ is a single bond or an alkylene (a) having 1 to 3 carbon atoms, the alkylene (a) may be substituted with a lower alkyl group having 1 to 4 carbon atoms or phenyl group, $A^2$ is a single bond, oxygen atom, sulfur atom, —S(O)—, —S(O)$_2$—, or —N(R$^4$)— (provided that when $A^2$ represents oxygen atom, sulfur atom, —S(O)—, —S(O)$_2$—, or —N(R$^4$)—, $A^1$ is ethylene or trimethylene), $R^2$ and $R^3$ independently represent hydrogen atom, a linear or branched saturated alkyl group having 1 to 4 carbon atoms, fluorine atom, chlorine atom, bromine atom, trifluoromethyl group, —OR$^5$, —N(R$^6$)(R$^{6'}$), —NHCOR$^7$, —NHSO$_2$R$^8$, or -A$^6$-Qa, or they bind to each other to form methylenedioxy group, Qa is a partially unsaturated or completely unsaturated monocyclic or condensed bicyclic carbon ring or a heterocyclic ring (qa) (Qa may be substituted with one of T$^1$ or two or more of the same or different T$^1$, and binds to A$^6$ at an arbitrary position on the ring), R$^4$, R$^6$ and R$^7$ independently represent hydrogen atom or a lower alkyl group having 1 to 4 carbon atoms, R$^5$ and Rs are lower alkyl groups having 1 to 4 carbon atoms, and R$^{6'}$ has the same meaning as that of R$^6$, or binds to R$^6$ to form a 3- to 6-membered ring together with the nitrogen atom to which they bind to form a saturated nitrogen-containing cycloalkyl group or morpholino group.

[B24] The pharmaceutical composition according to [B23] mentioned above, wherein, in the general formula (I), AR is a residue of naphthalene, benzofuran, benzo[b]thiophene, indole, benzothiazole, dihydro-3H-benzothiazole, quinoline, dihydro-1H-quinoline, benzo[d]isothiazole, 1H-indazole, benzo[c]isothiazole, 2H-indazole, imidazo[1,2-a]pyridine, 1H-pyrrolo[2,3-b]pyridine, isoquinoline, dihydro-2H-isoquinoline, cinnoline, quinazoline, quinoxaline, 1H-benzimidazole, benzoxazole, 1H-pyrrolo[3,2-b]pyridine, benzo[1,2,5]thiadiazole, 1H-benzotriazole, 1,3-dihydropyrrolo[2,3-b]pyridine, 1,3-dihydrobenzimidazole, dihydro-3H-benzoxazole, phthalazine, [1,8]naphthylidine, [1,5]naphthylidine, 1H-pyrrolo[3,2-c]pyridine, 1H-pyrrolo[2,3-c]pyridine, 1H-pyrazolo[4,3-b]pyridine, 1H-pyrazolo[4,3-c]pyridine, 1H-pyrazolo[3,4-c]pyridine, 1H-pyrazolo[3,4-b]pyridine, [1,2,4]triazolo[4,3-a]pyridine, thieno[3,2-c]pyridine, thieno[3,2-b]pyridine, 1H-thieno[3,2-c]pyrazole, benzo[d]isoxazole, benzo[c]isoxazole, indolizine, 1,3-dihydroindole, 1H-pyrazolo[3,4-d]thiazole, 2H-isoindole, [1,2,4]triazolo[1,5-a]pyrimidine, 1H-pyrazolo[3,4-b]pyrazine, 1H-imidazo[4,5-b]pyrazine, 7H-purine, or 4H-chromene (the aforementioned residue may be substituted with one of Xa or two or more of the same or different Xa).

[B25] The pharmaceutical composition according to [B23] mentioned above, wherein, in the general formula (I), AR is naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthylidin-3-yl group, [1,8]naphthylidin-4-yl group, [1,5]naphthylidin-3-yl group, [1,5]naphthylidin-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizin-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, or 4H-chromen-5-yl group (the aforementioned groups may be substituted with one of Xa or two or more of the same or different Xa).

[B26] The pharmaceutical composition according to [B24] or [B25] mentioned above, wherein, in the general formula (I), Rx is a linear or branched saturated alkyl group having 3 to 8 carbon atoms, or Ra, $R^1$ is a saturated cycloalkyl group having 3 to 7 carbon atoms or a condensed saturated cycloalkyl group having 6 to 8 carbon atoms, and $R^1$ is a group which may be substituted with one of lower alkyl group having 1 to 4 carbon atoms or two or more of the same or different lower alkyl groups having 1 to 4 carbon atoms.

[B27] The pharmaceutical composition according to [B24] or [B25] mentioned above, wherein, in the general formula (I), Rx is Rb; Q in Rb is phenyl group or indanyl group; when Q is phenyl group, $A^1$ is a single bond or unsubstituted methylene, and when $A^2$ is a single bond, one of $R^2$ and $R^3$ is a substituent other than hydrogen atom.

[B28] The pharmaceutical composition according to [B23] mentioned above, wherein, in the general formula (I), n is an integer of 2; Rx is butyl group, isobutyl group, 2-ethylbutyl group, cyclopentyl group, cyclohexyl group, cyclopentylmethyl group, or cyclohexylmethyl group, or the substituent Rb, provided that the group Q in Rb is phenyl group or indanyl group; $A^1$ is a single bond, a methylene group substituted with 1 to 3 methyl groups or ethyl groups or unsubstituted methylene group, or an ethylene group substituted with 1 to 3 methyl groups or ethyl groups or unsubstituted ethylene group; $A^2$ is a single bond; $R^2$ and $R^3$ are both hydrogen atoms, or independently methyl group, fluorine atom, chlorine atom, trifluoromethyl group, methoxy group, or dimethylamino group, provided that when Q is phenyl group, $A^1$ is a single bond, or unsubstituted methylene, one of $R^2$ and $R^3$ is a substituent other than hydrogen atom; the substituent AR is naphthalen-2-yl group, benzofuran-5-yl group, benzo[b]thiophen-5-yl group, indol-5-yl group, benzothiazol-6-yl group, quinolin-6-yl group, quinolin-3-yl group, isoquinolin-6-yl group, or 1H-indazol-5-yl group (the aforementioned residue may be substituted with one of Xa or two or more of the same or different Xa, and Xa represents a linear or branched saturated alkyl group having 1 to 4 carbon atoms); and Y is hydrogen atom, methyl group or ethyl group.

[B29] The pharmaceutical composition according to [B23] mentioned above, wherein, in the general formula (I), n is an integer of 2; Rx is butyl group, isobutyl group, 2-ethylbutyl group, cyclopentyl group, cyclohexyl group, cyclopentylmethyl group, or cyclohexylmethyl group, or the substituent Rb, provided that Q in the group Rb is phenyl group; $A^1$ is a single bond, a methylene group substituted with 1 to 3 methyl groups or ethyl groups or unsubstituted methylene group, or an ethylene group substituted with 1 to 3 methyl groups or ethyl groups or unsubstituted ethylene group; $A^2$ is a single bond; $R^2$ and $R^3$ are both hydrogen atoms, or independently represent methyl group, fluorine atom, chlorine atom, trifluoromethyl group, methoxy group, or dimethylamino group, provided that $A^1$ is a single bond, or unsubstituted methylene, one of $R^2$ and $R^3$ is a substituent other than hydrogen atom; the substituent AR is naphthalen-2-yl group, benzofuran-5-yl group, benzo[b]thiophen-5-yl group, indol-5-yl group, benzothiazol-6-yl group, quinolin-6-yl group, quinolin-3-yl group, isoquinolin-6-yl group, or 1H-indazol-5-yl group (the aforementioned residue may be substituted with one of Xa or two or more of the same or different Xa, and Xa represents a linear or branched saturated alkyl group having 1 to 4 carbon atoms); and Y is hydrogen atom, methyl group or ethyl group.

[B30] The pharmaceutical composition according to [B23] mentioned above, wherein, in the general formula (I), n is an integer of 2; Rx is butyl group, isobutyl group, 2-ethylbutyl group, cyclopentyl group, cyclohexyl group, cyclopentylmethyl group, or cyclohexylmethyl group, or the substituent Rb, provided that Q in the group Rb is indan-2-yl group; $A^1$ is a single bond, a methylene group substituted with 1 to 3 methyl groups or ethyl groups or unsubstituted methylene group, or an ethylene group substituted with 1 to 3 methyl groups or ethyl groups or unsubstituted ethylene group; $A^2$ is a single bond; $R^2$ and $R^3$ are both hydrogen atoms, or independently represent methyl group, fluorine atom, chlorine atom, trifluoromethyl group, methoxy group, or dimethylamino group; the substituent AR is naphthalen-2-yl group, benzofuran-5-yl group, benzo[b]thiophen-5-yl group, indol-5-yl group, benzothiazol-6-yl group, quinolin-6-yl group, quinolin-3-yl group, isoquinolin-6-yl group, or 1H-indazol-5-yl group (the aforementioned residue may be substituted with one of Xa or two or more of the same or different Xa, and Xa represents a linear or branched saturated alkyl group having 1 to 4 carbon atoms); and Y is hydrogen atom, methyl group or ethyl group.

[B31] The pharmaceutical composition according to any one of [B1] to [B30] mentioned above, wherein the compound represented by the general formula (I) or a salt thereof is any one of 3-[3-amino-4-(indan-2-yloxy)-5-(1-methyl-1H-indazol-5-yl)phenyl]propionic acid, 3-{3-amino-4-[2-(4-methylphenyl)ethyloxy]-5-(naphthalen-2-yl)phenyl}propionic acid, 3-[3-amino-4-cyclopentylmethyloxy-5-(1H-indol-5-yl)phenyl]propionic acid, 3-[3-amino-4-cyclopentylmethyloxy-5-(1-methyl-1H-indol-5-yl)phenyl]propionic acid, and 3-[3-amino-4-(indan-2-yloxy)-5-(1H-indazol-5-yl)phenyl]propionic acid.

[B32] The pharmaceutical composition according to any one of [B1] to [B30] mentioned above, wherein the compound represented by the general formula (I) or a salt thereof is 3-[3-amino-4-(indan-2-yloxy)-5-(1-methyl-1H-indazol-5-yl)phenyl]propionic acid.

[B33] The pharmaceutical composition according to any one of [B1] to [B32] mentioned above, which is in the form of a solid preparation.

[B34] A method for preparing a pharmaceutical composition comprising a compound represented by the general formula (I) or a salt thereof according to [1] mentioned above as an active ingredient, and a pharmaceutically acceptable carrier, which comprises the step of preparing the pharmaceutical composition by using a carrier other than a reducing sugar and/or a carrier containing a reducing sugar as an ingredient as the pharmaceutically acceptable carrier, or when a reducing sugar and/or a carrier containing a reducing sugar as an ingredient is used as the pharmaceutically acceptable carrier, with eliminating contact of the reducing sugar and the compound represented by the general formula (I) or a salt thereof.

[B34-2] A method for preparing the pharmaceutical composition according to [B1-2] mentioned above, which comprises the step of preparing the pharmaceutical composition by using a carrier other than a reducing sugar and/or a carrier containing a reducing sugar as an ingredient as the pharmaceutically acceptable carrier, or when a reducing sugar and/or a carrier containing a reducing sugar as an ingredient is used as the pharmaceutically acceptable carrier, with eliminating contact of the reducing sugar and the compound represented by the general formula (I) or a salt thereof.

[B34-3] A method for preparing the pharmaceutical composition according to [B1-3] mentioned above, which comprises the step of preparing the pharmaceutical composition by using a carrier other than a reducing sugar and/or a carrier containing a reducing sugar as an ingredient as the pharmaceutically acceptable carrier, or when a reducing sugar and/or a carrier containing a reducing sugar as an ingredient is used as the pharmaceutically acceptable carrier, with eliminating contact of the reducing sugar and the compound represented by the general formula (I) or a salt thereof.

[B35] The preparation method according to any one of [B34] to [B34-3] mentioned above, which comprises the step of preparing the pharmaceutical composition by using a carrier other than a reducing sugar and/or a carrier containing a reducing sugar as an ingredient.

[B35-2] The preparation method according to any one of [B34] to [B34-3] mentioned above, which comprises the step of preparing the pharmaceutical composition by using a reducing sugar and/or a carrier containing a reducing sugar as an ingredient, with eliminating contact of the reducing sugar and the compound represented by the general formula (I) or a salt thereof.

[B36] The preparation method according to any one of [B34] to [B35-2] mentioned above, wherein the pharmaceutical composition is a pharmaceutical composition in a dry form.

[B36-2] The preparation method according to any one of [B34] to [B35-2] mentioned above, wherein the pharmaceutically acceptable carrier is a dry carrier.

[B37] The method according to any one of [B34] to [B36-2] mentioned above, which does not use a reducing sugar selected from the group consisting of fructose, xylose, lactose, glucose, maltose, and maltitol and/or a carrier containing such a reducing sugar as an ingredient as the pharmaceutically acceptable carrier.

[B38] The preparation method according to any one of [B34] to [B37] mentioned above, wherein the pharmaceutically acceptable carrier consists of one or more kinds of carriers selected from the group consisting of cellulose derivatives, starches, starch derivatives, synthetic polymer compounds, non-reducing sugar, polyhydric alcohols, fatty acid derivatives, and inorganic substances.

[B38-2] The preparation method according to any one of [B34] to [B37] mentioned above, wherein the pharmaceutically acceptable carrier consists of one or more kinds of carriers selected from the group consisting of crystalline cellulose, mannitol, methylcellulose, croscarmellose sodium, corn starch, anhydrous calcium hydrogenphosphate, hydroxypropylcellulose, crospovidone, sucrose, povidone, sodium carboxymethyl starch, low substituted hydroxypropylcellulose, partially pregelatinized starch, hydroxypropylmethylcellulose, erythritol, carmellose, polyvinyl alcohol, trehalose, carmellose calcium, magnesium stearate, and carmellose sodium.

[B39] The preparation method according to any one of [B34] to [B38-2] mentioned above, wherein the compound represented by the general formula (I) or a salt thereof is the compound or a salt thereof according to any one of [B6] to [B32] mentioned above.

[B40] A method for stabilizing a pharmaceutical composition comprising a compound represented by the general formula (I) or a salt thereof according to [1] mentioned above as an active ingredient, and a pharmaceutically acceptable carrier, which comprises the step of preparing the pharmaceutical composition by using a carrier other than a reducing sugar and/or a carrier containing a reducing sugar as an ingredient as the pharmaceutically acceptable carrier, or when a reducing sugar and/or a carrier containing a reducing sugar as an ingredient is used as the pharmaceutically acceptable carrier, with eliminating contact of the reducing sugar and the compound represented by the general formula (I) or a salt thereof.

[B40-2] A method for stabilizing the pharmaceutical composition according to [B1-2] mentioned above, which comprises the step of preparing the pharmaceutical composition by using a carrier other than a reducing sugar and/or a carrier containing a reducing sugar as an ingredient as the pharmaceutically acceptable carrier, or when a reducing sugar and/or a carrier containing a reducing sugar as an ingredient is used as the pharmaceutically acceptable carrier, with eliminating contact of the reducing sugar and the compound represented by the general formula (I) or a salt thereof.

[B40-3] A method for stabilizing the pharmaceutical composition according to [B1-3] mentioned above, which comprises the step of preparing the pharmaceutical composition by using a carrier other than a reducing sugar and/or a carrier containing a reducing sugar as an ingredient as the pharmaceutically acceptable carrier, or when a reducing sugar and/or a carrier containing a reducing sugar as an ingredient is used as the pharmaceutically acceptable carrier, with eliminating contact of the reducing sugar and the compound represented by the general formula (I) or a salt thereof.

[B41] The stabilization method according to any one of [B40] to [B40-3] mentioned above, which comprises the step of preparing the pharmaceutical composition by using a carrier other than a reducing sugar and/or a carrier containing a reducing sugar as an ingredient.

[B41-2] The stabilization method according to any one of [B40] to [B40-3] mentioned above, which comprises the step of preparing the pharmaceutical composition by using a reducing sugar and/or a carrier containing a reducing sugar as an ingredient, with eliminating contact of the reducing sugar and the compound represented by the general formula (I) or a salt thereof.

[B42] The stabilization method according to any one of [B40] to [B41-2] mentioned above, wherein the pharmaceutical composition is a pharmaceutical composition in a dry form.

[B42-2] The stabilization method according to any one of [B40] to [B41-2] mentioned above, wherein the pharmaceutically acceptable carrier is a dry carrier.

[B43] The stabilization method according to any one of [B40] to [B42-2] mentioned above, wherein the pharmaceutical composition is prepared by using a carrier other than a reducing sugar selected from the group consisting of fructose, xylose, lactose, glucose, maltose, and maltitol and/or a carrier containing such a reducing sugar as an ingredient as the pharmaceutically acceptable carrier.

[B44] The stabilization method according to any one of [B40] to [B43] mentioned above, wherein the pharmaceutically acceptable carrier consists of one or more kinds of carriers selected from the group consisting of cellulose derivatives, starches, starch derivatives, synthetic polymer compounds, non-reducing sugar, polyhydric alcohols, fatty acid derivatives, and inorganic substances.

[B44-2] The stabilization method according to any one of [B40] to [B43] mentioned above, wherein the pharmaceutically acceptable carrier consists of one or more kinds of carriers selected from the group consisting of crystalline cellulose, mannitol, methylcellulose, croscarmellose sodium, corn starch, anhydrous calcium hydrogenphosphate, hydroxypropylcellulose, crospovidone, sucrose, povidone, sodium carboxymethyl starch, low substituted hydroxypropylcellulose, partially pregelatinized starch, hydroxypropylmethylcellulose, erythritol, carmellose, polyvinyl alcohol, trehalose, carmellose calcium, magnesium stearate, and carmellose sodium.

[B44-3] The stabilization method according to any one of [B40] to [B43] mentioned above, wherein the pharmaceutically acceptable carrier consists of one or more kinds of carriers selected from the group consisting of crystalline cellulose, mannitol, croscarmellose sodium, corn starch, anhydrous calcium hydrogenphosphate, sucrose, povidone, sodium carboxymethyl starch, low substituted hydroxypropylcellulose, partially pregelatinized starch, hydroxypropylmethylcellulose, erythritol, polyvinyl alcohol, magnesium stearate, and carmellose calcium.

[B44-4] The stabilization method according to any one of [B40] to [B43] mentioned above, wherein the pharmaceutically acceptable carrier consists of one or more kinds of carriers selected from the group consisting of crystalline cellulose, mannitol, croscarmellose sodium, corn starch, anhydrous calcium hydrogenphosphate, sucrose, sodium carboxymethyl starch, low substituted hydroxypropylcellulose, partially pregelatinized starch, hydroxypropylmethylcellulose, erythritol, polyvinyl alcohol, and carmellose calcium.

[B45] The stabilization method according to any one of [B40] to [B44-4] mentioned above, wherein the compound represented by the general formula (I) or a salt thereof is the compound or a salt thereof according to any one of [B6] to [B32] mentioned above.

[B46] The stabilization method according to any one of [B40] to [B45] mentioned above, which is performed for prevention of coloring of the compound represented by the general formula (I) or a salt thereof.

[B47] The stabilization method according to any one of [B40] to [B45] mentioned above, which is performed for prevention of decomposition of the compound represented by the general formula (I) or a salt thereof.

[B48] A method for storing and/or distributing a pharmaceutical composition comprising the compound represented by the general formula (I) or a salt thereof according to [1] mentioned above as an active ingredient, and a pharmaceutically acceptable carrier, wherein the pharmaceutical composition is stored and/or distributed after the pharmaceutical composition is prepared by using a carrier other than a reducing sugar and/or a carrier containing a reducing sugar as an ingredient, or when a reducing sugar and/or a carrier containing a reducing sugar as an ingredient is used as the pharmaceutically acceptable carrier, with eliminating contact of the reducing sugar and the compound represented by the general formula (I) or a salt thereof.

[B48-2] The method for storing and/or distributing the pharmaceutical composition according to [B1-2] mentioned above, wherein the pharmaceutical composition is stored and/or distributed after the pharmaceutical composition is prepared by using a carrier other than a reducing sugar and/or a carrier containing a reducing sugar as an ingredient, or when a reducing sugar and/or a carrier containing a reducing sugar as an ingredient is used as the pharmaceutically acceptable carrier, with eliminating contact of the reducing sugar and the compound represented by the general formula (I) or a salt thereof.

[B48-3] The method for storing and/or distributing the pharmaceutical composition according to [B1-3] mentioned above, wherein the pharmaceutical composition is stored and/or distributed after the pharmaceutical composition is prepared by using a carrier other than a reducing sugar and/or a carrier containing a reducing sugar as an ingredient, or when a reducing sugar and/or a carrier containing a reducing sugar as an ingredient is used as the pharmaceutically acceptable carrier, with eliminating contact of the reducing sugar and the compound represented by the general formula (I) or a salt thereof.

[B49] The method according to any one of [B48] to [B48-3] mentioned above, wherein the pharmaceutical composition is stored and/or distributed after the pharmaceutical composition is prepared by using a carrier other than a reducing sugar and/or a carrier containing a reducing sugar as an ingredient.

[B49-2] The method according to any one of [B48] to [B48-3] mentioned above, wherein the pharmaceutical composition is stored and/or distributed after the pharmaceutical composition is prepared by using a reducing sugar and/or a carrier containing a reducing sugar as an ingredient as the pharmaceutically acceptable carrier, with eliminating contact of the reducing sugar and the compound represented by the general formula (I) or a salt thereof.
[B50] The method according to any one of [B48] to [B49-2] mentioned above, wherein the pharmaceutical composition is a pharmaceutical composition in a dry form.
[B50-2] The method according to any one of [B48] to [B49-2] mentioned above, wherein the pharmaceutically acceptable carrier is a dry carrier.
[B51] The method according to any one of [B48] to [B50-2] mentioned above, wherein the pharmaceutical composition prepared by using a carrier other than a reducing sugar selected from the group consisting of fructose, xylose, lactose, glucose, maltose, and maltitol and/or a carrier containing such a reducing sugar as an ingredient as the pharmaceutically acceptable carrier is stored and/or distributed.
[B52] The method according to any one of [B48] to [B51] mentioned above, wherein the pharmaceutically acceptable carrier consists of one or more kinds of carriers selected from the group consisting of cellulose derivatives, starches, starch derivatives, synthetic polymer compounds, non-reducing sugar, polyhydric alcohols, fatty acid derivatives, and inorganic substances.
[B52-2] The method according to any one of [B48] to [B51] mentioned above, wherein the pharmaceutically acceptable carrier consists of one or more kinds of carriers selected from the group consisting of crystalline cellulose, mannitol, methylcellulose, croscarmellose sodium, corn starch, anhydrous calcium hydrogenphosphate, hydroxypropylcellulose, crospovidone, sucrose, povidone, sodium carboxymethyl starch, low substituted hydroxypropylcellulose, partially pregelatinized starch, hydroxypropylmethylcellulose, erythritol, carmellose, polyvinyl alcohol, trehalose, carmellose calcium, magnesium stearate, and carmellose sodium.
[B52-3] The method according to any one of [B48] to [B51] mentioned above, wherein the pharmaceutically acceptable carrier consists of one or more kinds of carriers selected from the group consisting of crystalline cellulose, mannitol, croscarmellose sodium, corn starch, anhydrous calcium hydrogenphosphate, sucrose, povidone, sodium carboxymethyl starch, low substituted hydroxypropylcellulose, partially pregelatinized starch, hydroxypropylmethylcellulose, erythritol, polyvinyl alcohol, magnesium stearate, and carmellose calcium.
[B52-4] The method according to any one of [B48] to [B51] mentioned above, wherein the pharmaceutically acceptable carrier consists of one or more kinds of carriers selected from the group consisting of crystalline cellulose, mannitol, croscarmellose sodium, corn starch, anhydrous calcium hydrogenphosphate, sucrose, sodium carboxymethyl starch, low substituted hydroxypropylcellulose, partially pregelatinized starch, hydroxypropylmethylcellulose, erythritol, polyvinyl alcohol, and carmellose calcium.
[B53] The method according to any one of [B48] to [B52-4] mentioned above, wherein the compound represented by the general formula (I) or a salt thereof is the compound or a salt thereof according to any one of [B6] to [B32] mentioned above.

Effect of the Invention

According to the present invention, a stable pharmaceutical composition comprising a compound represented by the general formula (I) or a salt thereof as an active ingredient is provided. The aforementioned stable pharmaceutical composition provided by the present invention gives reduced or eliminated decomposition or coloring of the active ingredient, and is useful as a pharmaceutical composition which can be stably stored and/or distributed.

BEST MODE FOR CARRYING OUT THE INVENTION

Figure 1:
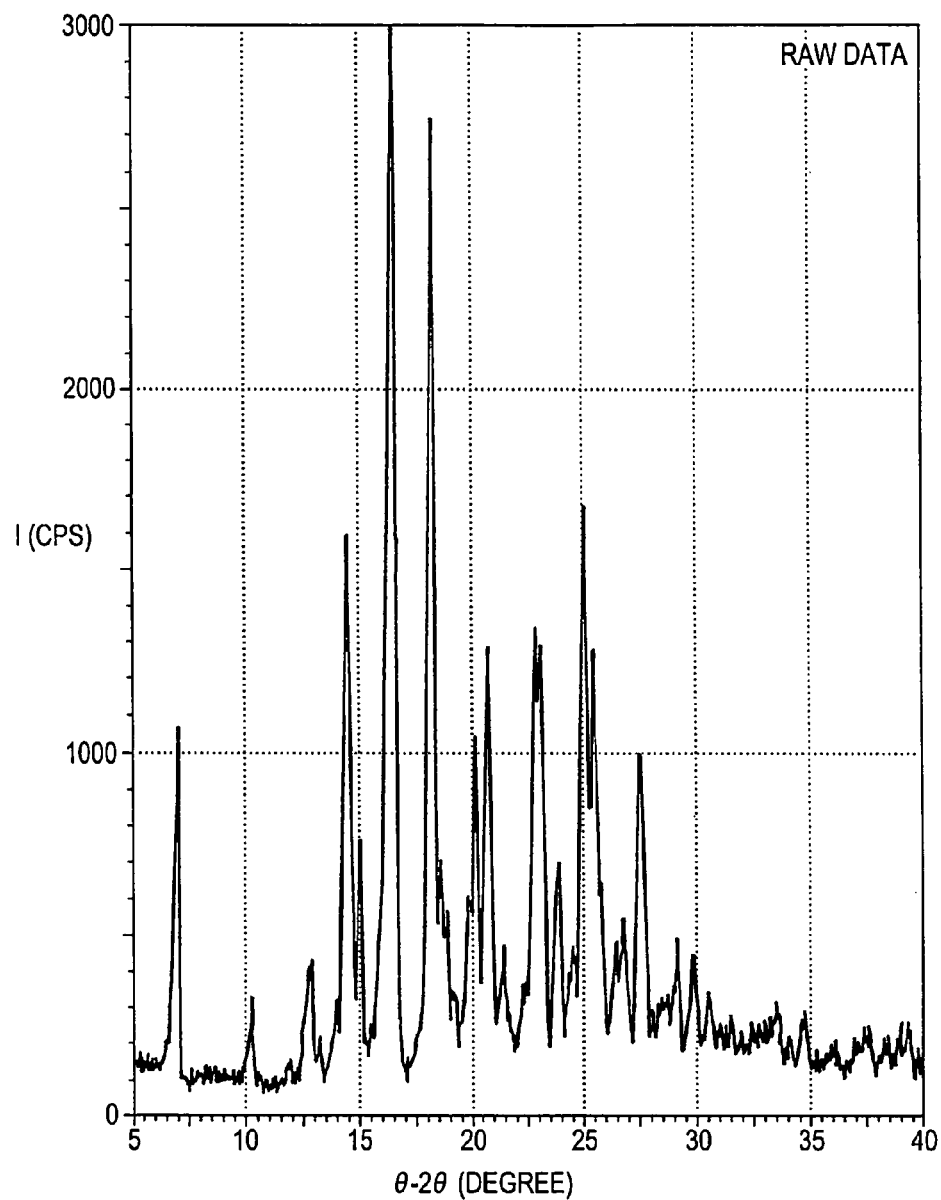
FIG. 1 A figure depicting powder X-ray diffraction spectrum of type A crystal of Compound 1 of the present invention. In the figure, the vertical axis indicates intensity (CPS), and the horizontal axis indicates 2θ (°).

This application was filed with claiming the conventional priority based on the provisional application 61/021,910 filed in the United States of America on Jan. 18, 2008, and the entire disclosure of the aforementioned provisional application is incorporated herein by reference.
Examples of the stable pharmaceutical composition provided by the present invention include the pharmaceutical composition in which decomposition of the compound or a salt thereof contained in the pharmaceutical composition as the active ingredient is reduced or eliminated in the pharmaceutical composition. Another embodiment of the stable pharmaceutical composition is the pharmaceutical composition of which coloring over period of time is reduced or eliminated. In the pharmaceutical composition of the present invention, decomposition and/or coloring of the compound represented by the general formula (I) or a salt thereof as the active ingredient is reduced or eliminated, and the composition has either one or both of the advantages. As the advantageous effect, the reduction or elimination of decomposition is more preferred. As the advantageous effect, the reduction or elimination of coloring may be sometimes more preferred. The composition preferably has both of the advantages, i.e., the reduction or elimination of the decomposition, and the reduction or elimination of the coloring. Examples of the pharmaceutical composition provided by the present invention include the pharmaceutical composition comprising a compound represented by the general formula (I) or a salt thereof as an active ingredient, and one or more kinds of pharmaceutically acceptable carriers having functions required for formulating pharmaceutical preparations. The pharmaceutical composition may also mean a pharmaceutical preparation to be distributed or clinically used.

The present invention provides a stable pharmaceutical composition comprising a compound represented by the general formula (I) or a salt thereof as an active ingredient, in which generation of decomposition products derived from the active ingredient, coloring of the active ingredient, and the like are reduced or eliminated, a method for preparing thereof, and a method for stabilizing a pharmaceutical composition comprising a compound represented by the general formula (I) or a salt thereof as an active ingredient. Examples of the method for stabilizing the pharmaceutical composition include a method of reducing or eliminating decomposition of a compound represented by the general formula (I) or a salt thereof in the pharmaceutical composition, and a method of reducing or eliminating coloring of a compound represented by the general formula (I) or a salt thereof over period of time in the pharmaceutical composition, resulting in reduction or elimination of coloring of the pharmaceutical composition over period of time. The present invention also provides a method for storing and/or distributing a pharmaceutical composition comprising a compound represented by the general formula (I) or a salt thereof as an active ingredient while quality of the composition is maintained.

The compound represented by the general formula (I) contained in the pharmaceutical composition of the present invention is defined as follows. Carbon atom may sometimes be represented simply by "C", hydrogen atom by "H", oxygen atom by "O", sulfur atom by "S", and nitrogen atom by "N".

Examples of Link in the aforementioned general formula (I) include a saturated straight hydrocarbon chain having 1 to 3 carbon atoms or an unsaturated straight hydrocarbon chain having 2 or 3 carbon atoms. In the compound represented by the general formula (I) contained in the pharmaceutical composition of the present invention, the straight chain of the saturated straight hydrocarbon chain is preferably unsubstituted. The straight chain of the unsaturated straight hydrocarbon chain is also preferably unsubstituted. As the saturated straight hydrocarbon chain, —$(CH_2)_n$— is preferred. Symbol n is an integer of 1 to 3. When n is 1, 2 or 3, the desired action is most characteristically exhibited. Methylene where n is 1, ethylene where n is 2 and trimethylene where n is 3 are preferred, and ethylene where n is 2 is particularly preferred.

The unsaturated hydrocarbon chain having 2 or 3 carbon atoms means a hydrocarbon chain which contains an unsaturated bond as a double bond or a triple bond among the carbon-carbon bonds. As the unsaturated hydrocarbon chain, an unsaturated hydrocarbon chain containing a double bond is preferred. When the chain contains one or more double bonds, the number of the double bond may preferably one. Specific examples include ethenylene which has two carbon atoms and contains one double bond, as well as ethynylene which has two carbon atoms and contains one triple bond, propen-3-yl which has three carbon atoms and contains one double bond, and propyn-3-yl which has three carbon atoms and contains one triple bond.

$C^2$, $C^3$, $C^4$, $C^5$ and $C^6$ in the aromatic ring (E) in the formula (I) each represent a ring-constituting carbon atom. The ring-constituting carbon atoms form the aromatic ring (E), and accordingly, they are represented as C or CH. Among them, any one of ring-constituting carbon atoms to which Rs or Ar does not bind is a carbon atom substituted with amino group.

Rs and AR each bind to any of the ring-constituting carbon atoms $C^2$, $C^3$, $C^4$, $C^5$ or $C^6$ in the aromatic ring (E), and this means that, for example, when AR binds to $C^2$, Rs binds to any of the ring-constituting carbon atoms $C^3$, $C^4$, $C^5$ and $C^6$, when AR binds to $C^3$, Rs binds to any of the ring-constituting carbon atoms $C^2$, $C^4$, $C^5$ and $C^6$, and when AR bind to $C^4$, Rs binds to the ring-constituting carbon atom $C^2$ or $C^3$. Preferred examples of these combinations of substitution positions include a compound wherein AR binds to $C^2$, and Rs binds to any of the atoms $C^3$, $C^4$, and $C^5$, and particularly preferred examples include a compound wherein AR binds to $C^2$, and Rs binds to $C^3$ or $C^4$. Preferred examples also include a compound wherein AR binds to $C^3$, and Rs binds to any of the atoms $C^4$, $C^5$, and $C^6$, and particularly preferred examples also include a compound wherein AR binds to $C^3$, and Rs binds to the atom $C^4$ or $C^5$. A still more preferred example is a compound wherein AR binds to $C^3$, and Rs binds to $C^4$.

One of the atoms $C^2$, $C^3$, $C^4$, $C^5$ and $C^6$ to which Rs and AR do not bind is a carbon atom substituted with amino group. For example, when AR binds to $C^2$, and Rs binds to $C^3$, one of the ring-constituting carbon atoms $C^4$, $C^5$, and $C^6$ is a carbon atom substituted with amino group. As another example, it is meant that when AR binds to $C^3$, and Rs binds to $C^4$, one of the atoms $C^2$, $C^5$, and $C^6$ is a carbon atom substituted with amino group. Among these combinations and other combinations, preferred examples are a compound wherein AR binds to $C^2$, Rs binds to $C^3$, and $C^4$ is a carbon atom substituted with amino group; a compound wherein AR binds to $C^2$, Rs binds to $C^4$, and $C^5$ is a carbon atom substituted with amino group; a compound wherein AR binds to $C^2$, Rs binds to $C^5$, and $C^4$ is a carbon atom substituted with amino group; a compound wherein AR binds to $C^3$, Rs binds to $C^4$, and $C^5$ is a carbon atom substituted with amino group; a compound wherein AR binds to $C^3$, Rs binds to $C^4$, and $C^6$ is a carbon atom substituted with amino group; a compound wherein AR binds to $C^3$, Rs binds to $C^5$, and $C^4$ is a carbon atom substituted with amino group; a compound wherein AR binds to $C^3$, Rs binds to $C^6$, and $C^5$ is a carbon atom substituted with amino group, and the like. Furthermore, particularly preferred examples include a compound wherein AR binds to $C^3$, Rs binds to $C^4$, and $C^5$ is a carbon atom substituted with amino group; and a compound wherein AR binds to $C^3$, Rs binds to $C^4$, and $C^6$ is a carbon atom substituted with amino group, and a particularly preferred example is a compound wherein AR binds to $C^3$, Rs binds to $C^4$, and $C^5$ is a carbon atom substituted with amino group.

Further, a particularly preferred example is a compound wherein AR binds to $C^3$, Rs binds to $C^4$, and $C^5$ is a carbon atom substituted with amino group.

$A^6$ in -$A^6$-Qp represents a single bond or methylene, and Qp represents a phenyl group which may be substituted with one of $T^1$ or two or more of the same or different $T^1$. The substituent $T^1$ is a linear or branched saturated alkyl group having 1 to 4 carbon atoms, hydroxyl group, fluorine atom, chlorine atom, bromine atom, trifluoromethyl group, nitro group, an alkoxy group having 1 to 4 carbon atoms, or a mono- or dialkylamino group having 1 to 4 carbon atoms. Specific examples of -$A^6$-Qp include phenyl group, methylphenyl group, chlorophenyl group, benzyl group, methylbenzyl group, chlorobenzyl group, dichlorobenzyl group, fluorobenzyl group, trifluoromethylbenzyl group, nitrobenzyl group, methoxyphenyl group, N-methylaminobenzyl group, N,N-dimethylaminobenzyl group, and the like.

Rs in the general formula (I) is defined to represent -D-Rx or —N(Ry)(Rz).

D is defined to represent a single bond, oxygen atom, sulfur atom, —S(O)—, —$S(O)_2$—, or —C(O)—. Among them, oxygen atom and sulfur atom are preferred, and oxygen atom is particularly preferred. Another preferred examples include the compounds wherein D represent a single bond.

Rx represents a linear or branched saturated alkyl group having 3 to 8 carbon atoms, or represents Ra, Rb, or Rc mentioned above.

As for Rx, examples of the linear or branched saturated alkyl group having 3 to 8 carbon atoms include, for example, propyl group, isopropyl group, butyl group, isobutyl group, 1-methylpropyl group, t-butyl group, pentyl group, isopentyl group, 2-methylbutyl group, 2,2-dimethylpropyl group, hexyl group, 4-methylpentyl group, 2,3-dimethylbutyl group, 2-ethylbutyl group, heptyl group, octyl group, and the like, butyl group, isobutyl group, 2-ethylbutyl group, cyclopentyl group, cyclohexyl group, cyclopentylmethyl group, and cyclohexylmethyl group are preferred, and butyl group, isobutyl group, and 2-ethylbutyl group are particularly preferred. There is another embodiment where cyclopentyl group, cyclohexyl group, cyclopentylmethyl group, and cyclohexylmethyl group are particularly preferred As for Rx, $R^1$ of Ra is defined to be a saturated cyclic alkyl group having 3 to 7 carbon atoms substituted with a lower alkyl group having 1 to 4 carbon atoms or an unsubstituted saturated cyclic alkyl group having 3 to 7 carbon atoms, or a condensed saturated cyclic alkyl group having 6 to 8 carbon atoms substituted with a lower alkyl group having 1 to 4 carbon atoms or an unsubstituted condensed saturated cyclic alkyl group having 6 to 8 carbon atoms. As for $R^1$, examples of the saturated cyclic alkyl group having 3 to 7 carbon atoms include cyclopropyl group, cyclobutyl group, cyclopentyl group, cyclohexyl group, cycloheptyl group, and the like, and cyclopentyl group, cyclohexyl group, and cycloheptyl group are particularly preferred. As for $R^1$, examples of the condensed saturated cyclic alkyl group having 6 to 8 carbon atoms group include bicyclo[2,2,1]heptyl group, bicyclo[2,2,2]octyl group, and the like.

Examples of the lower alkyl group having 1 to 4 carbon atoms substituting on $R^1$ include methyl group, ethyl group, propyl group, isopropyl group, butyl group, isobutyl group, t-butyl group, and the like. Examples of $R^1$ substituted with a lower alkyl group having 1 to 4 carbon atoms include methylcyclopentyl group, methylcyclohexyl group, methylbicyclo[2,2,1]heptyl group, and the like.

Symbol k is defined to be 0 or an integer of 1 to 3. A bond where k is 0, methylene where k is 1, and ethylene where k is 2 are preferred, and a bond where k is 0, and methylene where k is 1 are particularly preferred.

Examples of Ra include cyclopropyl group, cyclobutyl group, cyclopentyl group, cyclohexyl group, cycloheptyl group, cyclopropylmethyl group, cyclobutylmethyl group, cyclopentylmethyl group, cyclohexylmethyl group, cycloheptylmethyl group, 2-cyclopentylethyl group, 2-cyclohexylethyl group, 3-cyclohexylpropyl group, 2-methylcyclopentyl group, 3-methylcyclopentyl group, 3,4-dimethylcyclopentyl group, 4-methylcyclohexyl group, 4,4-dimethylcyclohexyl group, 4-ethylcyclohexyl group, 4-methylcyclohexylmethyl group, bicyclo[2,2,1]heptane-2-methyl group, bicyclo[2,2,2]octane-2-methyl group, 3-methylbicyclo[2,2,1]heptane-2-methyl group, bicyclo[2,2,1]hept-1-ylmethyl group, bicyclo[2,2,2]oct-1-methyl group, and the like. Cyclopentyl group, cyclohexyl group, cycloheptyl group, cyclopentylmethyl group, cyclohexylmethyl group, 2-cyclopentylethyl group, and 2-cyclohexylethyl group are preferred, and cyclopentyl group, cyclohexyl group, cycloheptyl group, cyclopentylmethyl group, and cyclohexylmethyl group are particularly preferred.

As for Rx, A2 in Rb is defined to be a single bond, oxygen atom, sulfur atom, —S(O)—, —S(O)$_2$—, or —N($R^4$)—. $R^4$ is defined to be a lower alkyl group having 1 to 4 carbon atoms. Preferred examples are methyl group, ethyl group, propyl group, isopropyl group, butyl group, isobutyl group, t-butyl group, and the like, and methyl group and ethyl group are particularly preferred examples. Therefore, particularly preferred examples of $A^2$ include a single bond, oxygen atom, sulfur atom, —N(methyl)-, and —N(ethyl)-. $A^2$ is particularly preferably a single bond.

$A^1$ is defined to be a single bond or an alkylene (a) having 1 to 3 carbon atoms, i.e., methylene, ethylene or trimethylene, and examples include a single bond, a methylene group substituted with 1 to 3 methyl groups or ethyl groups, unsubstituted methylene group, and an ethylene group substituted with 1 to 3 methyl groups or ethyl groups and unsubstituted ethylene group. However, when $A^2$ represents oxygen atom, sulfur atom, —S(O)—, —S(O)$_2$— or —N($R^4$)—, $A^1$ is ethylene or trimethylene. Further, the alkylene (a) may be substituted with a lower alkyl group having 1 to 4 carbon atoms or phenyl group. Examples of the lower alkyl group having 1 to 4 carbon atoms for the above compound include methyl group, ethyl group, propyl group, isopropyl group, butyl group, isobutyl group, t-butyl group, and the like, and methyl group, and ethyl group are preferred examples. Specific examples of $A^1$ include methylene, methylmethylene, ethylmethylene, phenylmethylene, ethylene, methylethylene, dimethylethylene, ethylethylene, phenylethylene, trimethylene, methyltrimethylene, and the like. Among them, when $A^2$ represents a single bond, $A^1$ is most preferably a single bond, or methylene, methylmethylene, or ethylene, or a single bond may be particularly preferred as the case may be. Further, when $A^2$ represents oxygen atom, sulfur atom, —S(O)—, —S(O)$_2$— or —N($R^4$)—, $A^1$ is most preferably ethylene.

Q in Rb is defined to be a residue of a partially unsaturated or completely unsaturated monocyclic or condensed bicyclic carbon ring or heterocyclic ring (q), and the heterocyclic ring (q) means a ring containing 1 to 4 the same or different ring-constituting heteroatoms selected from the group consisting of nitrogen atom, oxygen atom, and sulfur atom. The term "residue" means a monovalent group formed by eliminating hydrogen atom bonding to a ring-constituting atom. The residue of monocyclic carbon ring or heterocyclic ring is a partially unsaturated or completely unsaturated substituent having 5 to 7 atoms, and examples include, for example, phenyl group, thienyl group, furyl group, pyrrolyl group, pyridyl group, oxazolyl group, isoxazolyl group, thiazolyl group, isothiazolyl group, imidazolyl group, pyrazolyl group, oxadiazolyl group, thiadiazolyl group, triazolyl group, tetrazolyl group, and the like. Among them, phenyl group, thienyl group, furyl group, pyridyl group, and oxazolyl group are preferred examples, and phenyl group is particularly preferred.

The condensed bicyclic carbon ring or heterocyclic ring is a partially unsaturated or completely unsaturated ring having 8 to 11 atoms, and examples of residue thereof include, for example, naphthyl group, tetrahydronaphthyl group, indanyl group, indenyl group, quinolyl group, isoquinolyl group, indolyl group, benzofuryl group, benzothienyl group, benzimidazolyl group, benzoxazolyl group, benzothiazolyl group, indazolyl group, 4H-chromenyl group, dihydrobenzodioxyl group, benzisoxazolyl group, pyrrolopyridinyl group, pyrazolopyridinyl group, triazolopyridinyl group, thienopyridinyl group, thienopyrazolyl group, 1,3-dihydrobenzimidazole group, dihydro-3H-benzoxazole group, dihydro-3H-benzothiazole group, and the like. Among them, naphthyl group, tetrahydronaphthyl group, indanyl group, indolyl group, and dihydrobenzodioxyl group are preferred examples, and indanyl group is one of particularly preferred examples.

Q binds to $A^2$ at an arbitrary position on the ring. Preferred examples of Q with indication of bonding position include phenyl group, 2- or 3-thienyl group, 2- or 3-furyl group, 2-, 3- or 4-pyridyl group, 2-, 4- or 5-oxazolyl group, 1- or 2-naphthyl group, 1-, 2-, 5- or 6-tetrahydronaphthyl group, indan-1-yl group, indan-2-yl group, indan-4-yl group, indan-5-yl group, 1-, 2-, 3-, 4-, 5-, 6-, or 7-indolyl group, 2-, 5- or 6-dihydrobenzodioxyl group, and the like. Among them, phenyl group, and indan-2-yl group are particularly preferred.

In Rb, $R^2$ and $R^3$ are defined to be substituents of Q, and independently represent hydrogen atom, a linear or branched saturated alkyl group having 1 to 4 carbon atoms, oxo group, thioxo group, fluorine atom, chlorine atom, bromine atom, trifluoromethyl group, —$OR^5$, —$N(R^6)(R^{6'})$, —$NHCOR^7$, —$NHSO_2R^3$, or -$A^6$-Qa, or bind to each other to represent methylenedioxy group.

Examples of the linear or branched saturated alkyl group having 1 to 4 carbon atoms include methyl group, ethyl group, propyl group, isopropyl group, butyl group, isobutyl group, t-butyl group, and the like, and methyl group is particularly preferred.

$R^6$ in —$N(R^6)(R^{6'})$ represents hydrogen atom or a lower alkyl group having 1 to 4 carbon atoms. $R^{6'}$ has the same meaning as $R^6$, or binds to $R^6$ to form a 3- to 6-membered ring together with the nitrogen atom to which they bind to form a saturated nitrogen-containing cycloalkyl group or morpholino group. Therefore, specific examples of —$N(R^6)(R^{6'})$ include amino group, N-methylamino group, N-ethylamino group, N-propylamino group, N-isopropylamino group, N,N-dimethylamino group, N,N-diethylamino group, piperidino group, pyrrolidino group, morpholino group, and the like. N,N-Dimethylamino group, piperidino group, morpholino group, and the like are preferred examples, and N,N-dimethylamino group is a particularly preferred example.

Preferred example of $R^2$ and $R^5$ include hydrogen atom, methyl group, fluorine atom, chlorine atom, trifluoromethyl group, methoxy group, and dimethylamino group. In another preferred embodiment, $R^2$ and $R^3$ both are hydrogen atoms, or independently represent methyl group, fluorine atom, chlorine atom, trifluoromethyl group, methoxy group, or dimethylamino group.

$R^5$ and $R^7$ are defined to independently represent hydrogen atom, a lower alkyl group having 1 to 4 carbon atoms, or a -$A^6$-Qa group. Examples of the lower alkyl group having 1 to 4 carbon atoms include methyl group, ethyl group, propyl group, isopropyl group, butyl group, isobutyl group, t-butyl group, and the like, and among them, methyl group is a preferred example.

$A^6$ in -$A^6$-Qa has the same meaning as that defined above. Qa is defined to be a partially unsaturated or completely unsaturated monocyclic or condensed bicyclic carbon ring or a heterocyclic ring (qa), and the heterocyclic ring (qa) means a substituent containing 1 to 4 the same or different ring-constituting heteroatoms selected from the group consisting of nitrogen atom, oxygen atom, and sulfur atom. The monocyclic carbon ring or heterocyclic ring is a partially unsaturated or completely unsaturated ring having 5 to 7 atoms, and examples of residue thereof include, for example, phenyl group, thienyl group, furyl group, pyrrolyl group, pyridyl group, oxazolyl group, isoxazolyl group, thiazolyl group, isothiazolyl group, imidazolyl group, pyrazolyl group, oxadiazolyl group, thiadiazolyl group, triazolyl group, tetrazolyl group, and the like. The condensed bicyclic carbon ring or heterocyclic ring is a partially unsaturated or completely unsaturated ring having 8 to 11 atoms, and examples of residue thereof include, for example, naphthyl group, indanyl group, indenyl group, quinolyl group, isoquinolyl group, indolyl group, benzofuryl group, benzothienyl group, benzimidazolyl group, benzoxazolyl group, benzothiazolyl group, indazolyl group, and the like.

Qa binds to $A^6$ at an arbitrary position on the ring. Further, Qa may be substituted with two or more of the same or different $T^1$. $T^1$ has the same meaning as defined above.

Specific examples of -$A^6$-Qa include phenyl group, methylphenyl group, chlorophenyl group, benzyl group, methylbenzyl group, chlorobenzyl group, dichlorobenzyl group, fluorobenzyl group, trifluoromethylbenzyl group, nitrobenzyl group, methoxyphenyl group, N-methylaminobenzyl group, N,N-dimethylaminobenzyl group, furyl group, thienyl group, pyrrolyl group, pyridyl group, oxazolyl group, isoxazolyl group, thiazolyl group, isothiazolyl group, imidazolyl group, pyrazolyl group, oxadiazolyl group, thiadiazolyl group, triazolyl group, tetrazolyl group, naphthyl group, indanyl group, indenyl group, quinolyl group, isoquinolyl group, indolyl group, benzofuryl group, benzothienyl group, benzimidazolyl group, benzoxazolyl group, benzothiazolyl group, indazolyl group, and the like.

$R^8$ is defined to be a lower alkyl group having 1 to 4 carbon atoms, and examples of the lower alkyl group having 1 to 4 carbon atoms include methyl group, ethyl group, propyl group, isopropyl group, butyl group, isobutyl group, t-butyl group, and the like.

Therefore, preferred examples of $R^2$ and $R^3$ include hydrogen atom, methyl group, fluorine atom, chlorine atom, trifluoromethyl group, methoxy group, dimethylamino group, acetylamino group, and methylsulfonylamino group, and hydrogen atom, methyl group, fluorine atom, chlorine atom, trifluoromethyl group, methoxy group, and dimethylamino group are particularly preferred. When Q represents phenyl group, $A^1$ represents a single bond, or unsubstituted methylene, and $A^2$ represents a single bond, at least one of $R^2$ and $R^3$ preferably represents a substituent other than hydrogen atom.

Particularly preferred examples of Rb include 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,5-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, or 2-(N-ethyl-N-phenylamino)ethyl group, and the like. Indan-2-yl group can also be mentioned as one of particularly preferred examples.

Symbol p in Rc is defined to be an integer of 2 to 4. Ethylene where p is 2, and trimethylene where p is 3 are preferred, and ethylene where p is 2 is particularly preferred. $A^4$ represents a single bond, or represents methylene or ethylene, and a single bond and methylene are particularly preferred. $A^5$ represents —C(O)—, —C(S)—, or —S(O)$_2$—, and all of them are preferred. Rd represents hydrogen atom, an alkyl group having 1 to 8 carbon atoms, or a group Qa. Re represents an alkyl group having 1 to 8 carbon atoms, a -$A^6$-Qa group, a —(CH$_2$)$_i$R$^{14}$ group, a —OR$^{28}$ group, a —SR$^{28}$ group, or a —N(R$^{29}$)(R$^{30}$) group. The group Qa and -$A^6$-Qa have the same meanings as defined above.

The alkyl group having 1 to 8 carbon atoms is a linear or branched saturated alkyl group or a linear or branched partially unsaturated alkyl group, or an alkyl group which may contain a cycloalkyl group having 3 to 7 carbon atoms, and examples include, for example, methyl group, ethyl group, propyl group, isopropyl group, butyl group, isobutyl group, t-butyl group, pentyl group, isopentyl group, 2-methylbutyl group, 2,2-dimethylpropyl group, hexyl group, 4-methylpentyl group, 2,3-dimethylbutyl group, 2-ethylbutyl group, heptyl group, octyl group, cyclopropyl group, cyclobutyl group, cyclopentyl group, cyclohexyl group, cycloheptyl group, cyclopropylmethyl group, cyclobutylmethyl group, cyclopentylmethyl group, cyclohexylmethyl group, cycloheptylmethyl group, 2-cyclopentylethyl group, 2-cyclohexylethyl group, 2-methylcyclopentyl group, 3-methylcyclopentyl group, 3,4-dimethylcyclopentyl group, 4-methylcyclohexyl group, 4,4-dimethylcyclohexyl group, 4-ethylcyclohexyl group, 4-methylcyclohexylmethyl group, and the like.

Symbol i in —(CH$_2$)$_i$R$^{14}$ represents an integer of 1 to 3, and R$^{14}$ represents hydroxyl group, an alkoxy group having 1 to 4 carbon atoms, carboxyl group, or an N,N-dialkylcarbamoyl group having 1 to 4 carbon atoms. Examples of the alkoxy group having 1 to 4 carbon atoms include methoxy group, ethoxy group, propyloxy group, isopropyloxy group, butoxy group, isobutyloxy group, t-butyloxy group, and the like. Examples of the N,N-dialkylcarbamoyl group having 1 to 4 carbon atoms include N,N-dimethylcarbamoyl group, N,N-diethylcarbamoyl group, and the like.

R$^{28}$ in —OR$^{28}$ or —SR$^{28}$ represents an alkyl group having 1 to 8 carbon atoms, or -$A^6$-Qa, and these have the same meanings as defined above.

R$^{29}$ in —N(R$^{29}$)(R$^{30}$) represents an alkyl group having 1 to 8 carbon atoms, an alkoxycarbonyl group having 1 to 4 carbon atoms, or -$A^6$-Qa. Among them, the alkyl group having 1 to 8 carbon atoms and -$A^6$-Qa have the same meanings as those defined above. Examples of the alkoxycarbonyl group having 1 to 4 carbon atoms include methyloxycarbonyl group, ethyloxycarbonyl group, propyloxycarbonyl group, isopropyloxycarbonyl group, butyloxycarbonyl group, isobutyloxycarbonyl group, t-butyloxycarbonyl group, and the like. R$^{30}$ represents hydrogen atom or a lower alkyl group having 1 to 4 carbon atoms, or binds to R$^{29}$ to form a 3- to 6-membered ring together with the nitrogen atom to which they bind to form a saturated nitrogen-containing cycloalkyl group or morpholino group. The lower alkyl group having 1 to 4 carbon atoms has the same meaning as defined above. Examples of the compound where "R$^{30}$ binds to R$^{29}$ to form a 3- to 6-membered ring together with the nitrogen atom to which they bind to form a saturated nitrogen-containing cycloalkyl group or morpholino group" include, for example, a compound wherein a cyclic aminoalkyl group containing nitrogen atom such as pyrrolidino group, piperazino group, and morpholino group is formed.

Preferred examples of Rd include hydrogen atom as well as methyl group, ethyl group, propyl group, isopropyl group, butyl group, isobutyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorobenzyl group, 4-fluorobenzyl group, pyridin-2-yl group, pyridin-3-yl group, pyridin-4-yl group, and the like.

Particularly preferred examples of Rd include methyl group, ethyl group, propyl group, isopropyl group, butyl group, isobutyl group, cyclopropyl group, cyclopentyl group, cyclohexyl group, phenyl group, 4-methylphenyl group, 4-chlorophenyl group, 4-fluorophenyl group, benzyl group, 4-chlorophenylmethyl group, 4-fluorophenylmethyl group, and the like.

Preferred examples of substituted -$A^4$-Rd include methyl group, ethyl group, propyl group, isopropyl group, butyl group, isobutyl group, pentyl group, isoamyl group, cyclopropyl group, cyclopropylmethyl group, 2-(cyclopropyl)ethyl group, cyclopentyl group, cyclopentylmethyl group, 2-(cyclopentyl)ethyl group, cyclohexyl group, cyclohexylmethyl group, 2-(cyclohexyl)ethyl group, phenyl group, 4-methylphenyl group, 4-chlorophenyl group, 4-fluorophenyl group, benzyl group, 4-chlorophenylmethyl group, 4-fluorophenylmethyl group, 2-(4-chlorophenyl)ethyl group, 2-(4-fluorophenyl)ethyl group, pyridin-2-yl group, pyridin-3-yl group, pyridin-4-yl group, (pyridin-2-yl)methyl group, (pyridin-3-yl)methyl group, (pyridin-4-yl)methyl group, and the like.

Particularly preferred examples of substituted -$A^4$-Rd include methyl group, ethyl group, propyl group, isopropyl group, butyl group, isobutyl group, pentyl group, isoamyl group, cyclopropyl group, cyclopropylmethyl group, cyclopentyl group, cyclopentylmethyl group, cyclohexyl group, cyclohexylmethyl group, phenyl group, 4-methylphenyl group, 4-chlorophenyl group, 4-fluorophenyl group, benzyl group, 4-chlorophenylmethyl group, 4 fluorophenylmethyl group, 2-(4-chlorophenyl)ethyl group, 2-(4-fluorophenyl)ethyl group, and the like.

Preferred examples of Re include methyl group, ethyl group, propyl group, isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, phenylmethyl group, 4-chlorophenylmethyl group, 4-fluorophenylmethyl group, pyridin-2-yl group, pyridin-3-yl group, pyridin-4-yl group, furan-2-yl group, furan-3-yl group, thiophen-2-yl group, thiophen-3-yl group, methoxy group, ethoxy group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, methylthioxo group, amino group, N-methylamino group, N,N-dimethylamino group, N-ethylamino group, N,N-diethylamino group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, N-(pyridin-2-yl)amino group, N-(pyridin-3-yl)amino group, N-(pyridin-4-yl)amino group, N-(furan-2-yl)amino group, N-(furan-3-yl)amino group, N-(thiophen-2-yl)amino group, N-(thiophen-3-yl)amino group, pyrrolidino group, piperidino group, morpholino group, methyloxycarbonylamino group, ethyloxycarbonylamino group, and the like.

Particularly preferred examples of Re include isopropyl group, butyl group, isobutyl group, t-butyl group, cyclopropyl group, cyclopentyl group, cyclohexyl group, cyclopentylmethyl group, cyclohexylmethyl group, phenyl group, 4-methylphenyl group, 4-chlorophenyl group, 4-fluorophenyl group, propyloxy group, isopropyloxy group, butyloxy group, isobutyloxy group, t-butyloxy group, cyclopropyloxy group, cyclopentyloxy group, cyclohexyloxy group, cyclopentylmethyloxy group, cyclohexylmethyloxy group, phenyloxy group, 4-methylphenyloxy group, 4-chlorophenyloxy group, 4-fluorophenyloxy group, N-propylamino group, N-isopropylamino group, N-butylamino group, N-isobutylamino group, N-t-butylamino group, N-cyclopropylamino group, N-cyclopentylamino group, N-cyclohexylamino group, N-phenylamino group, N-(4-methylphenyl)amino group, N-(4-chlorophenyl)amino group, N-(4-fluorophenyl)amino group, pyrrolidino group, piperidino group, morpholino group, and the like.

Preferred examples of -$A^5$-Re include acetyl group, thioacetyl group, methanesulfonyl group, propionyl group, ethylthiocarbonyl group, butyryl group, propylthiocarbonyl group, isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, phenylmethylcarbonyl group, 4-methylphenylmethylcarbonyl group, 4-chlorophenylmethylcarbonyl group, 4-fluorophenylmethylcarbonyl group, (pyridin-2-yl)carbonyl group, (pyridin-2-yl)thiocarbonyl group, (pyridin-3-yl)carbonyl group, (pyridin-4-yl)carbonyl group, (furan-2-yl)carbonyl group, (thiophen-2-yl)carbonyl group, methyloxycarbonyl group, methylsulfanylcarbonyl group, methyloxythiocarbonyl group, methyloxycarbonylaminocarbonyl group, carbamoyl group, N-methylcarbamoyl group, N-methylthiocarbamoyl group, N,N-dimethylcarbamoyl group, N,N-dimethylthiocarbamoyl group, N,N-dimethylsulfamoyl group, ethyloxycarbonyl group, ethyloxycarbonylaminocarbonyl group, N-ethylcarbamoyl group, N-ethylthiocarbamoyl group, N,N-diethylcarbamoyl group, N,N-diethylthiocarbamoyl group, N,N-diethylsulfamoyl group, propyloxycarbonyl group, N-propylcarbamoyl group, N-propylthiocarbamoyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl) carbamoyl group, N-(4-fluorophenyl)thiocarbamoyl group, phenylmethyloxycarbonyl group, 4-methylphenylmethyloxycarbonyl group, 4-chlorophenylmethyloxycarbonyl group, 4-fluorophenylmethyloxycarbonyl group, N-(pyridin-2-yl)carbamoyl group, N-(pyridin-2-yl)thiocarbamoyl group, N-(pyridin-3-yl)carbamoyl group, N-(pyridin-3-yl)thiocarbamoyl group, N-(pyridin-4-yl)carbamoyl group, N-(pyridin-4-yl)thiocarbamoyl group, N-(furan-2-yl)carbamoyl group, N-(thiophen-2-yl)carbamoyl group, (pyrrolidino-1-yl)carbonyl group, (piperidino-1-yl)carbonyl group, (morpholino-4-yl)carbonyl group, and the like.

Particularly preferred examples of -$A^5$-Re include isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cyclopropylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, (pyrrolidino-1-yl)carbonyl group, (piperidino-1-yl)carbonyl group, (morpholino-4-yl)carbonyl group, and the like.

Specific examples of Rc include 2-(N-isobutyryl-N-methylamino)ethyl group, 2-(N-ethyl-N-isobutyrylamino)ethyl group, 2-(N-isobutyryl-N-propylamino)ethyl group, 2-(N-isobutyryl-N-isopropylamino)ethyl group, 2-(N-butyl-N-isobutyrylamino)ethyl group, 2 (N-isobutyl-N-isobutyrylamino)ethyl group, 2-(N-cyclopropyl-N-isobutyrylamino)ethyl group, 2-(N-cyclopentyl-N-isobutyrylamino)ethyl group, 2-(N-cyclopentylmethyl-N-isobutyrylamino)ethyl group, 2-(N-cyclohexyl-N-isobutyrylamino)ethyl group, 2-(N-cyclohexylmethyl-N-isobutyrylamino)ethyl group, 2-(N-isobutyryl-N-phenylamino)ethyl group, 2-[N-isobutyryl-N-(4-methylphenyl)amino]ethyl group, 2-[N-(4-chlorophenyl)-N-isobutyrylamino]ethyl group, 2-[N-(4-fluorophenyl)-N-isobutyrylamino]ethyl group, 2-(N-benzyl-N-isobutyrylamino)ethyl group, 2-[N-(4-chlorophenylmethyl)-N-isobutyrylamino]ethyl group, 2-[N-(4-fluorophenylmethyl)-N-isobutyrylamino]ethyl group, 2-[N-[2-(4-chlorophenyl)ethyl]-N-isobutyrylamino]ethyl group, 2-[N-[2-(4-fluorophenyl)ethyl]-N-isobutyrylamino]ethyl group, 2-(N-isobutylthiocarbonyl-N-methylamino)ethyl group, 2-(N-isobutylthiocarbonyl-N-isopropylamino)ethyl group, 2-(N-butyl-N-isobutylthiocarbonylamino)ethyl group, 2-(N-isobutyl-N-isobutylthiocarbonylamino)ethyl group, 2-(N-cyclopentyl-N-isobutylthiocarbonylamino)ethyl group, 2-(N-cyclopentylmethyl-N-isobutylthiocarbonylamino)ethyl group, 2-(N-isobutylthiocarbonyl-N-phenylamino)ethyl group, 2-(N-benzyl-N-isobutylthiocarbonylamino)ethyl group, 2-[N-(4-fluorophenylmethyl)-N-isobutylthiocarbonylamino]ethyl group, 2-(N-methyl-N-pivaloylamino)ethyl group, 2-(N-isopropyl-N-pivaloylamino)ethyl group, 2-(N-butyl-N-pivaloylamino)ethyl group, 2-(N-isobutyl-N-pivaloylamino)ethyl group, 2-(N-cyclohexyl-N-pivaloylamino)ethyl group, 2-(N-cyclohexylmethyl-N-pivaloylamino)ethyl group, 2-(N-phenyl-N-pivaloylamino)ethyl group, 2-(N-benzyl-N-pivaloylamino)ethyl group, 2-(N-cyclopentylcarbonyl-N-methylamino)ethyl group, 2-(N-butyl-N-cyclopentylcarbonylamino)ethyl group, 2-(N-cyclopentylcarbonyl-N-isobutylamino)ethyl group, 2-(N-cyclopentylcarbonyl-N-cyclopentylmethylamino)ethyl group, 2-(N-cyclopentylcarbonyl-N-phenylamino)ethyl group, 2-[N-cyclopentylcarbonyl-N-(4-fluorophenyl)amino]ethyl group, 2-[N-benzyl-N-cyclopentylcarbonylamino)ethyl group, 2-[N-cyclopentylcarbonyl-N-(4-fluorophenylmethyl)amino]ethyl group, 2-(N-methyl-N-phenylsulfonylamino)ethyl group, 2-(N-ethyl-N-phenylsulfonylamino)ethyl group, 2-(N-phenylsulfonyl-N-propylamino)ethyl group, 2-(N-isopropyl-N-phenylsulfonylamino)ethyl group, 2-(N-butyl-N-phenylsulfonylamino)ethyl group, 2-(N-isobutyl-N-phenylsulfonylamino)ethyl group, 2-(N-cyclopropyl-N-phenylsulfonylamino)ethyl group, 2-(N-cyclopentyl-N-phenylsulfonylamino)ethyl group, 2-(N-cyclopentylmethyl-N-phenylsulfonylamino)ethyl group, 2-(N-cyclohexyl-N-phenylsulfonylamino)ethyl group, 2-(N-cyclohexylmethyl-N-phenylsulfonylamino)ethyl group, 2-(N-phenyl-N-phenylsulfonylamino)ethyl group, 2-[N-(4-fluorophenyl)-N-phenylsulfonylamino]ethyl group, 2-(N-benzyl-N-phenylsulfonylamino)ethyl group, 2-[N—(N-butylcarbamoyl)-N-methylamino]ethyl group, 2-[N-butyl-N—(N-butylcarbamoyl)amino]ethyl group, 2-[N—(N-butylcarbamoyl)-N-isobutylamino]ethyl group, 2-[N—(N-butylcarbamoyl)-N-cyclopentylamino]ethyl group, 2-[N—(N-butylcarbamoyl)-N-cyclohexylmethylamino]ethyl group, 2-[N—(N-butylcarbamoyl)-N-phenylamino]ethyl group, 2-{N—(N-butylcarbamoyl)-N-(4-fluorophenyl)amino}ethyl group, 2-[N-benzyl-N—(N-butylcarbamoyl)amino]ethyl group, 2-{N—(N-butylcarbamoyl)-N-(4-fluorophenylmethyl)aminoethyl group, 2-(N—(N-butylcarbamoyl)-N-[2-(4-fluorophenyl)ethyl]amino}ethyl group, 2-[N—(N-isopropylthiocarbamoyl)-N-methylamino]ethyl group, 2-[N-butyl-N—(N-isopropylthiocarbamoyl)amino]ethyl group, 2-[N-isobutyl-N—(N-isopropylthiocarbamoyl)amino]ethyl group, 2-[N-cyclopentyl-N—(N-isopropylthiocarbamoyl)amino]ethyl group, 2-[N-cyclohexylmethyl-N—(N-isopropylthiocarbamoyl)amino]ethyl group, 2-[N—(N-isopropylthiocarbamoyl)-N-phenylamino]ethyl group, 2-2 N-{4-fluorophenyl)-N—(N-isopropylthiocarbamoyl)amino}ethyl group, 2-[N-benzyl-N—(N-isopropylthiocarbamoyl)amino]ethyl group, 2-(N-isobutyloxycarbonyl-N-methylamino)ethyl group, 2-(N-butyl-N-isobutyloxycarbonylamino)ethyl group, 2-(N-isobutyl-N-isobutyloxycarbonylamino)ethyl group, 2-(N-cyclopentyl-N-isobutyloxycarbonylamino)ethyl group, 2-(N-cyclohexylmethyl-N-isobutyloxycarbonylamino)ethyl group, 2-(N-isobutyloxycarbonyl-N-phenylamino)ethyl group, 2-[N-(4-fluorophenyl)-N-isobutyloxycarbonylamino]ethyl group, 2-(N-benzyl-N-isobutyloxycarbonylamino)ethyl group, 2-[N—(N-cyclopentylcarbamoyl)-N-methylamino]ethyl group, 2-[N-butyl-N—(N-cyclopentylcarbamoyl)amino]ethyl group, 2-[N—(N-cyclopentylcarbamoyl)-N-isobutylamino]ethyl group, 2-[N-cyclopentyl-N—(N-cyclopentylcarbamoyl)amino]ethyl group, 2-[N-cyclohexylmethyl-N—(N-cyclopentylcarbamoyl)amino]ethyl group, 2-[N—(N-cyclopentylcarbamoyl)-N-phenylamino]ethyl group, 2-[N-benzyl-N—(N-cyclopentylcarbamoyl)amino]ethyl group, 2-[N—(N-cyclohexylthiocarbamoyl)-N-methylamino]ethyl group, 2-[N-butyl-N—(N-cyclohexylthiocarbamoyl)amino]ethyl group, 2-[N—(N-cyclohexylthiocarbamoyl)-N-isobutylamino]ethyl group, 2-[N—(N-cyclohexylthiocarbamoyl)-N-cyclopentylamino]ethyl group, 2-[N-cyclohexylmethyl-N—(N-cyclohexylthiocarbamoyl)amino]ethyl group, 2-[N—(N-cyclohexylthiocarbamoyl)-N-phenylamino]ethyl group, 2-[N-benzyl-N—(N-cyclohexylthiocarbamoyl)amino]ethyl group, 2-(N-methyl-N-phenyloxycarbonylamino)ethyl group, 2-(N-butyl-N-phenyloxycarbonylamino)ethyl group, 2-(N-isobutyl-N-phenyloxycarbonylamino)ethyl group, 2-(N-cyclopentyl-N-phenyloxycarbonylamino)ethyl group, 2-(N-cyclohexylmethyl-N-phenyloxycarbonylamino)ethyl group, 2-(N-phenyl-N-phenyloxycarbonylamino)ethyl group, 2-(N-benzyl-N-phenyloxycarbonylamino)ethyl group, 2-[N-methyl-N—(N-phenylcarbamoyl)amino]ethyl group, 2-[N-butyl-N—(N-phenylcarbamoyl)amino]ethyl group, 2-[N-isobutyl-N—(N-phenylcarbamoyl)amino]ethyl group, 2-[N-cyclopentyl-N—(N-phenylcarbamoyl)amino]ethyl group, 2-[N-cyclohexylmethyl-N—(N-phenylcarbamoyl)amino]ethyl group, 2-[N-phenyl-N—(N-phenylcarbamoyl)amino]ethyl group, 2-[N-benzyl-N—(N-phenylcarbamoyl)amino]ethyl group, and the like.

When Rs in the formula (I) represents —N(Ry)(Rz), Rz is defined to have the same meaning as Rx, or Rz represents methyl group, ethyl group, or a -$A^5$-Re group. -$A^5$-Re has the same meaning as defined above.

Particularly preferred examples of Rz include butyl group, isobutyl group, 2-ethylbutyl group, cyclopentyl group, cyclohexyl group, cycloheptyl group, cyclopentylmethyl group, cyclohexylmethyl group, 2-methylphenyl group, 4-methylphenyl group, 2-fluorophenyl group, 3-fluorophenyl group, 4-fluorophenyl group, 2-chlorophenyl group, 3-chlorophenyl group, 4-chlorophenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, 1-phenylethyl group, 1-(2-fluorophenyl)ethyl group, 1-(3-fluorophenyl)ethyl group, 1-(4-fluorophenyl)ethyl group, 1-(2-chlorophenyl)ethyl group, 1-(3-chlorophenyl)ethyl group, 1-(4-chlorophenyl)ethyl group, 2-methylphenylmethyl group, 3-methylphenylmethyl group, 4-methylphenylmethyl group, 2,3-dimethylphenylmethyl group, 3,5-dimethylphenylmethyl group, 2-fluorophenylmethyl group, 3-fluorophenylmethyl group, 4-fluorophenylmethyl group, 2-chlorophenylmethyl group, 3-chlorophenylmethyl group, 4-chlorophenylmethyl group, 2,3-difluorophenylmethyl group, 2,4-difluorophenylmethyl group, 2,51-difluorophenylmethyl group, 3,4-difluorophenylmethyl group, 2,3-dichlorophenylmethyl group, 2,4-dichlorophenylmethyl group, 2,5-dichlorophenylmethyl group, 2,6-dichlorophenylmethyl group, 3,4-dichlorophenylmethyl group, 3,5-dichlorophenylmethyl group, 3,6-dichlorophenylmethyl group, 2-(trifluoromethyl)phenylmethyl group, 3-(trifluoromethyl)phenylmethyl group, 4-(trifluoromethyl)phenylmethyl group, 2-(2-methylphenyl)ethyl group, 2-(3-methylphenyl)ethyl group, 2-(4-methylphenyl)ethyl group, 2-(2-methoxyphenyl)ethyl group, 2-(3-methoxyphenyl)ethyl group, 2-(4-methoxyphenyl)ethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-[2-(trifluoromethyl)phenyl]ethyl group, 2-[3-(trifluoromethyl)phenyl]ethyl group, 2-[4-(trifluoromethyl)phenyl]ethyl group, 2-[4-(N,N-dimethylamino)phenyl]ethyl group, 2-phenyloxyethyl group, 2-(2-chlorophenyloxy)ethyl group, 2-(3-chlorophenyloxy)ethyl group, 2-(4-chlorophenyloxy)ethyl group, 2-(phenylthio)ethyl group, 2-(N-phenyl-N-methylamino)ethyl group, 2-(N-ethyl-N-phenylamino)ethyl group, isobutyryl group, isopropylthiocarbonyl group, isopropylsulfonyl group, valeryl group, butylthiocarbonyl group, isovaleryl group, isobutylthiocarbonyl group, pivaloyl group, t-butylthiocarbonyl group, cyclopropylcarbonyl group, cyclopropylthiocarbonyl group, cyclopentylcarbonyl group, cyclopentylthiocarbonyl group, cyclohexylcarbonyl group, cyclohexylthiocarbonyl group, cyclopentylmethylcarbonyl group, cyclopentylmethylthiocarbonyl group, cyclohexylmethylcarbonyl group, cyclohexylmethylthiocarbonyl group, benzoyl group, thiobenzoyl group, phenylsulfonyl group, 4-methylphenylcarbonyl group, 4-methylphenylthiocarbonyl group, 4-methylphenylsulfonyl group, 4-chlorophenylcarbonyl group, 4-chlorophenylthiocarbonyl group, 4-fluorophenylcarbonyl group, 4-fluorophenylthiocarbonyl group, isopropyloxycarbonyl group, N-isopropylcarbamoyl group, N-isopropylthiocarbamoyl group, butyloxycarbonyl group, N-butylcarbamoyl group, N-butylthiocarbamoyl group, isobutyloxycarbonyl group, N-isobutylcarbamoyl group, N-isobutylthiocarbamoyl group, t-butyloxycarbonyl group, N-t-butylcarbamoyl group, N-t-butylthiocarbamoyl group, cyclopropyloxycarbonyl group, N-cycloprop ylcarbamoyl group, N-cyclopropylthiocarbamoyl group, cyclopentyloxycarbonyl group, N-cyclopentylcarbamoyl group, N-cyclopentylthiocarbamoyl group, cyclohexyloxycarbonyl group, N-cyclohexylcarbamoyl group, N-cyclohexylthiocarbamoyl group, cyclopentylmethyloxycarbonyl group, cyclohexylmethyloxycarbonyl group, phenyloxycarbonyl group, N-phenylcarbamoyl group, N-phenylthiocarbamoyl group, 4-methylphenyloxycarbonyl group, N-(4-methylphenyl)carbamoyl group, N-(4-methylphenyl)thiocarbamoyl group, 4-chlorophenyloxycarbonyl group, N-(4-chlorophenyl)carbamoyl group, N-(4-chlorophenyl)thiocarbamoyl group, 4-fluorophenyloxycarbonyl group, N-(4-fluorophenyl)carbamoyl group, N-(4-fluorophenyl)thiocarbamoyl group, (pyrrolidino-1-yl)carbonyl group, (piperidino-1-yl)carbonyl group, (morpholino-4-yl)carbonyl group, and the like.

Among the Rz, methyl group or ethyl group is particularly preferred when Ry is other than hydrogen atom.

Ry represents hydrogen atom, an alkyl group having 1 to 8 carbon atoms, or a $-A^6-Qp$ group, or binds to Rz to form a saturated or unsaturated nitrogen-containing cyclic substituent having 3 to 7 atoms together with nitrogen atom to which they bind. The alkyl group having 1 to 8 carbon atoms is a linear or branched saturated alkyl group, a linear or branched partially unsaturated alkyl group, or an alkyl group which may contain a cyclic alkyl group having 3 to 7 carbon atoms. Examples include methyl group, ethyl group, propyl group, isopropyl group, butyl group, isobutyl group, t-butyl group, pentyl group, isopentyl group, 2-methylbutyl group, 2,2-dimethylpropyl group, hexyl group, 4-methylpentyl group, 2,3-dimethylbutyl group, 2-ethylbutyl group, heptyl group, octyl group, cyclopropyl group, cyclobutyl group, cyclopentyl group, cyclohexyl group, cycloheptyl group, cyclopropylmethyl group, cyclobutylmethyl group, cyclopentylmethyl group, cyclohexylmethyl group, cycloheptylmethyl group, 2-cyclopentylethyl group, 2-cyclohexylethyl group, 2-methylcyclopentyl group, 3-methylcyclopentyl group, 3,4-dimethylcyclopentyl group, 4-methylcyclohexyl group, 4,4-dimethylcyclohexyl group, 4-ethylcyclohexyl group, 4-methylcyclohexylmethyl group, and the like. $-A^6-Qp$ has the same meaning as defined above.

Particularly preferred examples of Ry include hydrogen atom, methyl group, ethyl group, isobutyl group, and the like.

Ry also binds to Rz to represents a saturated or unsaturated nitrogen-containing cyclic substituent having 3 to 7 atoms formed together with the nitrogen atom to which they bind. Specific examples thereof include cyclic substituents containing nitrogen atom such as 1-pyrrolidino group, 1-piperidino group, 1-homopiperidino group, 1-piperazino group, 4-morpholino group, pyrrol-1-yl group, imidazol-1-yl group, and pyrazol-1-yl group, and all of these are preferred.

The nitrogen-containing cyclic substituent may be substituted with one or two lower alkyl groups having 1 to 4 carbon atoms wherein the two alkyl groups may be the same or different. Examples of the lower alkyl having 1 to 4 carbon atoms include methyl group, ethyl group, propyl group, isopropyl group, butyl group, isobutyl group, t-butyl group, and the like.

Among the substituent —N(Ry)(Rz), particularly preferred examples include N,N-dimethylamino group, N-ethyl-N-methylamino group, N,N-diethylamino group, N-methyl-N-propylamino group, N-ethyl-N-propylamino group, N-isopropyl-N-methylamino group, N-ethyl-N-isopropylamino group, N-butylamino group, N-butyl-N-methylamino group, N-butyl-N-ethylamino group, N-isobutylamino group, N-isobutyl-N-methylamino group, N-ethyl-N-isobutylamino group, N-(2-ethylbutyl)amino group, N-(2-ethylbutyl)-N-methylamino group, N-cyclopentylamino group, N-cyclopentyl-N-methylamino group, N-cyclohexylamino group, N-cyclohexyl-N-methylamino group, N-cycloheptylamino group, N-(cyclopentylmethyl)amino group, N-(cyclopentylmethyl)-N-methylamino group, N-(cyclohexylmethyl)amino group, N-(cyclohexylmethyl)-N-methylamino group, N-(2-methylphenyl)amino group, N-(4-methylphenyl)amino group, N-(2-fluorophenyl)amino group, N-(3-fluorophenyl)amino group, N-(4-fluorophenyl)amino group, N-(2-chlorophenyl)amino group, N-(3-chlorophenyl)amino group, N-(4-chlorophenyl)amino group, N-(indan-2-yl)amino group, N-(1-phenylethyl)amino group, N-[1-(2-fluorophenyl)ethyl]amino group, N-[1-(3-fluorophenyl)ethyl]amino group, N-[1-(4-fluorophenyl)ethyl]amino group, N-[1-(2-chlorophenyl)ethyl]amino group, N-[1-(3-chlorophenyl)ethyl]amino group, N-[1-(4-chlorophenyl)ethyl]amino group, N-(2-methylphenylmethyl)amino group, N-methyl-N-(2-methylphenylmethyl)amino group, N-(3-methylphenylmethyl)amino group, N-methyl-N-(3-methylphenylmethyl)amino group, N-(4-methylphenylmethyl)amino group, N-methyl-N-(4-methylphenylmethyl)amino group, N-(2-fluorophenylmethyl)amino group, N-(2-fluorophenylmethyl)-N-methylamino group, N-(3-fluorophenylmethyl)amino group, N-(3-fluorophenylmethyl)-N-methylamino group, N-(4-fluorophenylmethyl)amino group, N-(4-fluorophenylmethyl)-N-methylamino group, N-(2-chlorophenylmethyl)amino group, N-(2-chlorophenylmethyl)-N-methylamino group, N-(3-chlorophenylmethyl)amino group, N-(3-chlorophenylmethyl)-N-methylamino group, N-(4-chlorophenylmethyl)amino group, N-(4-chlorophenylmethyl)-N-methylamino group, N-(2,3-difluorophenylmethyl)amino group, N-(2,3-difluorophenylmethyl)-N-methylamino group, N-(2,4-difluorophenylmethyl)amino group, N-(2,4-difluorophenylmethyl)-N-methylamino group, N-(2,5-difluorophenylmethyl)amino group, N-(2,5-difluorophenylmethyl)-N-methylamino group, N-(3,4-difluorophenylmethyl)amino group, N-(3,4-difluorophenylmethyl)-N-methylamino group, N-(3,5-difluorophenylmethyl)amino group, N-(3,5-difluorophenylmethyl)-N-methylamino group, N-(2,3-dichlorophenylmethyl)amino group, N-(2,3-dichlorophenylmethyl)-N-methylamino group, N-(2,4-dichlorophenylmethyl)amino group, N-(2,4-dichlorophenylmethyl)-N-methylamino group, N-(2,5-dichlorophenylmethyl)amino group, N-(2,5-dichlorophenylmethyl)-N-methylamino group, N-(2,6-dichlorophenylmethyl)amino group, N-(2,6-dichlorophenylmethyl)-N-methylamino group, N-(3,4-dichlorophenylmethyl)amino group, N-(3,4-dichlorophenylmethyl)-N-methylamino group, N-(3,5-dichlorophenylmethyl)amino group, N-(3,5-dichlorophenylmethyl)-N-methylamino group, N-[2-(trifluoromethyl)phenylmethyl]amino group, N-methyl-N-[2-(trifluoromethyl)phenylmethyl]amino group, N-[3-(trifluoromethyl)phenylmethyl]amino group, N-methyl-N-[3-(trifluoromethyl)phenylmethyl]amino group, N-[4-(trifluoromethyl)phenylmethyl]amino group, N-methyl-N-[4-(trifluoromethyl)phenylmethyl]amino group, 1-pyrrolidino group, 1-(4-methylpiperidino) group, 1-homopiperidino group, 4-morpholino group, and the like.

Particularly preferred examples of Rs in the aforementioned general formula (I) include Rs which meets the conditions of: Rs is -D-Rx wherein D is a single bond and Rx represents Rb, and $A^1$ and $A^2$ in Rb are single bonds. Specific examples of Rs include phenyl group, 2-methylphenyl group, 3-methylphenyl group, 4-methylphenyl group, 2,3-dimethylphenyl group, 3,5-dimethylphenyl group, 2-methoxyphenyl group, 3-methoxyphenyl group, 4-methoxyphenyl group, 2-fluorophenyl group, 3-fluorophenyl group, 4-fluorophenyl group, 2-chlorophenyl group, 3-chlorophenyl group, 4-chlorophenyl group, 2,3-difluorophenyl group, 2,4-difluorophenyl group, 2,5-difluorophenyl group, 3,4-difluorophenyl group, 2,3-dichlorophenyl group, 2,4-dichlorophenyl group, 2,5-dichlorophenyl group, 2,6-dichlorophenyl group, 3,4-dichlorophenyl group, 3,5-dichlorophenyl group, 2-trifluoromethylphenyl group, 3-trifluoromethylphenyl group, 4-trifluoromethylphenyl group, 4-(N,N-dimethylamino)phenyl group, indan-2-yl group, 4-methylindan-2-yl group, 5-methylindan-2-yl group, 4,7-dimethylindan-2-yl group, 5,6-dimethylindan-2-yl group, 4-fluoroindan-2-yl group, 5-fluoroindan-2-yl group, 4,7-difluoroindan-2-yl group, 5,6-difluoroindan-2-yl group, 4-chloroindan-2-yl group, 5-chloroindan-2-yl group, 4,7-dichloroindan-2-yl group, 5,6-dichloroindan-2-yl group, 4-methoxyindan-2-yl group, 5-methoxyindan-2-yl group, 4,7-dimethoxyindan-2-yl group, 5,6-dimethoxyindan-2-yl group, furan-2-yl group, furan-3-yl group, thiophen-2-yl group, thiophen-3-yl group, pyridin-2-yl group, pyridin-3-yl group, pyridin-4-yl group, naphthalen-1-yl group, naphthalen-2-yl group, 1H-indol-5-yl group, 1-methyl-1H-indol-5-yl group, 1H-indazol-5-yl group, 1-methyl-1H-indazol-5-yl group, and the like.

AR in the formula (I) is defined to be a residue of a partially unsaturated or completely unsaturated condensed bicyclic carbon ring or a heterocyclic ring (ar). Further, AR may be substituted with one of Xa or two or more of the same or different Xa. The heterocyclic ring (ar) means a ring containing 1 to 4 the same or different ring-constituting heteroatoms selected from the group consisting of nitrogen atom, oxygen atom, and sulfur atom.

The "condensed bicyclic carbon ring or heterocyclic ring" means a partially unsaturated or completely unsaturated ring having 8 to 11 atoms. Preferred examples include a partially unsaturated or completely unsaturated ring consisting of 8 atoms formed by fusion of 5-membered heterocyclic rings containing 1 or 2 ring-constituting heteroatoms selected from the group consisting of nitrogen, oxygen, and sulfur atoms, a partially unsaturated or completely unsaturated ring consisting of 9 atoms formed by fusion of a 5-membered heterocyclic ring containing 1 or 2 ring-constituting heteroatoms selected from the group consisting of nitrogen, oxygen, and sulfur atoms and a 6-membered carbon ring or a 6-membered heterocyclic ring containing 1 or 2 ring-constituting heteroatoms selected from the group consisting of nitrogen, oxygen, and sulfur atoms, and a partially unsaturated or completely unsaturated substituent consisting of 10 atoms formed by fusion of a 6-membered carbon ring or a 6-membered heterocyclic ring containing 1 or 2 ring-constituting heteroatoms selected from the group consisting of nitrogen, oxygen, and sulfur atoms and a 6-membered carbon ring or 6-membered heterocyclic rings containing 1 or 2 ring-constituting heteroatoms selected from the group consisting of nitrogen, oxygen, and sulfur atom. As the carbon ring constituting AR not containing a heteroatom, among the rings constituting AR, naphthalene ring is particularly preferred. Further, as the heterocyclic ring (ar) containing a heteroatom, among the rings constituting AR, those containing 1 or 2 ring-constituting heteroatoms are preferred.

As for AR in the formula (I), specific examples of preferred ring constituting AR include naphthalene, benzofuran, benzo[b]thiophene, indole, benzothiazole, dihydro-3H-benzothiazole, quinoline, dihydro-1H-quinoline, benzo[d]isothiazole, 1H-indazole, benzo[c]isothiazole, 2H-indazole, imidazo[1,2-a]pyridine, 1H-pyrrolo[2,3-b]pyridine, isoquinoline, dihydro-2H-isoquinoline, cinnoline, quinazoline, quinoxaline, 1H-benzimidazole, benzoxazole, 1H-pyrrolo[3,2-b]pyridine, benzo[1,2,5] thiadiazole, 1H-benzotriazole, 1,3-dihydropyrrolo[2,3-b]pyridine, 1,3-dihydrobenzimidazole, dihydro-3H-benzoxazole, phthalazine, [1,8]naphthylidine, [1,5]naphthylidine, 1H-pyrrolo[3,2-c]pyridine, 1H-pyrrolo[2,3-c]

pyridine, 1H-pyrazolo[4,3-b]pyridine, 1H-pyrazolo[4,3-c]pyridine, 1H-pyrazolo[3,4-c]pyridine, 1H-pyrazolo[3,4-b]pyridine, [1,2,4]triazolo[4,3-a]pyridine, thieno[3,2-c]pyridine, thieno[3,2-b]pyridine, 1H-thieno[3,2-c]pyrazole, benzo[d]isoxazole, benzo[c]isoxazole, indolizine, 1,3-dihydroindole, 1H-pyrazolo[3,4-d]thiazole, 2H-isoindole, [1,2,4]triazolo[1,5-a]pyrimidine, 1H-pyrazolo[3,4-b]pyrazine, 1H-imidazo[4,5-b]pyrazine, 7H-purine, 4H-chromene, and the like. Among them, naphthalene, benzofuran, benzo[b]thiophene, indole, benzothiazole, dihydro-3H-benzothiazole, quinoline, dihydro-1H-quinoline, benzo[d]isothiazole, 1H-indazole, benzo[c]isothiazole, 2H-indazole, imidazo[1,2-a]pyridine, 1H-pyrrolo[2,3-b]pyridine, isoquinoline and dihydro-2H-isoquinoline constitute a particularly preferred group, and cinnoline, quinazoline, quinoxaline, 1H-benzimidazole, benzoxazole, 1H-pyrrolo[3,2-b]pyridine, benzo[1,2,5]thiadiazole, 1H-benzotriazole, 1,3-dihydropyrrolo[2,3-b]pyridine, 1,3-dihydrobenzimidazole and dihydro-3H-benzoxazole also constitute a particularly preferred group. Further, naphthalene, benzofuran, benzo[b]thiophene, indole, benzothiazole, quinoline, 1H-indazole and isoquinoline are particularly preferred. Naphthalene, indole, quinoline, isoquinoline and 1H-indazole constitute a especially preferred group.

AR binds to any of the ring-constituting carbon atoms $C^2$, $C^3$, $C^4$, $C^5$, and $C^6$ in the aromatic ring (E) in the aforementioned formula (I) at an arbitrary carbon atom in AR. Preferred examples of the ring constituting AR include, as indicated with substitution position in the aromatic ring (E), naphthalen-2-yl group, naphthalen-1-yl group, benzofuran-5-yl group, benzofuran-4-yl group, benzofuran-2-yl group, benzo[b]thiophen-5-yl group, benzo[b]thiophen-4-yl group, benzo[b]thiophen-2-yl group, indol-5-yl group, indol-4-yl group, indol-6-yl group, benzothiazol-6-yl group, benzothiazol-7-yl group, benzothiazol-5-yl group, benzothiazol-4-yl group, dihydro-3H-benzothiazol-6-yl group, dihydro-3H-benzothiazol-7-yl group, dihydro-3H-benzothiazol-5-yl group, dihydro-3H-benzothiazol-4-yl group, quinolin-6-yl group, quinolin-3-yl group, quinolin-5-yl group, quinolin-7-yl group, dihydro-1H-quinolin-6-yl group, dihydro-1H-quinolin-5-yl group, benzo[d]isothiazol-5-yl group, benzo[d]isothiazol-4-yl group, benzo[d]isothiazol-6-yl group, benzo[d]isothiazol-7-yl group, 1H-indazol-5-yl group, 1H-indazol-4-yl group, 1H-indazol-6-yl group, benzo[c]isothiazol-5-yl group, benzo[c]isothiazol-4-yl group, benzo[c]isothiazol-6-yl group, benzo[c]isothiazol-7-yl group, 2H-indazol-5-yl group, 2H-indazol-4-yl group, 2H-indazol-6-yl group, imidazo[1,2-a]pyridin-6-yl group, imidazo[1,2-a]pyridin-7-yl group, 1H-pyrrolo[2,3-b]pyridin-5-yl group, 1H-pyrrolo[2,3-b]pyridin-4-yl group, isoquinolin-6-yl group, isoquinolin-3-yl group, isoquinolin-5-yl group, isoquinolin-7-yl group, dihydro-2H-isoquinolin-6-yl group, dihydro-2H-isoquinolin-5-yl group, cinnolin-6-yl group, cinnolin-5-yl group, quinazolin-6-yl group, quinazolin-7-yl group, quinazolin-5-yl group, quinoxalin-2-yl group, quinoxalin-6-yl group, quinoxalin-5-yl group, 1H-benzimidazol-5-yl group, 1H-benzimidazol-4-yl group, benzoxazol-5-yl group, benzoxazol-6-yl group, benzoxazol-4-yl group, benzoxazol-7-yl group, 1H-pyrrolo[3,2-b]pyridin-5-yl group, 1H-pyrrolo[3,2-b]pyridin-6-yl group, benzo[1,2,5]thiadiazol-5-yl group, benzo[1,2,5]thiadiazol-4-yl group, 1H-benzotriazol-5-yl group, 1H-benzotriazol-4-yl group, 1,3-dihydropyrrolo[2,3-b]pyridin-5-yl group, 1,3-dihydropyrrolo[2,3-b]pyridin-4-yl group, 1,3-dihydrobenzimidazol-5-yl group, 1,3-dihydrobenzimidazol-4-yl group, dihydro-3H-benzoxazol-6-yl group, dihydro-3H-benzoxazol-7-yl group, dihydro-3H-benzoxazol-5-yl group, dihydro-3H-benzoxazol-4-yl group, phthalazin-6-yl group, phthalazin-5-yl group, [1,8]naphthylidine-3-yl group, [1,8]naphthylidine-4-yl group, [1,5]naphthylidine 3-yl group, [1,5]naphthylidine-4-yl group, 1H-pyrrolo[3,2-c]pyridin-6-yl group, 1H-pyrrolo[3,2-c]pyridin-4-yl group, 1H-pyrrolo[2,3-c]pyridin-5-yl group, 1H-pyrrolo[2,3-c]pyridin-4-yl group, 1H-pyrazolo[4,3-b]pyridin-5-yl group, 1H-pyrazolo[4,3-b]pyridin-6-yl group, 1H-pyrazolo[4,3-c]pyridin-6-yl group, 1H-pyrazolo[4,3-c]pyridin-4-yl group, 1H-pyrazolo[3,4-c]pyridin-5-yl group, 1H-pyrazolo[3,4-c]pyridin-4-yl group, 1H-pyrazolo[3,4-b]pyridin-5-yl group, 1H-pyrazolo[3,4-b]pyridin-4-yl group, [1,2,4]triazolo[4,3-a]pyridin-6-yl group, [1,2,4]triazolo[4,3-a]pyridin-7-yl group, thieno[3,2-c]pyridin-2-yl group, thieno[3,2-c]pyridin-3-yl group, thieno[3,2-c]pyridin-6-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 1H-thieno[3,2-c]pyrazol-5-yl group, 1H-thieno[3,2-c]pyrazol-4-yl group, benzo[d]isoxazol-5-yl group, benzo[d]isoxazol-4-yl group, benzo[d]isoxazol-6-yl group, benzo[d]isoxazol-7-yl group, benzo[c]isoxazol-5-yl group, benzo[c]isoxazol-4-yl group, benzo[c]isoxazol-6-yl group, benzo[c]isoxazol-7-yl group, indolizin-7-yl group, indolizin-6-yl group, indolizin-8-yl group, 1,3-dihydroindol-5-yl group, 1,3-dihydroindol-4-yl group, 1,3-dihydroindol-6-yl group, 1H-pyrazolo[3,4-d]thiazol-5-yl group, 2H-isoindol-5-yl group, 2H-isoindol-4-yl group, [1,2,4]triazolo[1,5-a]pyrimidin-6-yl group, 1H-pyrazolo[3,4-b]pyrazin-5-yl group, 1H-imidazo[4,5-b]pyrazin-5-yl group, 7H-purin-2-yl group, 4H-chromen-6-yl group, 4H-chromen-5-yl group, and the like. Among them, naphthalen-2-yl group, naphthalen-1-yl group, benzofuran-5-yl group, benzofuran-4-yl group, benzo[b]thiophen-5-yl group, benzo[b]thiophen-4-yl group, indol-5-yl group, indol-4-yl group, benzothiazol-6-yl group, benzothiazol-7-yl group, quinolin-6-yl group, quinolin-3-yl group, dihydro-1H-quinolin-6-yl group, benzo[d]isothiazol-5-yl group, 1H-indazol-5-yl group, 1H-indazol-4-yl group, imidazo[1,2-a]pyridin-6-yl group, 1H-pyrrolo[2,3-b]pyridin-5-yl group, isoquinolin-6-yl group, dihydro-2H-isoquinolin-6-yl group, cinnolin-6-yl group, benzoxazol-5-yl group, and the like constitute a particularly preferred group, and naphthalen-2-yl group, benzofuran-5-yl group, benzo[b]thiophen-5-yl group, indol-5-yl group, benzothiazol-6-yl group, quinolin-6-yl group, quinolin-3-yl group, benzo[d]isothiazol-5-yl group, 1H-indazol-5-yl group, imidazo[1,2-a]pyridin-6-yl group, 1H-pyrrolo[2,3-b]pyridin-5-yl group, isoquinolin-6-yl group, cinnolin-6-yl group, benzoxazol-5-yl group and the like are particularly preferred. In another embodiment, naphthalen-2-yl group, benzofuran-5-yl group, benzo[b]thiophen-5-yl group, indol-5-yl group, benzothiazol-6-yl group, quinolin-6-yl group, quinolin-3-yl group, isoquinolin-6-yl group, and 1H-indazol-5-yl group are particularly preferred. Among them, naphthalen-2-yl group, indol-5-yl group, quinolin-6-yl group, quinolin-3-yl group, isoquinolin-6-yl group, and 1H-indazol-5-yl group are most preferred.

Further, AR may be substituted with one of Xa or the same or different two or more of Xa. Examples of substitution position of Xa include a carbon atom of AR not bonding to the aromatic ring (E), and/or when nitrogen atom is present, that nitrogen atom.

The substituent Xa represents a linear or branched saturated alkyl group having 1 to 4 carbon atoms, a saturated cyclic alkyl group having 3 to 7 carbon atoms, oxo group, thioxo group, fluorine atom, chlorine atom, trifluoromethyl group, —$(CH_2)_rR^{14}$, —$OR^{10}$, —$N(R^{11})(R^{12})$, —$SO_2R^{13}$, or —$COR^{27}$. However, when nitrogen atom is present in AR, Xa which may substitute on the nitrogen atom represents a linear or branched saturated alkyl group having 1 to 4 carbon atoms, a saturated cyclic alkyl group having 3 to 7 carbon atoms, or —$(CH_2)_iR^{14}$.

Preferred examples of the substituent Xa are oxo group, thioxo group, fluorine atom, chlorine atom, and trifluoromethyl group.

Examples of the linear or branched saturated alkyl group having 1 to 4 carbon atoms as the substituent Xa include methyl group, ethyl group, propyl group, isopropyl group, butyl group, isobutyl group, t-butyl group, and the like, and among them, methyl group, ethyl group, and propyl group are particularly preferred.

Further, examples of the saturated cyclic alkyl group having 3 to 7 carbon atoms include cyclopropyl group, cyclobutyl group, cyclopentyl group, cyclohexyl group, cycloheptyl group, and the like.

—$(CH_2)_iR^{14}$ has the same meaning as defined above. Preferred examples are 2-hydroxyethyl group, carboxymethyl group, 2-carboxyethyl group, and N,N-dimethylcarbamoylmethyl group, and a particularly preferred example is 2-hydroxyethyl group.

$R^{10}$ in —$OR^{10}$ represents hydrogen atom, a lower alkyl group having 1 to 4 carbon atoms, or a —$(CH_2)_iR^{14}$ group, and among them, hydrogen atom is a particularly preferred example. Examples of the lower alkyl group having 1 to 4 carbon atoms include methyl group, ethyl group, propyl group, isopropyl group, butyl group, isobutyl group, t-butyl group, and the like. Among them, methyl group is particularly preferred. —$(CH_2)_iR^{14}$ has the same meaning as defined above. Therefore, preferred examples of —$OR^{10}$ are hydroxyl group, methoxy group, 2-hydroxyethyloxy group, carboxymethyloxy group, 2-carboxyethyloxy group, N,N-dimethylcarbamoylmethyloxy group, and the like, and hydroxyl group, methoxy group, and 2-hydroxyethyloxy group are particularly preferred.

$R^{11}$ in —$N(R^{11})(R^{12})$ represents hydrogen atom, or a lower alkyl group having 1 to 4 carbon atoms, and $R^{12}$ represents hydrogen atom, a lower alkyl group having 1 to 4 carbon atoms, a hydroxyalkyl group having 2 to 4 carbon atoms, —$COR^{15}$, or —$SO_2R^{16}$, or binds to $R^{11}$ to form a 3- to 6-membered ring together with the nitrogen atom to which they bind to form a saturated nitrogen-containing cycloalkyl group or morpholino group. $R^{15}$ in —$COR^{15}$ represents a lower alkyl group having 1 to 4 carbon atoms, a hydroxyalkyl group having 2 to 4 carbon atoms, amino group, a mono- or dialkylamino group having 1 to 4 carbon atoms, or -$A^6$-Qa. $R^{16}$ in $SO_2R^{16}$ represents a lower alkyl group having 1 to 4 carbon atoms, amino group, or a mono- or dialkylamino group having 1 to 4 carbon atoms. Specific examples of —$N(R^{11})(R^{12})$ include amino group, N-methylamino group, N-ethylamino group, N-propylamino group, N-isopropylamino group, N,N-dimethylamino group, N,N-diethylamino group, piperidino group, pyrrolidino group, morpholino group, 2-hydroxyethylamino group, formylamino group, acetylamino group, benzoyl group, furan-2-carboxyamino group, 2-hydroxyacetylamino group, 2-aminoacetylamino group, carbamoylamino group, N-methylcarbamoylamino group, N,N-dimethylcarbamoylamino group, methylsulfonylamino group, sulfamoylamino group, N-methylsulfamoylamino group, N,N-dimethylsulfamoylamino group, and the like. Among them, preferred examples are amino group, methylamino group, dimethylamino group, 2-hydroxyethylamino group, carbamoylamino group, acetylamino group, furan-2-carboxyamino group, 2-hydroxyacetylamino group, 2-aminoacetylamino group, methylsulfonylamino group, (N,N-dimethylsulfamoyl)amino group, and the like, and amino group, N-methylamino group, N,N-dimethylamino group, and 2-hydroxyethylamino group are particularly preferred.

$R^{13}$ in —$SO_2R^{13}$ represents a lower alkyl group having 1 to 4 carbon atoms, amino group, or a mono- or dialkylamino group having 1 to 4 carbon atoms. Preferred examples of —$SO_2R^{13}$ include methanesulfonyl group, sulfamoyl group, N-methylsulfamoyl group, N,N-dimethylsulfamoyl group, and the like.

$R^{27}$ in —$COR^{27}$ represents hydrogen atom, hydroxyl group, an alkoxy group having 1 to 4 carbon atoms, a lower alkyl group having 1 to 4 carbon atoms, amino group, or a mono- or dialkylamino group having 1 to 4 carbon atoms. Specific examples of —$COR^{27}$ include formyl group, carboxyl group, methoxycarbonyl group, ethoxycarbonyl group, acetyl group, propionyl group, carbamoyl group, N-methylcarbamoyl group, N,N-dimethylcarbamoyl group, and the like. Carboxyl group, acetyl group, carbamoyl group, N,N-dimethylcarbamoyl group, and the like are preferred examples, and carboxyl group is particularly preferred.

Preferred examples of the group Xa include oxo group, thioxo group, fluorine atom, chlorine atom, trifluoromethyl group, methyl group, ethyl group, propyl group, 2-hydroxyethyl group, carboxymethyl group, 2-carboxyethyl group, N,N-dimethylcarbamoylmethyl group, hydroxyl group, methoxy group, 2-hydroxyethyloxy group, carboxymethyloxy group, 2-carboxyethyloxy group, N,N-dimethylcarbamoylmethyloxy group, amino group, methylamino group, dimethylamino group, 2-hydroxyethylamino group, carbamoylamino group, acetylamino group, furan-2-carboxyamino group, 2-hydroxyacetylamino group, 2-aminoacetylamino group, methylsulfonylamino group, (N,N-dimethylsulfamoyl)amino group, methanesulfonyl group, sulfamoyl group, N-methylsulfamoyl group, N,N-dimethylsulfamoyl group, carboxyl group, acetyl group, carbamoyl group, N,N-dimethylcarbamoyl group, and the like. Particularly preferred examples of the group Xa include oxo group, methyl group, ethyl group, propyl group, 2-hydroxyethyl group, hydroxyl group, methoxy group, 2-hydroxyethyloxy group, amino group, N-methylamino group, N,N-dimethylamino group, 2-hydroxyethylamino group, carboxyl group, and the like. Preferred examples of the group Xa which may substitute on nitrogen atom include methyl group, ethyl group, propyl group, hydroxymethyl group, 2-hydroxyethyl group, carboxymethyl group, 2-carboxyethyl group, and N,N-dimethylcarbamoylmethyl group. Among them, particularly preferred examples are methyl group, ethyl group, propyl group, and 2-hydroxyethyl group.

Preferred examples of AR substituted with the group Xa or unsubstituted AR include naphthalen-1-yl group, naphthalen-2-yl group, 6-fluoronaphthalen-2-yl group, 6-chloronaphthalen-2-yl group, 6-(trifluoromethyl)naphthalen-2-yl group, 5-hydroxynaphthalen-1-yl group, 5-hydroxynaphthalen-2-yl group, 6-hydroxynaphthalen-1-yl group, 6-hydroxynaphthalen-2-yl group, 7-hydroxynaphthalen-1-yl group, 7-hydroxynaphthalen-2-yl group, 5-methoxynaphthalen-1-yl group, 5-methoxynaphthalen-2-yl group, 6-methoxynaphthalen-1-yl group, 6-methoxynaphthalen-2-yl group, 7-methoxynaphthalen-1-yl group, 7-methoxynaphthalen-2-yl group, 5-(2-hydroxyethyloxy)naphthalen-2-yl group, 6-(2-hydroxyethyloxy)naphthalen-2-yl group, 7-(2-hydroxyethyloxy)naphthalen-2-yl group, 5-(carboxymethyloxy)naphthalen-2-yl group, 6-(carboxymethyloxy)naphthalen-2-yl group, 7-(carboxymethyloxy) naphthalen-2-yl group, 5-(N,N-dimethylcarbamoylmethyloxy)naphthalen-2-yl group, 6-(N,N-dimethylcarbamoylmethyloxy)naphthalen-2-yl group, 7-(N, N-dimethylcarbamoylmethyloxy)naphthalen-2-yl group, 5-aminonaphthalen-1-yl group, 5-aminonaphthalen-2-yl group, 6-aminonaphthalen-1-yl group, 6-aminonaphthalen-2-yl group, 7-aminonaphthalen-1-yl group, 7-aminonaphthalen-2-yl group, 5-(N-methylamino)naphthalen-1-yl group, 5-(N-methylamino)naphthalen-2-yl group, 6-(N-methylamino)naphthalen-1-yl group, 6-(N-methylamino)naphthalen-2-yl group, 7-(N-methylamino)naphthalen-1-yl group, 7-(N-methylamino)naphthalen-2-yl group, 5-(N,N-dimethylamino)naphthalen-1-yl group, 5-(N,N-dimethylamino)naphthalen-2-yl group, 6-(N,N-dimethylamino)naphthalen-1-yl group, 6-(N,N-dimethylamino)naphthalen-2-yl group, 7-(N,N-dimethylamino)naphthalen-1-yl group, 7-(N,N-dimethylamino)naphthalen-2-yl group, 5-(2-hydroxyethylamino)naphthalen-2-yl group, 6-(2-hydroxyethylamino)naphthalen-2-yl group, 7-(2-hydroxyethylamino)naphthalen-2-yl group, 5-acetylaminonaphthalen-2-yl group, 6-acetylaminonaphthalen-2-yl group, 6-(2-aminoacetylamino)naphthalen-2-yl group, 6-(2-hydroxyacetylamino)naphthalen-2-yl group, 7-(2-hydroxyacetylamino)naphthalen-2-yl group, 6-[(furan-2-carbonyl)amino]naphthalen-2-yl group, 7-[(furan-2-carbonyl)amino]naphthalen-2-yl group, 6-[(benzene-2-carbonyl)amino]naphthalen-2-yl group, 7-[(benzene-2-carbonyl)amino]naphthalen-2-yl group, 6-carbamoylaminonaphthalen-2-yl group, 6-methylsulfonylaminonaphthalen-2-yl group, 6-sulfamoylaminonaphthalen-2-yl group, 6-(N,N-dimethylsulfamoylamino)naphthalen-2-yl group, 6-methanesulfonylnaphthalen-2-yl group, 6-sulfamoylnaphthalen-2-yl group, 6-(N-methylsulfamoyl)naphthalen-2-yl group, 6-(N,N-dimethylsulfamoyl)naphthalen-2-yl group, 6-carboxynaphthalen-2-yl group, benzo[b]furan-4-yl group, benzo[b]furan-5-yl group, 2-methylbenzo[b]furan-4-yl group, 2-methylbenzo[b]furan-5-yl group, 3-methylbenzo[b]furan-4-yl group, 3-methylbenzo[b]furan-5-yl group, 2,3-dimethylbenzo[b]furan-4-yl group, 2,3-dimethylbenzo[b]furan-5-yl group, 2-carboxybenzo[b]furan-4-yl group, 2-carboxybenzo[b]furan-5-yl group, 2-carboxy-3-methylbenzo[b]furan-4-yl group, 2-carboxy-3-methylbenzo[b]furan-5-yl group, 3-acetylbenzo[b]furan-4-yl group, 3-acetylbenzo[b]furan-5-yl group, 3-acetyl-2-methylbenzo[b]furan-4-yl group, 3-acetyl-2-methylbenzo[b]furan-5-yl group, 3-hydroxymethylbenzo[b]furan-4-yl group, 3-hydroxymethylbenzo[b]furan-5-yl group, 3-hydroxymethyl-2-methylbenzo[b]furan-4-yl group, 3-hydroxymethyl-2-methylbenzo[b]furan-5-yl group, benzo[b]thiophen-4-yl group, benzo[b]thiophen-5-yl group, 2-methylbenzo[b]thiophen-4-yl group, 2-methylbenzo[b]thiophen-5-yl group, 3-methylbenzo[b]thiophen-4-yl group, 3-methylbenzo[b]thiophen-5-yl group, 2,3-dimethylbenzo[b]thiophen-4-yl group, 2,3-dimethylbenzo[b]thiophen-5-yl group, 2-carboxybenzo[b]thiophen-4-yl group, 2-carboxybenzo[b]thiophen-5-yl group, 2-carboxy-3-methylbenzo[b]thiophen-4-yl group, 2-carboxy-3-methylbenzo[b]thiophen-5-yl group, 3-acetylbenzo[b]thiophen-4-yl group, 3-acetylbenzo[b]thiophen-5-yl group, 3-acetyl-2-methylbenzo[b]thiophen-4-yl group, 3-acetyl-2-methylbenzo[b]thiophen-5-yl group, 3-hydroxymethylbenzo[b]thiophen-4-yl group, 3-hydroxymethylbenzo[b]thiophen-5-yl group, 3-hydroxymethyl-2-methylbenzo[b]thiophen-4-yl group, 3-hydroxymethyl-2-methylbenzo[b]thiophen-5-yl group, 1H-indol-4-yl group, 1H-indol-5-yl group, 2-methyl-1H-indol-4-yl group, 2-methyl-1H-indol-5-yl group, 3-methyl-1H-indol-4-yl group, 3-methyl-1H-indol-5-yl group, 2,3-dimethyl-1H-indol-4-yl group, 2,3-dimethyl-1H-indol-5-yl group, 2-carboxy-1H-indol-4-yl group, 2-carboxy-1H-indol-5-yl group, 2-carboxy-3-methyl-1H-indol-4-yl group, 2-carboxy-3-methyl-1H-indol-5-yl group, 3-acetyl-1H-indol-4-yl group, 3-acetyl-1H-indol-5-yl group, 3-acetyl-2-methyl-1H-indol-4-yl group, 3-acetyl-2-methyl-1H-indol-5-yl group, 3-hydroxymethyl-1H-indol-4-yl group, 3-hydroxymethyl-1H-indol-5-yl group, 3-hydroxymethyl-2-methyl-1H-indol-4-yl group, 3-hydroxymethyl-2-methyl-1H-indol-5-yl group, 1-methyl-1H-indol-4-yl group, 1-methyl-1H-indol-5-yl group, 1,2-dimethyl-1H-indol-4-yl group, 1,2-dimethyl-1H-indol-5-yl group, 1,3-dimethyl-1H-indol-4-yl group, 1,3-dimethyl-1H-indol-5-yl group, 1,2,3-trimethyl-1H-indol-4-yl group, 1,2,3-trimethyl-1H-indol-5-yl group, 2-carboxy-1-methyl-1H-indol-4-yl group, 2-carboxy-1-methyl-1H-indol-5-yl group, 2-carboxy-1,3-dimethyl-1H-indol-4-yl group, 2-carboxy-1,3-dimethyl-1H-indol-5-yl group, 3-acetyl-1-methyl-1H-indol-4-yl group, 3-acetyl-1-methyl-1H-indol-5-yl group, 3-acetyl-1,2-dimethyl-1H-indol-4-yl group, 3-acetyl-1,2-dimethyl-1H-indol-5-yl group, 3-hydroxymethyl-1-methyl-1H-indol-4-yl group, 3-hydroxymethyl-1-methyl-1H-indol-5-yl group, 3-hydroxymethyl-1,2-dimethyl-1H-indol-4-yl group, 3-hydroxymethyl-1,2-dimethyl-1H-indol-5-yl group, 1-ethyl-1H-indol-4-yl group, 1-ethyl-1H-indol-5-yl group, 1-ethyl-2-methyl-1H-indol-4-yl group, 1-ethyl-2-methyl-1H-indol-5-yl group, 1-ethyl-3-methyl-1H-indol-4-yl group, 1-ethyl-3-methyl-1H-indol-5-yl group, 1-ethyl-2,3-dimethyl-1H-indol-4-yl group, 1-ethyl-2,3-dimethyl-1H-indol-5-yl group, 2-carboxy-1-ethyl-1H-indol-4-yl group, 2-carboxy-1-ethyl-1H-indol-5-yl group, 2-carboxy-1-ethyl-3-methyl-1H-indol-4-yl group, 2-carboxy-1-ethyl-3-methyl-1H-indol-5-yl group, 3-acetyl-1-ethyl-1H-indol-4-yl group, 3-acetyl-1-ethyl-1H-indol-5-yl group, 3-acetyl-1-ethyl-2-methyl-1H-indol-4-yl group, 3-acetyl-1-ethyl-2-methyl-1H-indol-5-yl group, 1-ethyl-3-hydroxymethyl-1H-indol-4-yl group, 1-ethyl-3-hydroxymethyl-1-indol-5-yl group, 1-ethyl-3-hydroxymethyl-2-methyl-1H-indol-4-yl group, 1-ethyl-3-hydroxymethyl-2-methyl-1H-indol-5-yl group, 1-propyl-1H-indol-4-yl group, 1-propyl-1H-indol-5-yl group, 2-methyl-1-propyl-1H-indol-4-yl group, 2-methyl-1-propyl-1H-indol-5-yl group, 3-methyl-1-propyl-1H-indol-4-yl group, 3-methyl-1-propyl-1H-indol-5-yl group, 2,3-dimethyl-1-propyl-1H-indol-4-yl group, 2,3-dimethyl-1-propyl-1H-indol-5-yl group, 2-carboxy-1-propyl-1H-indol-4-yl group, 2-carboxy-1-propyl-1H-indol-5-yl group, 2-carboxy-3-methyl-1-propyl-1H-indol-4-yl group, 2-carboxy-3-methyl-1-propyl-1H-indol-5-yl group, 3-acetyl-1-propyl-1H-indol-4-yl group, 3-acetyl-1-propyl-1H-indol-5-yl group, 3-acetyl-2-methyl-1-propyl-1H-indol-4-yl group, 3-acetyl-2-methyl-1-propyl-1H-indol-5-yl group, 3-hydroxymethyl-1-propyl-1H-indol-4-yl group, 3-hydroxymethyl-1-propyl-1H-indol-5-yl group, 3-hydroxymethyl-2-methyl-1-propyl-1H-indol-4-yl group, 3-hydroxymethyl-2-methyl-1-propyl-1H-indol-5-yl group, 1-(2-hydroxyethyl)-1H-indol-4-yl group, 1-(2-hydroxyethyl)-1H-indol-5-yl group, 1-(2-hydroxyethyl)-2-methyl-1H-indol-4-yl group, 1-(2-hydroxyethyl)-2-methyl-1H-indol-5-yl group, 1-(2-hydroxyethyl)-3-methyl-1H-indol-4-yl group, 1-(2-hydroxyethyl)-3-methyl-1H-indol-5-yl group, 2,3-dimethyl-1-(2-hydroxyethyl)-1H-indol-4-yl group, 2,3-dimethyl-1-(2-hydroxyethyl)-1H-indol-5-yl group, 2-carboxy-1-(2-hydroxyethyl)-1H-indol-4-yl group, 2-carboxy-1-(2-hydroxyethyl)-1H-indol-5-yl group, 2-carboxy-1-(2-hydroxyethyl)-3-methyl-1H-indol-4-yl group, 2-carboxy-1-(2-hydroxyethyl)-3-methyl-1H-indol-5-yl group, 3-acetyl-1-(2-hydroxyethyl)-1H-indol-4-yl group, 3-acetyl-1-(2-hydroxyethyl)-2-1H-indol-5-yl group, 3-acetyl-1-(2-hydroxyethyl)-2-methyl-1H-indol-4-yl group, 3-acetyl-1-(2-hydroxyethyl)-2-methyl-1H-indol-5-yl group, 1-(2-hydroxyethyl)-3-hydroxymethyl-1H-indol-4-yl group, 1-(2-hydroxyethyl)-3-hydroxymethyl-1H-indol-5-yl group, 1-(2-hydroxyethyl)-3-hydroxymethyl-2-methyl-1H-indol-4- yl group, 1-(2-hydroxyethyl)-3-hydroxymethyl-2-methyl-1H-indol-5-yl group, 1-carboxymethyl-1H-indol-4-yl group, 1-carboxymethyl-1H-indol-5-yl group, 1-carboxymethyl-2-methyl-1H-indol-4-yl group, 1-carboxymethyl-2-methyl-1H-indol-5-yl group, 1-carboxymethyl-3-methyl-1H-indol-4-yl group, 1-carboxymethyl-3-methyl-1H-indol-5-yl group, 1-carboxymethyl-2,3-dimethyl-1H-indol-4-yl group, 1-carboxymethyl-2,3-dimethyl-1H-indol-5-yl group, 2-carboxy-1-carboxymethyl-1H-indol-4-yl group, 2-carboxy-1-carboxymethyl-1H-indol-5-yl group, 2-carboxy-1-carboxymethyl-3-methyl-1H-indol-4-yl group, 2-carboxy-1-carboxymethyl-3-methyl-1H-indol-5-yl group, 3-acetyl-1-carboxymethyl-1H-indol-4-yl group, 3-acetyl-1-carboxymethyl-1H-indol-5-yl group, 3-acetyl-1-carboxymethyl-2-methyl-1H-indol-4-yl group, 3-acetyl-1-carboxymethyl-2-methyl-1H-indol-5-yl group, 1-carboxymethyl-3-hydroxymethyl-1H-indol-4-yl group, 1-carboxymethyl-3-hydroxymethyl-1H-indol-5-yl group, 1-carboxymethyl-3-hydroxymethyl-2-methyl-1H-indol-4-yl group, 1-carboxymethyl-3-hydroxymethyl-2-methyl-1H-indol-5-yl group, benzothiazol-6-yl group, 2-methylbenzothiazol-6-yl group, 2-methoxybenzothiazol-6-yl group, 2-aminobenzothiazol-6-yl group, 2-(N-methylamino)benzothiazol-6-yl group, 2-(N,N-dimethylamino)benzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, 2-methylquinolin-3-yl group, quinolin-6-yl group, 2-methylquinolin-6-yl group, 2-oxo-1,2-dihydroquinolin-6-yl group, benzo[d]isothiazol-5-yl group, 3-methylbenzo[d]isothiazol-5-yl group, 1H-indazol-5-yl group, 3-methyl-1H-indazol-5-yl group, 1-methyl-1H-indazol-5-yl group, 1,3-dimethyl-1H-indazol-5-yl group, 1-ethyl-1H-indazol-5-yl group, 1-ethyl-3-methyl-1H-indazol-5-yl group, 1-propyl-1H-indazol-5-yl group, 3-methyl-1-propyl-1H-indazol-5-yl group, 1-(2-hydroxyethyl)-1H-indazol-5-yl group, 1-(2-hydroxyethyl)-3-methyl-1H-indazol-5-yl group, 1-(carboxymethyl)-1H-indazol-5-yl group, 1-(carboxymethyl)-3-methyl-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, benzo[c]isothiazol-5-yl group, 3-methylbenzo[c]isothiazol-5-yl group, 2-methyl-2H-indazol-5-yl group, 2,3-dimethyl-2H-indazol-5-yl group, 2-ethyl-2H-indazol-5-yl group, 2-ethyl-3-methyl-2H-indazol-5-yl group, 2-propyl-2H-indazol-5-yl group, 3-methyl-2-propyl-2H-indazol-5-yl group, 2-(2-hydroxyethyl)-2H-indazol-5-yl group, 2-(2-hydroxyethyl)-3-methyl-2H-indazol-5-yl group, 2-(carboxymethyl)-2H-indazol-5-yl group, 2-(carboxymethyl)-3-methyl-2H-indazol-5-yl group, imidazo[1,2-a]pyridin-6-yl group, 2-methylimidazo[1,2-a]pyridin-6-yl group, 3-methyl-imidazo[1,2-a]pyridin-6-yl group, 2,3-dimethyl-imidazo[1,2-a]pyridin-6-yl group, 1H-pyrrolo[2,3-b]pyridin-5-yl group, 2-methyl-1H-pyrrolo[2,3-b]pyridin-5-yl group, 3-methyl-1H-pyrrolo[2,3-b]pyridin-5-yl group, 1-methyl-1H-pyrrolo[2,3-b]pyridin-5-yl group, 1,2-dimethyl-1H-pyrrolo[2,3-b]pyridin-5-yl group, 1,3-dimethyl-1H-pyrrolo[2,3-b]pyridin-5-yl group, 2,3-dimethyl-1H-pyrrolo[2,3-b]pyridin-5-yl group, 1,2,3-trimethyl-1H-pyrrolo[2,3-b]pyridin-5-yl group, 1-ethyl-1H-pyrrolo[2,3-b]pyridin-5-yl group, 1-ethyl-2-methyl-1H-pyrrolo[2,3-b]pyridin-5-yl group, 1-ethyl-3-methyl-1H-pyrrolo[2,3-b]pyridin-5-yl group, 1-ethyl-2,3-dimethyl-1H-pyrrolo[2,3-b]pyridin-5-yl group, 1-propyl-1H-pyrrolo[2,3-b]pyridin-5-yl group, 2-methyl-1-propyl-1H-pyrrolo[2,3-b]pyridin-5-yl group, 3-methyl-1-propyl-1H-pyrrolo[2,3-b]pyridin-5-yl group, 2,3-dimethyl-1-propyl-1H-pyrrolo[2,3-b]pyridin-5-yl group, 1-(2-hydroxyethyl)-1H-pyrrolo[2,3-b]pyridin-5-yl group, 1-(2-hydroxyethyl)-2-methyl-1H-pyrrolo[2,3-b]pyridin-5-yl group, 1-(2-hydroxyethyl)-3-methyl-1H-pyrrolo[2,3-b]pyridin-5-yl group, 2,3-dimethyl-1-(2-hydroxyethyl)-1H-pyrrolo[2,3-b]pyridin-5-yl group, 1-(carboxymethyl)1H-pyrrolo[2,3-b]pyridin-5-yl group, 1-(carboxymethyl)-2-methyl-1H-pyrrolo[2,3-b]pyridin-5-yl group, 1-(carboxymethyl)-3-methyl-1H-pyrrolo[2,3-b]pyridin-5-yl group, 1-(carboxymethyl)-2,3-dimethyl-1H-pyrrolo[2,3-b]pyridin-5-yl group, isoquinolin-6-yl group, 1-methylisoquinolin-6-yl group, 1-oxo-1,2-dihydroisoquinolin-6-yl group, cinnolin-6-yl group, cinnolin-5-yl group, quinazolin-6-yl group, quinazolin-7-yl group, quinazolin-5-yl group, 2-methylquinazolin-6-yl group, quinoxalin-6-yl group, quinoxalin-5-yl group, 2-methylquinoxalin-6-yl group, 1H-benzimidazol-5-yl group, 1H-benzimidazol-4-yl group, 1-methyl-1H-benzimidazol-5-yl group, 2-methyl-1H-benzimidazol-5-yl group, 1,2-dimethyl-1H-benzimidazol-5-yl group, benzoxazol-5-yl group, benzoxazol-6-yl group, benzoxazol-4-yl group, benzoxazol-7-yl group, 2-methyl-benzoxazol-5-yl group, 1H-pyrrolo[3,2-b]pyridin-5-yl group, 1H-pyrrolo[3,2-b]pyridin-6-yl group, 1-methyl-1H-pyrrolo[3,2-b]pyridin-5-yl group, 1-ethyl-1H-pyrrolo[3,2-b]pyridin-5-yl group, 2-methyl-1H-pyrrolo[3,2-b]pyridin-5-yl group, 3-methyl-1H-pyrrolo[3,2-b]pyridin-5-yl group, 1,3-dimethyl-1H-pyrrolo[3,2-b]pyridin-5-yl group, benzo[1,2,5]thiadiazol-5-yl group, benzo[1,2,5]thiadiazol-4-yl group, 1H-benzotriazol-5-yl group, 1H-benzotriazol-4-yl group, 1-methyl-1H-benzotriazol-5-yl group, 1-ethyl-1H-benzotriazol-5-yl group, 1,3-dihydropyrrolo[2,3-b]pyridin-2-on-5-yl group, 1,3-dihydropyrrolo[2,3-b]pyridin-2-on-4-yl group, 1-methyl-1,3-dihydropyrrolo[2,3-b]pyridin-2-on-5-yl group, 1,3-dihydrobenzimidazol-2-on-5-yl group, 1,3-dihydrobenzimidazol-2-on-4-yl group, 1-methyl-1,3-dihydrobenzimidazol-2-on-5-yl group, 1,3-dihydrobenzimidazol-2-thion-5-yl group, 1,3-dihydrobenzimidazole-2-thion-4-yl group, 1-methyl-1,3-dihydrobenzimidazole-2-thion-5-yl group, 3H-benzoxazol-2-on-6-yl group, 3H-benzoxazol-2-on-7-yl group, 3H-benzoxazol-2-on-5-yl group, 3H-benzoxazol-2-on-4-yl group, 3-methyl-3H-benzoxazol-2-on-6-yl group, 3H-benzoxazole-2-thion-6-yl group, 3H-benzoxazole-2-thion-7-yl group, 3H-benzoxazole-2-thion-5-yl group, 3H-benzoxazole-2-thion-4-yl group, 3-methyl-3H-benzoxazole-2-thion-6-yl group, phthalazin-6-yl group, phthalazin-5-yl group, [1,8]naphthylidine-3-yl group, [1,8]naphthylidine-4-yl group, [1,5]naphthylidine-3-yl group, [1,5]naphthylidine-4-yl group, 1H-pyrrolo[3,2-c]pyridin-6-yl group, 1H-pyrrolo[3,2-c]pyridin-4-yl group, 1-methyl-1H-pyrrolo[3,2-c]pyridin-6-yl group, 1-ethyl-1H-pyrrolo[3,2-c]pyridin-6-yl group, 2-methyl-1H-pyrrolo[3,2-c]pyridin-6-yl group, 3-methyl-1H-pyrrolo[3,2-c]pyridin-6-yl group, 1,3-dimethyl-1H-pyrrolo[3,2-c]pyridin-6-yl group, 1H-pyrrolo[2,3-c]pyridin-5-yl group, 1H-pyrrolo[2,3-c]pyridin-4-yl group, 1-methyl-1H-pyrrolo[2,3-c]pyridin-5-yl group, 1-ethyl-1H-pyrrolo[2,3-c]pyridin-5-yl group, 2-methyl-1H-pyrrolo[2,3-c]pyridin-5-yl group, 3-methyl-1H-pyrrolo[2,3-c]pyridin-5-yl group, 1,3-dimethyl-1H-pyrrolo[2,3-c]pyridin-5-yl group, 1H-pyrazolo[4,3-b]pyridin-5-yl group, 1H-pyrazolo[4,3-b]pyridin-6-yl group, 1-methyl-1H-pyrazolo[4,3-b]pyridin-5-yl group, 1-ethyl-1H-pyrazolo[4,3-b]pyridin-5-yl group, 3-methyl-1H-pyrazolo[4,3-b]pyridin-5-yl group, 1,3-dimethyl-1H-pyrazolo[4,3-b]pyridin-5-yl group, 1H-pyrazolo[4,3-c]pyridin-6-yl group, 1H-pyrazolo[4,3-c]pyridin-4-yl group, 1-methyl-1H-pyrazolo[4,3-c]pyridin-6-yl group, 1-ethyl-1H-pyrazolo[4,3-c]pyridin-6-yl group, 3-methyl-1H-pyrazolo[4,3-c]pyridin-6-yl group, 1,3-dimethyl-1H-pyrazolo[4,3-c]pyridin-6-yl group, 1H-pyrazolo[3,4-c]pyridin-5-yl group, 1H-pyrazolo[3,4-c]pyridin-4-yl group, 1-methyl-1H-pyrazolo[3,4-c]pyridin-5-yl group, 1-ethyl-1H-pyrazolo[3,4-c]pyridin-5-yl group, 3-methyl-1H-pyrazolo[3,4-c]pyridin-5-yl group, 1,3-dimethyl-1H-pyrazolo[3,4-c]pyridin-5-yl group, 1H-pyrazolo[3,4-b]pyridin-5-yl group, 1H-pyrazolo[3,4-b]pyridin-4-yl group, 1-methyl-1H-pyrazolo[3,4-b]pyridin-5-yl group, 1-ethyl-1H-pyrazolo[3,4-b]pyridin-5-yl group, 3-methyl-1H-pyrazolo[3,4-b]pyridin-5-yl group, 1,3-dimethyl-1H-pyrazolo[3,4-b]pyridin-5-yl group, [1,2,4]triazolo[4,3-a]pyridin-6-yl group, [1,2,4]triazolo[4,3-a]pyridin-7-yl group, 3-methyl[1,2,4]triazolo[4,3-a]pyridin-6-yl group, thieno[3,2-c]pyridin-2-yl group, thieno[3,2-c]pyridin-3-yl group, thieno[3,2-c]pyridin-6-yl group, 2-methylthieno[3,2-c]pyridin-2-yl group, 3-methylthieno[3,2-c]pyridin-2-yl group, thieno[3,2-b]pyridin-2-yl group, thieno[3,2-b]pyridin-3-yl group, thieno[3,2-b]pyridin-5-yl group, thieno[3,2-b]pyridin-6-yl group, 2-methylthieno[3,2-b]pyridin-2-yl group, 3-methylthieno[3,2-b]pyridin-2-yl group, 1H-thieno[3,2-c]pyrazol-5-yl group, 1H-thieno[3,2-c]pyrazol-4-yl group, 1-methyl-1H-thieno[3,2-c]pyrazol-5-yl group, 1-ethyl-1H-thieno[3,2-c]pyrazol-5-yl group, 3-methyl-1H-thieno[3,2-c]pyrazol-5-yl group, 1,3-dimethyl-1H-thieno[3,2-c]pyrazol-5-yl group, benzo[d]isoxazol-5-yl group, benzo[d]isoxazol-4-yl group, benzo[d]isoxazol-6-yl group, benzo[d]isoxazol-7-yl group, 3-methylbenzo[d]isoxazol-5-yl group, benzo[c]isoxazol-5-yl group, benzo[c]isoxazol-4-yl group, benzo[c]isoxazol-6-yl group, benzo[c]isoxazol-7-yl group, 3-methylbenzo[c]isoxazol-5-yl group, indolizin-7-yl group, indolizin-6-yl group, indolizin-8-yl group, 1,3-dihydroindol-2-on-5-yl group, 1,3-dihydroindol-2-on-4-yl group, 1,3-dihydroindol-2-on-6-yl group, 1-methyl-1,3-dihydro-indol-2-on-5-yl group, 1H-pyrazolo[3,4-d]thiazol-5-yl group, 2H-isoindol-5-yl group, 2H-isoindol-4-yl group, 2-methyl-2H-isoindol-5-yl group, 4H-chromen-6-yl group, 4H-chromen-5-yl group, chromen-4-on-7-yl group, chromen-4-on-6-yl group, and the like.

Particularly preferred examples include naphthalen-2-yl group, 6-hydroxynaphthalen-2-yl group, 6-methoxynaphthalen-2-yl group, 6-(2-hydroxyethyloxy)naphthalen-2-yl group, 6-aminonaphthalen-2-yl group, 6-(N-methylamino)naphthalen-2-yl group, 6-(N,N-dimethylamino)naphthalen-2-yl group, 6-(2-hydroxyethylamino)naphthalen-2-yl group, benzo[b]furan-5-yl group, 2-methylbenzo[b]furan-5-yl group, 3-methylbenzo[b]furan-5-yl group, 2,3-dimethyl-benzo[b]furan-5-yl group, benzo[b]thiophen-5-yl group, 2-methylbenzo[b]thiophen-5-yl group, 3-methylbenzo[b]thiophen-5-yl group, 2,3-dimethylbenzo[b]thiophen-5-yl group, 1H-indol-5-yl group, 2-methyl-1H-indol-5-yl group, 3-methyl-1H-indol-5-yl group, 2,3-dimethyl-1H-indol-5-yl group, 1-methyl-1H-indol-5-yl group, 1,2-dimethyl-1H-indol-5-yl group, 1,3-dimethyl-1H-indol-5-yl group, 1,2,3-trimethyl-1H-indol-5-yl group, 1-ethyl-1H-indol-5-yl group, 1-ethyl-2-methyl-1H-indol-5-yl group, 1-ethyl-3-methyl-1H-indol-5-yl group, 1-ethyl-2,3-dimethyl-1H-indol-5-yl group, 1-propyl-1H-indol-5-yl group, 2-methyl-1-propyl-1H-indol-5-yl group, 3-methyl-1-propyl-1H-indol-5-yl group, 2,3-dimethyl-1-propyl-1H-indol-5-yl group, 1-(2-hydroxyethyl)-1H-indol-5-yl group, 1-(2-hydroxyethyl)-2-methyl-1H-indol-5-yl group, 1-(2-hydroxyethyl)-3-methyl-1H-indol-5-yl group, 2,3-dimethyl-1-(2-hydroxyethyl)-1H-indol-5-yl group, benzothiazol-6-yl group, 2-methylbenzothiazol-6-yl group, 2-methoxybenzothiazol-6-yl group, 2-aminobenzothiazol-6-yl group, 2-oxo-2,3-dihydrobenzothiazol-6-yl group, 2-oxo-3-methyl-2,3-dihydrobenzothiazol-6-yl group, 2-thioxo-2,3-dihydrobenzothiazol-6-yl group, 2-thioxo-3-methyl-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 1-propyl-1H-indazol-5-yl group, 1-(2-hydroxyethyl)-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, 1-propyl-1H-pyrrolo[2,3-b]pyridin-5-yl group, 1-(2-hydroxyethyl)-1H-pyrrolo[2,3-b]pyridin-5-yl group, isoquinolin-6-yl group, 1-oxo-1,2-dihydroisoquinolin-6-yl group, cinnolin-6-yl group, benzoxazol-5-yl group, and the like.

Further, particularly preferred examples include naphthalen-2-yl group, 6-hydroxynaphthalen-2-yl group, 6-methoxynaphthalen-2-yl group, 6-aminonaphthalen-2-yl group, 6-(N,N-dimethylamino)naphthalen-2-yl group, benzo[b]furan-5-yl group, benzo[b]thiophen-5-yl group, 1H-indol-5-yl group, 1-methyl-1H-indol-5-yl group, 1-ethyl-1H-indol-5-yl group, benzothiazol-6-yl group, 2-aminobenzothiazol-6-yl group, 2-oxo-2,3-dihydrobenzothiazol-6-yl group, quinolin-3-yl group, quinolin-6-yl group, 2-oxo-1,2-dihydroquinolin-6-yl group, benzo[d]isothiazol-5-yl group, 1H-indazol-5-yl group, 1-methyl-1H-indazol-5-yl group, 1-ethyl-1H-indazol-5-yl group, 3-hydroxy-1H-indazol-5-yl group, 3-hydroxy-1-methyl-1H-indazol-5-yl group, 1-ethyl-3-hydroxy-1H-indazol-5-yl group, imidazo[1,2-a]pyridin-6-yl group, 1H-pyrrolo[2,3-b]pyridin-5-yl group, 1-methyl-1H-pyrrolo[2,3-b]pyridin-5-yl group, 1-ethyl-1H-pyrrolo[2,3-b]pyridin-5-yl group, isoquinolin-6-yl group, 1-oxo-1,2-dihydroisoquinolin-6-yl group, cinnolin-6-yl group, benzoxazol-5-yl group, and the like.

In the formula (I), the group Y is defined to be hydrogen atom, a lower alkyl group having 1 to 4 carbon atoms, —$(CH_2)_m N(R^{18})(R^{19})$, or —$C(R^{20})_2 OC(O)A^3 R^{21}$, and among them, hydrogen atom is particularly preferred.

Examples of the lower alkyl group having 1 to 4 carbon atoms include methyl group, ethyl group, propyl group, isopropyl group, butyl group, isobutyl group, t-butyl group, and the like. Among them, methyl group, and ethyl group are particularly preferred.

Symbol m in —$(CH_2)_m N(R^{18})(R^{19})$ is defined to be an integer of 2 or 3. $R^{18}$ is the same as $R^{19}$, or binds to $R^{19}$ to represent a saturated nitrogen-containing cycloalkyl group forming a 3- to 6-membered ring together with nitrogen atom, or form morpholino group together with nitrogen atom, and $R^{19}$ is defined to be methyl group, ethyl group, or propyl group. Examples of —$(CH_2)_m N(R^{18})(R^{19})$ include 2-(N,N-dimethylamino)ethyl group, 2-(N,N-diethylamino)ethyl group, 2-(N,N-dipropylamino)ethyl group, 3-(N,N-dimethylamino)propyl group, 3-(N,N-diethylamino)propyl group, 2-(N,N-dipropylamino)propyl group, 2-pyrrolidin-1-ylethyl group, 2-piperidin-1-ylethyl group, 2-morpholin-4-ylethyl group, 3-pyrrolidin-1-ylpropyl group, 3-piperidin-1-ylpropyl group, 3-morpholin-4-ylpropyl group, and the like.

$R^{20}$ in —$C(R^{20})_2 OC(O)A^3 R^{21}$ is defined to be hydrogen atom, methyl group, ethyl group, or propyl group. $R^{21}$ is defined to be a lower alkyl group having 1 to 4 carbon atoms, a cyclic saturated alkyl group having 3 to 6 carbon atoms, or phenyl group. Examples of the lower alkyl group having 1 to 4 carbon atoms include methyl group, ethyl group, propyl group, isopropyl group, butyl group, isobutyl group, t-butyl group, and the like, and examples of the cyclic saturated alkyl group having 3 to 6 carbon atoms group include cyclopropyl group, cyclobutyl group, cyclopentyl group, and cyclohexyl group. $A^3$ is defined to be a single bond, or oxygen atom.

Examples of —C(R$^{20}$)$_2$OC(O)A$^3$R$^{21}$ include acetoxymethyl group, propionyloxymethyl group, butyryloxymethyl group, (2-methylpropionyl)oxymethyl group, (2,2-dimethylpropionyl)oxymethyl group, cyclopropionyloxymethyl group, cyclopentanoyloxymethyl group, cyclohexanoyloxymethyl group, phenylcarboxymethyl group, 1-acetoxy-1-methylethyl group, 1-methyl-1-(2-methylpropionyloxy)ethyl group, 1-cyclopentanoyloxy-1-methylethyl group, 1-cyclohexanoyloxy-1-methylethyl group, methoxycarbonyloxymethyl group, ethoxycarbonyloxymethyl group, isopropyloxycarbonyloxymethyl group, t-butyloxycarbonyloxymethyl group, cyclopropyloxycarbonyloxymethyl group, cyclopentyloxycarbonyloxymethyl group, cyclohexyloxycarbonyloxymethyl group, phenyloxycarbonyloxymethyl group, 1-methoxycarbonyloxy-1-methylethyl group, 1-ethoxycarbonyloxy-1-methylethyl group, 1-isopropyloxycarbonyloxy-1-methylethyl group, 1-t-butyloxycarbonyloxy-1-methylethyl group, 1-cyclopropyloxycarbonyloxy-1-methylethyl group, 1-cyclopentyloxycarbonyloxy-1-methylethyl group, 1-cyclohexyloxycarbonyloxy-1-methylethyl group, 1-methyl-1-phenyloxycarbonyloxyethyl group, and the like.

The compound contained in the pharmaceutical composition of the present invention may have one or more asymmetric carbons depending on types of substituents. For example, as for a compound wherein the group R$^5$ contains one or more asymmetric carbons, two kinds of optical isomers exist when the number of asymmetric carbon is 1, and when the number of asymmetric carbons is 2, four kinds of optical isomers and two kinds of diastereomers exist. Pure stereoisomers including optical isomers and diastereoisomers, any mixtures thereof, racemates and the like of the stereoisomers fall within the scope of the compound contained in the pharmaceutical composition of present invention. Further, the compound contained in the pharmaceutical composition of the present invention may exist as geometrical isomers based on a cycloalkyl ring structure, and any geometrical isomers in pure forms, and any mixtures of the geometrical isomers also fall within the scope of the compound contained in the pharmaceutical composition of present invention. Mixtures such as racemates may sometimes be preferred from a viewpoint of easiness for manufacture.

As a salt of the compound contained in the pharmaceutical composition of the present invention, a pharmaceutically acceptable salt is preferred. It is meant that, when at least one of the conditions (1) and (2) is satisfied: (1) Y is hydrogen atom; (2) the group AR contains carboxyl group or phenolic hydroxyl group; and the like, then the compound forms 1 to 3 alkali salts depending on the number of acidic groups. Examples the alkali salts include, for example, salts with inorganic bases such as sodium and ammonia and salts with organic bases such as triethylamine.

Alternatively, it is meant that, when at least one of the conditions (1) to (3) is satisfied: (1) the group Rs has properties as a base as in a compound wherein Rs contains a substituted or unsubstituted amino group and the like; (2) AR itself is a cyclic substituent having properties as a base; (3) the group AR contains a substituted or unsubstituted amino group, then the compound forms 1 to 4 acidic salts depending on the number of basic groups. Examples of the acidic salts include, for example, salts with inorganic acids such as hydrochloric acid and sulfuric acid and salts with organic acids such as acetic acid and citric acid. The salt of the compound represented by the general formula (I) contained in the pharmaceutical composition is not particularly limited so far that the salt can be formed with the compound. However, pharmaceutically acceptable salts are preferred.

Examples of the pharmaceutically acceptable salts include, for example, sodium salts, potassium salts, calcium salts, ammonium salts, hydrochlorides, hydrobromides, nitrates, sulfates, hydrogensulfates, phosphates, acetates, lactates, succinates, citrates, maleates, tartrates, fumarates, methanesulfonates, p-toluenesulfonates, camphorsulfonates, mandelates, and the like.

Preferred examples of the compound contained in the pharmaceutical composition of the present invention include the compounds described in WO03/070686 wherein Z is amino group. Examples of preferred embodiments of the compound contained in the pharmaceutical composition of the present invention include the compounds described in WO03/070686 as preferred compounds wherein Z is amino group.

As another embodiment, preferred examples of the compound contained in the pharmaceutical composition of the present invention include the compounds described in WO2005/016862 wherein any one of $C^2$, $C^3$, $C^4$, $C^5$, and $C^6$ in the aromatic ring (E) is a carbon atom substituted with amino group.

For the pharmaceutical composition of the present invention, besides the compounds represented by the general formula (I) or salts thereof, prodrugs thereof and further, hydrates thereof can also be used. More specifically, the compounds represented by the general formula (I) or salts thereof may include hydrates thereof. The compounds represented by the general formula (I) or salts thereof may include prodrugs thereof. Examples of the prodrugs include compounds or salts thereof that is oxidized, hydrolyzed, or the like in living bodies, preferably in digestive tract, liver, or blood, after oral or parenteral administration to mammals to produce a compound of the aforementioned general formula (I) or a salt thereof. For example, many means are known for making medicaments having carboxyl group, amino group, hydroxyl group or the like into prodrugs, and an appropriate means can be chosen by those skilled in the art.

Examples of the compound contained in the pharmaceutical composition of the present invention include, but not particularly limited so far that the compound is chosen from the aforementioned compounds:
3-[3-amino-4-(indan-2-yloxy)-5-(1H-indazol-5-yl)phenyl] propionic acid;
3-[3-amino-5-(1-ethyl-1H-indazol-5-yl)-4-(indan-2-yloxy) phenyl]propionic acid;
3-[3-amino-4-(4-fluoroindan-2-yloxy)-5-(1-methyl-1H-indazol-5-yl)phenyl]propionic acid;
3-[3-amino-4-(5-fluoroindan-2-yloxy)-5-(1-methyl-1H-indazol-5-yl)phenyl]propionic acid;
3-[3-amino-4-(5,6-difluoroindan-2-yloxy)-5-(1-methyl-1H-indazol-5-yl)phenyl]propionic acid;
3-[3-amino-4-(1-hydroxyindan-2-yloxy)-5-(1-methyl-1H-indazol-5-yl)phenyl]propionic acid;
3-[3-amino-4-(4-hydroxyindan-2-yloxy)-5-(1-methyl-1H-indazol-5-yl)phenyl]propionic acid;
3-[3-amino-4-(5-hydroxyindan-2-yloxy)-5-(1-methyl-1H-indazol-5-yl)phenyl]propionic acid;
3-[3-amino-4-(5,6-dihydroxyindan-2-yloxy)-5-(1-methyl-1H-indazol-5-yl)phenyl]propionic acid;
3-[3-amino-4-(4-methoxyindan-2-yloxy)-5-(1-methyl-1H-indazol-5-yl)phenyl]propionic acid;
3-[3-amino-4-(5-methoxyindan-2-yloxy)-5-(1-methyl-1H-indazol-5-yl)phenyl]propionic acid;
3-[3-amino-4-(5,6-dimethoxyindan-2-yloxy)-5-(1-methyl-1H-indazol-5-yl)phenyl]propionic acid;
3-[3-amino-4-(4-benzyloxyindan-2-yloxy)-5-(1-methyl-1H-indazol-5-yl)phenyl]propionic acid;

3-[3-amino-4-(4-benzyloxyindan-2-yloxy)-5-(1-methyl-1H-indazol-5-yl)phenyl]propionic acid;
3-[3-amino-4-(5,6-dibenzyloxyindan-2-yloxy)-5-(1-methyl-1H-indazol-5-yl)phenyl]propionic acid;
3-[3-amino-4-(4-fluoroindan-2-yloxy)-5-(H-indazol-5-yl)phenyl]propionic acid;
3-[3-amino-4-(5-fluoroindan-2-yloxy)-5-(H-indazol-5-yl)phenyl]propionic acid;
3-[3-amino-4-(5,6-difluoroindan-2-yloxy)-5-(1H-indazol-5-yl)phenyl]propionic acid;
3-[3-amino-4-(1-hydroxyindan-2-yloxy)-5-(1H-indazol-5-yl)phenyl]propionic acid;
3-[3-amino-4-(4-hydroxyindan-2-yloxy)-5-(1H-indazol-5-yl)phenyl]propionic acid;
3-[3-amino-4-(5-hydroxyindan-2-yloxy)-5-(1H-indazol-5-yl)phenyl]propionic acid;
3-[3-amino-4-(5,6-dihydroxyindan-2-yloxy)-5-(H-indazol-5-yl)phenyl]propionic acid;
3-[3-amino-5-(1H-indazol-5-yl)-4-(4-methoxyindan-2-yloxy)phenyl]propionic acid;
3-[3-amino-5-(1H-indazol-5-yl)-4-(5-methoxyindan-2-yloxy)phenyl]propionic acid;
3-[3-amino-4-(5,6-dimethoxyindan-2-yloxy)-5-(1H-indazol-5-yl)phenyl]propionic acid;
3-[3-amino-4-(4-benzyloxyindan-2-yloxy)-5-(1H-indazol-5-yl)phenyl]propionic acid;
3-[3-amino-4-(4-benzyloxyindan-2-yloxy)-5-(H-indazol-5-yl)phenyl]propionic acid;
3-[3-amino-4-(5,6-dibenzyloxyindan-2-yloxy)-5-(H-indazol-5-yl)phenyl]propionic acid;
3-[3-amino-5-(1-ethyl-1H-indazol-5-yl)-4-(4-fluoroindan-2-yloxy)phenyl]propionic acid;
3-[3-amino-5-(1-ethyl-1H-indazol-5-yl)-4-(5-fluoroindan-2-yloxy)phenyl]propionic acid;
3-[3-amino-4-(5,6-difluoroindan-2-yloxy)-5-(1-ethyl-1H-indazol-5-yl)phenyl]propionic acid;
3-[3-amino-5-(1-ethyl-1H-indazol-5-yl)-4-(1-hydroxyindan-2-yloxy)phenyl]propionic acid;
3-[3-amino-5-(1-ethyl-1H-indazol-5-yl)-4-(4-hydroxyindan-2-yloxy)phenyl]propionic acid;
3-[3-amino-5-(1-ethyl-1H-indazol-5-yl)-4-(5-hydroxyindan-2-yloxy)phenyl]propionic acid;
3-[3-amino-4-(5,6-dihydroxyindan-2-yloxy)-5-(1-ethyl-1H-indazol-5-yl)phenyl]propionic acid;
3-[3-amino-5-(1-ethyl-1H-indazol-5-yl)-4-(4-methoxyindan-2-yloxy)phenyl]propionic acid;
3-[3-amino-5-(1-ethyl-1H-indazol-5-yl)-4-(5-methoxyindan-2-yloxy)phenyl]propionic acid;
3-[3-amino-4-(5,6-dimethoxyindan-2-yloxy)-5-(1-ethyl-1H-indazol-5-yl)phenyl]propionic acid;
3-[3-amino-4-(4-benzyloxyindan-2-yloxy)-5-(1-ethyl-1H-indazol-5-yl)phenyl]propionic acid;
3-[3-amino-4-(4-benzyloxyindan-2-yloxy)-5-(1-ethyl-1H-indazol-5-yl)phenyl]propionic acid;
3-[3-amino-4-(5,6-dibenzyloxyindan-2-yloxy)-5-(1-ethyl-1H-indazol-5-yl)phenyl]propionic acid;
3-{3-amino-4-[2-(4-methylphenyl)ethyloxy]-5-(naphthalen-2-yl)phenyl}propionic acid;
3-[3-amino-4-cyclopentylmethyloxy-5-(1H-indol-5-yl)phenyl]propionic acid;
3-[3-amino-4-cyclopentylmethyloxy-5-(1-methyl-1H-indol-5-yl)phenyl]propionic acid; and 3-[3-amino-4-cyclopentylmethyloxy-5-(naphthalen-2-yl)phenyl]propionic acid.

Preferred examples of the compound contained in the pharmaceutical composition of the present invention include:
3-[3-amino-4-(indan-2-yloxy)-5-(1-methyl-1H-indazol-5-yl)phenyl]propionic acid;
3-{3-amino-4-[2-(4-methylphenyl)ethyloxy]-5-(naphthalen-2-yl)phenyl}propionic acid;
3-[3-amino-4-cyclopentylmethyloxy-5-(1H-indol-5-yl)phenyl]propionic acid;
3-[3-amino-4-cyclopentylmethyloxy-5-(1-methyl-1H-indol-5-yl)phenyl]propionic acid;
3-[3-amino-4-(indan-2-yloxy)-5-(1H-indazol-5-yl)phenyl]propionic acid;
3-[3-amino-4-cyclopentylmethyloxy-5-(naphthalen-2-yl)phenyl]propionic acid, and the like, and more preferred examples of the compound include 3-[3-amino-4-(indan-2-yloxy)-5-(1-methyl-1H-indazol-5-yl)phenyl]propionic acid.

When the compound contained in the pharmaceutical composition of the present invention is 3-[3-amino-4-(indan-2-yloxy)-5-(1-methyl-1H-indazol-5-yl)phenyl]propionic acid (this compound may sometimes be hereinafter referred to as "Compound 1 of the present invention"), a form of Compound 1 of the present invention is not particularly limited, and type A crystals or type B crystals of Compound 1 of the present invention, or a mixture thereof may be used. Compound 1 of the present invention in the form of oil may also be used.

The type A crystals of Compound 1 of the present invention will be explained. Examples of the characteristics of the type A crystals of Compound 1 of the present invention include the followings. More specifically, they have, in a powder X-ray diffraction spectrum, one or more characteristic peaks at 2θ s of at least 6.9±0.2°, 16.4±0.2°, 18.2±0.2°, 25.0±0.2° and 27.5±0.2°, preferably at 2θ s of 6.9±0.2°, 14.4±0.2°, 16.4±0.2°, 18.2±0.2°, 25.0±0.2° and 27.5±0.2°.

2θ angles in a powder X-ray diffraction spectrum may include some acceptable measurement errors due to various kinds of factors, and actually measured values fluctuate by usually about ±0.3°, typically about ±0.2°, or about ±0.1° for a more preferable measurement. Therefore, it will be understood that 2θ angles based on actually measured values for a specific sample indicated in the specification may include such an acceptable measurement error.

As another characteristic of the type A crystals of Compound 1 of the present invention, for example, they show an endothermic peak at about 182° C. in a differential scanning calorimetry (temperature elevation rate: 10° C./minute).

Although endothermic peak observed in the differential scanning calorimetry is a property characteristic to crystals of the compound of the present invention, a possibility that, besides measurement errors, melting point may occasionally change in a practical measurement due to various causes such as contamination of an acceptable amount of impurities cannot be denied. Therefore, those skilled in the art can understand degree of change of the endothermic peak temperatures referred to in the present invention practically measured in differential scanning calorimetry, and an error of, for example, about ±5° C., typically about ±3° C., or about +2° C. for preferred measurement, may be expected.

Further, other characteristics of the type A crystals of Compound 1 of the present invention include that they show marked infrared absorption bands at wave numbers of around 3361, 2938, 1712, 1204, 1011 and 746 cm$^{-1}$ in an infrared absorption spectrum.

It is noted that some measurement error is accepted also for the wave number in infrared absorption spectrum, and such error may be contained also in the present invention. Those skilled in the art readily understand degree of the error, and for example, according to the 4th edition of European Pharmacopoeia, in comparison with a reference spectrum in a confirmation test based on infrared absorption spectra, coincidence of wave number scale with a difference of +0.5% or less is accepted. Although it is not intended to be bound by the aforementioned criterion in the present invention, as an example of criterion, a measurement error of about ±0.8%, preferably about ±0.5%, particularly preferably about ±0.2%, contained in the actually measured values is acceptable for the wave number scale.

Examples of the type A crystals of Compound 1 of the present invention are crystals defined by any one or a combination of any two or more of the aforementioned various characteristics. It was confirmed that the type A crystals showing the constant properties had more preferred properties as a pharmaceutical preparation or at time of exhibiting efficacy, or during a manufacturing process and the like, as compared with ordinary uncontrolled crystals. The aforementioned type A crystals have, for example, higher solubility in an aqueous solvent compared with the type B crystals described later, which is also a preferred property.

Preferred examples of crystals used in another embodiment of the present invention also include type B crystals. The type B crystals of Compound 1 of the present invention will be explained. Examples of the characteristic features of the type B crystals of Compound 1 of the present invention include the followings. More specifically, they have, in a powder X-ray diffraction spectrum, one or more characteristic peaks at 2θ s of at least 15.9±0.2°, 17.3±0.2°, 22.2±0.2° and 22.9±0.2°, preferably at 2θ s of 14.4±0.2°, 15.9±0.2°, 17.3±0.2°, 22.2±0.2° and 22.9±0.2°.

As another characteristic feature of the type B crystals of Compound 1 of the present invention, for example, they have an endothermic peak at about 203° C. in a differential scanning calorimetry (temperature elevation rate: 10° C./minute).

Further, other characteristics of the type A crystals of Compound 1 of the present invention include that they have noticeable infrared absorption bands at wave numbers of around 2939, 1720, 1224, 1016 and 751 cm$^{-1}$ in an infrared absorption spectrum.

Examples of the type B crystals of Compound 1 of the present invention are crystals defined by any one or a combination of any two or more of the aforementioned various characteristics. It was confirmed that the type B crystals showing the constant properties had more preferred properties as a pharmaceutical preparation or at time of exhibiting efficacy, or during a manufacturing process and the like, as compared with ordinary uncontrolled crystals. These type B crystals have higher filterability and in addition improved flowability, as compared with the type A crystals, and it is expected that, for example, the time required for a filtration step and/or a dehydrating step and the like can be shortened in a large scale manufacture of the B-type crystals. The type B crystals are more preferred also for manufacture of dry preparations and solid preparations. It has been also confirmed that filtered and dehydrated type B crystals have lower moisture content compared with filtered and dehydrated type A crystals, and they are expected to shorten time and reduce thermal energy required for drying, and considered preferable especially for manufacture in a large scale. Apart from these features, it is considered that these type B crystals have substantially more favorable morphological stability as compared with the type A crystals.

As the method of producing the type A crystals of Compound 1 of the present invention, there may be mentioned a method of adding an acid to a basic solution of Compound 1 of the present invention to produce crystals of Compound 1 of the present invention, and thus obtaining the crystals.

More specifically, the basic solution of Compound 1 of the present invention as used in the present invention is not particularly limited so long as being a solution containing the compound dissolved under basic conditions, and here, the compound to be dissolved may be in any of an oily state, solid state (including various crystal types and amorphous type), and mixtures thereof. Compound 1 of the present invention can be prepared according to the method described in International Patent Publication WO03/70686.

Inorganic bases are preferred as the base used for preparing the basic solution as described above. More specifically, for example, alkali metal bases such as sodium hydroxide, potassium hydroxide, sodium carbonate, potassium carbonate, sodium methoxide and potassium t-butoxide, and the like may be mentioned. Sodium hydroxide, potassium hydroxide and the like are preferred, and sodium hydroxide may be mentioned as a particularly preferred example. These bases can be used in the form of a solution prepared by dissolving them in water, an alcohol such as methanol, ethanol or t-butanol, or the like. It is particularly preferable to prepare and use an aqueous solution containing a base at a predetermined concentration from the viewpoint that it is easy to define the amount of an acid to be added, and the like. However, in the case a concentrated basic solution is used, there is a concern that when an acid is added later, high heat due to the neutralization reaction would occur, and thus using a 0.5 to 2 N aqueous solution of base may be mentioned as a very preferable example.

The amount of base to be added may be, as for the lower limit, it is usually 0.8 equivalents or more, preferably 0.9 equivalents or more, more preferably 1.0 equivalent or more, relative to 1 equivalent of the compound. As for the upper limit, it is usually 3.0 equivalents or less relative to 1 equivalent of the compound may be mentioned, and 2.0 equivalents or less may be mentioned as a preferred example.

As the solvent to be used for dissolving the compound together with the base, polar solvents may be preferably mentioned, and specifically, water, alcohols such as methanol and ethanol, ethers such as tetrahydrofuran and dioxane, acetone and the like may be mentioned. Mixtures thereof can also be used according to necessity. Among them, water, methanol, ethanol, tetrahydrofuran and the like are preferred, and water, methanol, ethanol and the like are particularly preferred. Furthermore, it is very preferable to use a mixture of water and methanol, and the ratio of mixing of water:methanol to be obtained after preparing a solution containing a base, may be, for example, 1:20 to 10:1, while a ratio of 1:10 to 1:1 is preferred.

The above-described basic solution may be heated at a temperature lower than or equal to the boiling point of the solvent, and if impurities are present, it is preferred to remove impurities by processes such as filtration.

As the acid to be added to the solution described above, the acid may be in any of liquid state, solid state and gaseous state, as long as the acid is not incorporated into the precipitate of crystals generated upon adding the acid. However, the acid is preferably in a solution state or gaseous state, while an acid in the solution state may be mentioned as a preferred example.

Furthermore, type of the acid may be any of organic acids and inorganic acids. However, since the acid to be used should neutralize the base, it is necessary that acidity of the acid be higher than the acidity of the compounds of the present invention. Thus, mineral acids such as hydrochloric acid, sulfuric acid and phosphoric acid are preferred, and hydrochloric acid is particularly preferred. These can also be used in the form of a solution prepared by dissolving them in water or an alcohol such as methanol, ethanol or t-butanol. It is preferable to prepare and use an aqueous solution containing an acid at a predetermined concentration from the viewpoint that it is easy to define the amount of the solution to be added, and the like. However, in the case of using a concentrated acidic solution, there is a concern that high heat due to the neutralization reaction would occur, and thus using a 0.5 to 2 N aqueous solution of acid may be mentioned as a particularly preferable example.

As the amount of acid to be added, the acid may be added to the extent that crystals are sufficiently generated, and therefore the amount is not particularly limited. However, for example, usually 0.8 equivalents or more, relative to 1 equivalent of base, may be mentioned, and it is preferable to add 0.9 equivalents or more. Also, it is particularly preferable to add about 1 equivalent. Furthermore, there is no particular limitation concerning the upper limit, but for example, usually 1.5 equivalents or less, and preferably 1.2 equivalents or less relative to 1 equivalent of base may be mentioned.

Examples of the method of adding acid include (1) adding at once, (2) adding in several divided portions, (3) adding continuously over a period of time by adding dropwise, or the like, but a method of adding continuously over a period of time by a method such as adding dropwise is preferred. Upon adding an acid, it is preferable to perform stirring. The rate of addition may vary depending on the amount of the compound used, the concentration of the base in the basic solution, the type of the acid used, or the concentration of the acidic solution. However, in the case of using 0.5 to 2 N hydrochloric acid, there may be mentioned a method of adding the entire amount over 1 hour to 6 hours.

With regard to the temperature for the addition of acid, the upper limit is preferably 60° C. or lower, more preferably 50° C. or lower, still more preferably 45° C. or lower, and as for the lower limit, it is preferably 0° C. or higher, more preferably 10° C. or higher, still more preferably 25° C. or higher.

Obtaining the generated crystals may be performed usually within 24 hours, preferably within 20 hours, particularly preferably within 10 hours, after the addition of acid. It is also possible to collect crystals immediately after the addition of acid, but it is preferable to collect the crystals after a period of 1 hour or longer after the addition of acid, and particularly preferably after a period of 3 hours or longer after the addition of acid.

As the method for collecting precipitated crystals, it is possible to obtain crystals by a known method such as filtration or decantation, but filtration is usually preferred. Furthermore, after collecting crystals by filtration, the crystals can be washed with a polar solvent, for example, water, methanol, ethanol or a mixture thereof, and this process is effective as a process for removing impurities. As the method of washing, a method of rinsing the crystals on the filtration vessel with a polar solvent is preferred. It is also preferable to use a method of introducing the crystals into a polar solvent such as water, methanol, ethanol or a mixture thereof to form a suspension, stirring the suspension sufficiently, and then obtaining the crystals again by filtration. Furthermore, it is particularly preferable to perform both of the washing processes described above. The collected crystals can be dried by a generally performed drying method, such as drying under reduced pressure, drying under reduced pressure while heating, drying under normal pressure while heating, or air drying.

The final concentration of the precipitated compound after adding the acid to the basic solution may vary depending on the type of the solvent used, and in the case of a mixed solvent, it may vary also depending on the mixing ratio. However, as for the lower limit, it may be generally 1 w/v % or more, preferably 5 w/v % or more. As for the upper limit, it may be, for example, preferably 30 w/v % or less, more preferably 20 w/v % or less.

Additionally, it is thought that upon generating crystals, adding a small amount of type A crystals as seed crystals is a preferred embodiment.

As a preferred example among the preparation methods described above, the following may be mentioned. In the following three examples of the preparation method, the preferred examples of the amount of the base used, the stirring temperature before the addition of acid, the amount of the acid added, and the stirring time after the addition of acid described above can be employed.

A method of adding to a solution containing 3-[3-amino-4-(indan-2-yloxy)-5-(1-methyl-1H-indazol-5-yl)phenyl]propionic acid and 0.8 to 3.0 equivalents of sodium hydroxide or potassium hydroxide relative to the amount of said compound in water, methanol, ethanol, tetrahydrofuran or a mixed solvent thereof, 0.8 to 1.5 equivalents of an aqueous solution of hydrochloric acid, sulfuric acid or phosphoric acid relative to 1 equivalent of said base continuously over time by a method such as adding dropwise at a temperature of 10 to 50° C. with stirring; and further stirring the mixture for 1 to 24 hours to obtain crystals.

A method of adding to a solution containing the above compound and 0.9 to 2.0 equivalents of sodium hydroxide relative to 1 equivalent of said compound in water, methanol, ethanol or a mixed solvent thereof, 0.9 to 1.2 equivalents of a 0.5 to 2 N aqueous solution of hydrochloric acid relative to 1 equivalent of said base over 1 hour to 6 hours at a temperature of 25 to 45° C. with stirring; and further stirring the mixture for 3 to 24 hours to obtain crystals.

A method of adding to a solution of the above compound in a mixture of methanol and a 0.5 to 2 N aqueous solution of sodium hydroxide in an amount to give 0.9 to 2.0 equivalents of the base relative to 1 equivalent of said compound, a 0.5 to 2 N aqueous solution of hydrochloric acid in an amount corresponding to 0.9 to 1.2 equivalents relative to 1 equivalent of said base over 1 hour to 6 hours at a temperature of 25 to 45° C. with stirring; and further stirring the mixture for 3 to 24 hours to obtain crystals.

Furthermore, the basic solution of Compound 1 of the present invention may be an alkali hydrolysate of a lower alkyl ester of 3-[3-amino-4-(indan-2-yloxy)-5-(1-methyl-1H-indazol-5-yl)phenyl]propionic acid. More specifically, as another method of producing type A crystals, the following may be mentioned.

A method of subjecting a lower alkyl ester of 3-[3-amino-4-(indan-2-yloxy)-5-(1-methyl-1H-indazol-5-yl)phenyl]propionic acid to alkali hydrolysis in a solvent, and then adding an acid to said hydrolysate solution which is under basic conditions, to obtain crystals.

The "lower alkyl ester" includes a carboxylic acid ester of an alkyl group having 1 to 4 carbon atoms, and the alkyl group having 1 to 4 carbon atoms may be any of methyl group, ethyl group, n-propyl group, isopropyl group, n-butyl group, isobutyl group, sec-butyl group and t-butyl group. Among them, methyl group and ethyl group are particularly preferred examples.

A lower alkyl ester of 3-[3-amino-4-(indan-2-yloxy)-5-(1-methyl-1H-indazol-5-yl)phenyl]propionic acid can be prepared according to the method of International Patent Publication WO03/70686.

As the base used in the preparation of the alkali hydrolysate of the compound described above, the bases used for making the above-described solution basic can be used.

Examples of the amount of the base used include usually 1 equivalent or more relative to 1 equivalent of the compound. As the upper limit, usually 10 equivalents or less may be mentioned relative to 1 equivalent of the compound, and preferably 3 equivalents or less, particularly preferably 2 equivalents or less may be mentioned, for example.

As for the solvent, the reaction is usually preferably performed in an inert solvent which does not interfere with the reaction, more preferably such a polar solvent. Although reference can be made to the conditions described above, examples of the polar solvent include water, methanol, ethanol, tetrahydrofuran, dioxane and the like, and if necessary, these solvents can be used as a mixture. Among them, water, methanol, ethanol, tetrahydrofuran and the like are preferred, and water, methanol, ethanol and the like are particularly preferred. Furthermore, it is very preferable to use a mixture of water and methanol, and the mixing ratio of water:methanol of the reaction solution after adding the base may be, for example, 1:20 to 10:1, preferably 1:10 to 1:1.

As the reaction temperature of the alkali hydrolysis, an appropriate temperature may be selected, for example, from room temperature to the reflux temperature of the solvent, and particularly preferably, for example, a condition of 50 to 70° C. may be mentioned. Examples of the reaction time include usually 0.5 to 72 hours, preferably 1 to 24 hours. More specifically, as for the upper limit, it is preferably 24 hours or shorter, more preferably 20 hours or shorter, still more preferably 10 hours or shorter. As for the lower limit, it is preferably 0.5 hour or longer, more preferably 1 hour or longer, still more preferably 3 hours or longer. However, since it is possible to trace the progress of reaction by thin layer chromatography (TLC), high performance liquid chromatography (HPLC) or the like, usually the reaction may be appropriately terminated when the obtainable yield of 3-[3-amino-4-(indan-2-yloxy)-5-(1-methyl-1H-indazol-5-yl)phenyl]propionic acid reaches the maximum.

After the alkali hydrolysis reaction, the acid to be added to the solution which is under basic conditions, the conditions for generating crystals, the method of collecting the crystals, and the like are as described above.

Among the production methods described above, preferred example include the followings. For the following three examples of the production method, the above-described preferred examples of the amount of the base used for the alkali hydrolysis, the reaction temperature of the hydrolysis reaction, the reaction time of the hydrolysis reaction, the stirring temperature before the addition of acid, the amount of acid to be added, and the stirring time after the addition of acid can be employed.

A method of allowing a lower alkyl ester of 3-[3-amino-4-(indan-2-yloxy)-5-(1-methyl-1H-indazol-5-yl)phenyl]propionic acid to react in water, methanol, ethanol, tetrahydrofuran or a mixed solvent thereof in the presence of 1 to 3 equivalents of sodium hydroxide or potassium hydroxide relative to 1 equivalent of the lower alkyl ester at 50 to 70° C. for 1 to 24 hours; then adding at a temperature of 10 to 50° C. with stirring, 0.8 to 1.5 equivalents of an aqueous solution of hydrochloric acid, sulfuric acid or phosphoric acid relative to 1 equivalent of the base continuously over time by a method such as adding dropwise; and then stirring the mixture for 1 to 24 hours to obtain the crystals.

A method of allowing methyl or ethyl ester of 3-[3-amino-4-(indan-2-yloxy)-5-(1-methyl-1H-indazol-5-yl)phenyl] propionic acid to react in water, methanol, ethanol or a mixed solvent thereof in the presence of 1 to 2 equivalents of sodium hydroxide relative to 1 equivalent of the methyl or ethyl ester at 50 to 70° C. for 1 to 24 hours; then adding at a temperature of 25 to 45° C. with stirring, 0.9 to 1.2 equivalents of a 0.5 to 2 N aqueous solution of hydrochloric acid relative to the base over 1 hour to 6 hours; and then stirring the mixture for 3 to 24 hours to obtain the crystals.

A method of adding to methyl or ethyl ester of 3-[3-amino-4-(indan-2-yloxy)-5-(1-methyl-1H-indazol-5-yl)phenyl] propionic acid, 1 to 2 equivalents of a 0.5 to 2 N aqueous solution of sodium hydroxide relative to 1 equivalent of the methyl or ethyl ester and methanol, allowing the mixture to react at 50 to 70° C. for 1 to 24 hours; then adding, at a temperature of 25 to 45° C. with stirring, 0.9 to 1.2 equivalents of a 0.5 to 2 N aqueous solution of hydrochloric acid relative to 1 equivalent of the base, over 1 hour to 6 hours; and then stirring the mixture for 3 to 24 hours to obtain the crystals.

As the method of producing type B crystals of the Compound of the present invention, there may be mentioned a method of crystallizing Compound 1 of the present invention from a solution dissolving the compound in any one or two or more kinds of solvents selected from the group consisting of acetone, dichloromethane, methanol, ethyl acetate, a methanol/acetic acid mixture, and acetonitrile.

Compound 1 of the present invention can be prepared according to the method described in International Patent Publication WO03/70686 or the like, as described above.

Examples of the solvent to be used for the above include acetone, dichloromethane, methanol, ethyl acetate, acetonitrile, tetrahydrofuran, diisopropyl ether, nitrobenzene, 2,2,2-trifluoroethanol, N,N-dimethylformamide, N,N-dimethylacetamide and the like, and these solvents can also be used as a mixture. Furthermore, tetrahydrofuran/water, N,N-dimethylformamide/water, N,N-dimethylacetamide/water, tetrahydrofuran/methanol, diisopropyl ether/acetic acid, methanol/acetic acid, and the like can be mentioned. Among them, acetone, dichloromethane, methanol, ethyl acetate, acetonitrile, methanol/acetic acid and the like are preferred, and acetone, dichloromethane and the like are particularly preferred.

Upon dissolving the compound in a solvent, it is preferable to heat the solvent to a temperature lower than the boiling point of the solvent, from the viewpoint of the yield of the resulting crystals, and the like, and if impurities are present, the impurities may be removed by a process such as filtration.

The volume of the solvent to be added may vary depending on the type of the solvent used, and in the case of a mixed solvent, on the mixing ratio. However, it is preferable to use the solvent in such a volume that the compound should dissolve at a temperature below the boiling point of the solvent used, and it is particularly preferable to use in such a volume that the compound should dissolve at the saturated concentration at a temperature around the boiling point of the solvent, from a viewpoint of the yield of the resulting crystals. Specifically, for example, in the case of using acetone as the solvent, 15 to 25 ml based on 1 g of the compound is preferred, and about 15 ml may be mentioned as a more preferred example. In the case of using dichloromethane, for example, it is preferable to use an amount of 30 to 50 ml based on 1 g of the compound, and about 30 ml may be mentioned as more preferred example.

As the method of cooling the solution of compound prepared with heating, there may be mentioned methods such as rapid cooling, gradual cooling, leaving the solution to cool, and the like. However, a method of gradually cooling or a method of leaving the solution to cool is preferred.

The degree of cooling may vary depending on the volume of the solvent used, the type of the solvent used, and in the case of a mixed solvent, on the mixing ratio, and may vary depending on the temperature during the process of dissolving the compound. However, it is preferable to cool the solution below a temperature at which the saturated concentration of the compound is attained.

The cooling step may be performed while stirring, or may be performed while standing still. However, it is preferable to perform cooling while stirring from the viewpoint of accelerating precipitation of crystals and shortening the operation time.

Additionally, upon generating crystals by the method described above, adding a small amount of type B crystals as seed crystals is also a preferred embodiment.

Collection of precipitated crystals can be generally performed by filtration. Further, after collecting the crystals by filtration, the crystals can be washed with a solvent used in dissolving the compound or a solvent which does not significantly dissolve the crystals, or a mixture thereof. This step is effective for removing impurities.

The collected crystals can be dried by a generally performed drying method, such as drying under reduced pressure, drying under reduced pressure while heating, drying under normal pressure while heating, or air drying.

A preferred example of the above production method includes the following example.

A method of adding 15 to 25 ml of acetone or 30 to 50 ml of dichloromethane to 1 g of Compound 1 of the present invention, heating the mixture to a temperature near the boiling point of the solvent to dissolve the compound, filtering impurities as required, subsequently stirring the mixture at room temperature for several hours to several days, and then obtaining the generated crystals.

As another production method of the type B crystals of Compound 1 of the present invention, there may be mentioned a method of adding type B crystals of Compound 1 of the present invention as seed crystals during the process of adding an acid to a basic solution of Compound 1 of the present invention but immediately before Compound 1 of the invention starts to crystallize, thereby allowing Compound 1 of the present invention to crystallize as the type B crystal, and obtaining the crystals.

Compound 1 of the present invention used in the present invention, its form, and the method of obtaining the compound are the same as those described in the description in the section "Method for producing type A crystals of Compound 1 of the present invention." Furthermore, the same methods as described in the above can be used for preparing a basic solution of Compound 1 of the present invention. Also, it is the same as described above that the basic solution may be an alkali hydrolysate of a lower alkyl ester of 3-[3-amino-4-(indan-2-yloxy)-5-(1-methyl-1H-indazol-5-yl)phenyl]propionic acid.

Moreover, the explanations described in the above may equally apply to the type, addition amount and the like of the base used for preparing the basic solution; the type, addition amount and the like of the solvent used for dissolving the compound together with the base, and the type, addition amount, the method of addition, rate of addition, temperature during addition of the acid to be added and the like. As for the method for adding seed crystals of the type B crystals, it is preferred that no crystal is present in the mixture when the seed crystals are added, and it is preferred that the added seed crystals are not dissolved in the solution. In the case of adding an acid to a solution of the compound prepared by adding a base in an equivalent amount or more with respect to the compound, it is preferable to add the seed crystals of the type B crystals when the excessive base is neutralized by the added acid, from the viewpoint of avoiding dissolution of the seed crystals. Further, as for the above of addition of the acid, it is also a preferable method to confirm the neutralization of the excessive base by using an instrument such as a pH meter. More specifically, preferred examples of the method include, for example, when the compound has been dissolved by using 1.5 equivalents of the base relative to the compound, a method of introducing the seed crystals after the pH of the solution shows weak basicity, e.g., about pH 7 to 9, by the addition of an acid in an amount equivalent to 0.5 equivalents. It is preferable to add the seed crystals before crystals are generated by the addition of acid. When 2 N hydrochloric acid is added over 1 hour to 6 hours, it is highly probable that the crystallization takes place when the pH of the solution shows weak acidity due to addition of 0.1 to 0.2 equivalents of an acid after the excessive base is neutralized. Therefore, it is preferable to add the seed crystals of the type B crystals before such a state as described above is observed.

The amount of the type B crystals to be added is not particularly limited so long as the added crystals do not dissolve. However, the amount may be, for example, usually 0.01% or more, preferably 0.0.5% or more, particularly preferably about 0.1%, based on the dissolved compound. Although the upper limit is not particularly limited, the amount is, for example, usually 2% or less, preferably 1.5% or less, more preferably 1.0% or less, particularly preferably 0.3% or less, based on the compound. For the method of collecting the precipitated crystals, the method of drying the collected crystals, the final concentration of the compound after the addition of acid, and the like, the same conditions as those described in the section "Method for producing type A crystals of Compound 1 of the present invention" described above can be used.

Preferred examples of the above-described production method include the followings. For the following three examples of the production method, the preferred examples described above for the amount of base used, the stirring temperature before the addition of acid, the amount of acid to be added, the amount of the type B seed crystals to be added, and the stirring time after the addition of acid can be employed.

A method of adding, at a temperature of 10 to 50° C. with stirring, to a solution of Compound 1 of the present invention in water, methanol, ethanol, tetrahydrofuran or a mixed solvent thereof containing 0.8 to 3.0 equivalents of sodium hydroxide or potassium hydroxide relative to 1 equivalent of said compound, an aqueous solution of 0.8 to 1.5 equivalents of hydrochloric acid, sulfuric acid or phosphoric acid relative to 1 equivalent of the base continuously over time by a method such as adding dropwise, when the pH of the system shows weak basicity of pH 7 to 9 in the middle of the addition of the acid, adding thereto the type B seed crystals in an amount of 0.01 to 2% relative to said compound, and then stirring the mixture for 1 to 24 hours to obtain the crystals.

A method of adding, at a temperature of 25 to 45° C. with stirring, to a solution of Compound 1 of the present invention in water, methanol, ethanol or a mixed solvent thereof containing 0.9 to 2.0 equivalents of sodium hydroxide relative to 1 equivalent of said compound, 0.9 to 1.2 equivalents of a 0.5 to 2 N aqueous solution of hydrochloric acid relative to 1 equivalent of the base over 1 hour to 6 hours; when the pH of the system shows weak basicity of pH 7 to 9 in the middle of the addition of the acid, adding thereto the type B seed crystals in an amount of 0.05 to 1.5% relative to said compound, and then stirring the mixture for 1 to 5 hours to obtain the crystals.

A method of adding, at a temperature of 25 to 45° C. with stirring, to a solution of Compound 1 of the present invention in a mixture of 0.9 to 2.0 equivalents of a 0.5 to 2 N aqueous solution of sodium hydroxide relative to 1 equivalent of said compound and methanol, 0.9 to 1.2 equivalents of a 0.5 to 2 N aqueous solution of hydrochloric acid relative to 1 equivalent of the base over 1 hour to 6 hours, when the pH of the system shows weak basicity of pH 7 to 9 in the middle of the addition of the acid, adding thereto the type B seed crystals in an amount of 0.1% relative to the compound, and then stirring the mixture for 1 to 5 hours to obtain the crystals.

Preferred examples of the production method also include the following embodiments. For the following three examples of the production method, the above-described preferred examples of the amount of the base used in the alkali hydrolysis, the reaction temperature of the hydrolysis reaction, the reaction time of the hydrolysis reaction, the stirring temperature before the addition of acid, the amount of acid to be added, the amount of type B seed crystals to be added, and the stirring time after the addition of acid can be employed.

A method of allowing a lower alkyl ester of 3-[3-amino-4-(indan-2-yloxy)-5-(1-methyl-1H-indazol-5-yl)phenyl]propionic acid to react in water, methanol, ethanol, tetrahydrofuran or a mixed solvent thereof in the presence of 1 to 3 equivalents of sodium hydroxide or potassium hydroxide relative to 1 equivalent of the lower alkyl ester at 50 to 70° C. for 1 to 24 hours, subsequently adding, at a temperature of 10 to 50° C. with stirring, 0.8 to 1.5 equivalents of an aqueous solution of hydrochloric acid, sulfuric acid or phosphoric acid relative to 1 equivalent of the base continuously over time by a method of adding dropwise or the like, when the pH of the system shows weak basicity of pH 7 to 9 in the middle of the addition of the acid, adding thereto the type B seed crystals in an amount of 0.01 to 2% relative to the compound; and then stirring the mixture for 1 to 24 hours to obtain the crystals.

A method of allowing methyl or ethyl ester of 3-[3-amino-4-(indan-2-yloxy)-5-(1-methyl-1H-indazol-5-yl)phenyl] propionic acid to react in water, methanol, ethanol or a mixed solvent thereof in the presence of 1 to 2 equivalents of sodium hydroxide relative to 1 equivalent of the methyl or ethyl ester at 50 to 70° C. for 1 to 24 hours, subsequently adding, at a temperature of 25 to 45° C. with stirring, 0.9 to 1.2 equivalents of a 0.5 to 2 N aqueous solution of hydrochloric acid relative to the base over 1 hour to 6 hours, when the pH of the system shows weak basicity of pH 7 to 9 in the middle of the addition of the acid, adding thereto the type B seed crystals in an amount of 0.05 to 1.5% relative to the compound, and then stirring the mixture for 3 to 24 hours to obtain the crystals.

A method of adding to methyl or ethyl ester of 3-[3-amino-4-(indan-2-yloxy)-5-(1-methyl-1H-indazol-5-yl)phenyl] propionic acid, 1 to 2 equivalents of a 0.5 to 2 N aqueous solution of sodium hydroxide relative to 1 equivalent of the methyl or ethyl ester and methanol, allowing a reaction at 50 to 70° C. for 1 to 24 hours, subsequently adding, at a temperature of 25 to 45° C. with stirring, 0.9 to 1.2 equivalents of a 0.5 to 2 N aqueous solution of hydrochloric acid relative to 1 equivalent of the base over 1 hour to 6 hours, when the pH of the solution shows weak basicity of pH 7 to 9 in the middle of the addition of the acid, adding thereto the type B seed crystals in an amount of 0.1% relative to the compound, and then stirring the mixture for 3 to 24 hours to obtain the crystals.

The compound contained in the pharmaceutical composition of the present invention can be prepared according to the method described in WO03/070686 or WO05/016862.

Examples of the pharmaceutical composition provided by the present invention include a pharmaceutical composition comprising a compound represented by the general formula (I) or a salt thereof as an active ingredient, and a pharmaceutically acceptable carrier, wherein the composition does not substantially contain, as the pharmaceutically acceptable carrier, any reducing sugar and/or carrier containing a reducing sugar as an ingredient, or when the composition contains a reducing sugar and/or a carrier containing a reducing sugar as an ingredient as the pharmaceutically acceptable carrier, contact of the reducing sugar and the compound represented by the general formula (I) or a salt thereof is eliminated. It is preferred that the pharmaceutical composition of the present invention does not substantially contain any reducing sugar and/or carrier containing a reducing sugar as an ingredient. Another case, it is preferred that the composition contains a reducing sugar, but contact of the compound represented by the general formula (I) or a salt thereof and the reducing sugar and/or a carrier containing a reducing sugar as an ingredient is eliminated in the pharmaceutical composition.

The pharmaceutical composition of the present invention which does not substantially contain any reducing sugar and/or carrier containing a reducing sugar as an ingredient is not particularly limited, so far that the pharmaceutical composition as a whole does not substantially contain any reducing sugar. Examples of the reducing sugar content acceptable for the pharmaceutical composition of the present invention include 5 weight % or less in terms of glucose, 3 weight % or less is preferred, 1 weight % or less is more preferred, 0.5 weight % or less is still more preferred, and 0.3 weight % or less is particularly preferred. In another embodiment, it is preferred that absolutely no reducing sugar is contained. The expression "not substantially contain any reducing sugar and/or carrier containing a reducing sugar as an ingredient" should be understood by those skilled in the art to mean that reducing sugar content in the pharmaceutical composition is within the aforementioned amount. The method for measuring reducing sugar content in the pharmaceutical composition of the present invention is not particularly limited. Examples include the Bertrand method, Somogyi method, modified Somogyi method, Somogyi-Nelson method, and Lane-Eynon method, and the Somogyi-Nelson method described in Analysis Method defined by National Tax Administration Agency, 3-9 A (National Tax Administration Agency Instruction No. 1) (see Experimental Examples 6 and 7 mentioned later) is particularly preferred.

Although form of the pharmaceutical composition of the present invention is not particularly limited, so far that the form is those usually used for medicaments, the form is preferably a dry form.

Examples of moisture content in the pharmaceutical composition of a dry form include 30 weight % or less based on the total weight of the pharmaceutical composition, 20 weight % or less is preferred, 10 weight % or less is more preferred, 7 weight % or less is still more preferred, 5 weight % or less is particularly preferred, 3 weight % or less is extremely preferred, and 2 weight % or less is most preferred. Although method for measuring moisture content in the pharmaceutical composition of the present invention is not particularly limited, examples include, for example, a method of performing measurement with a moisture meter provided with dark radiator infrared metal tube-shaped heater elements (moisture meter produced by Sartorius (Model MA35)), and the moisture measurement method described in Japanese Pharmacopoeia Fifteenth Edition, General Test Procedures (Karl Fischer method), and the Karl Fischer method is preferred.

As the pharmaceutically acceptable carrier used in the present invention, examples of carriers of which use is pharmaceutically approved include ingredients approved as pharmaceutical additives. Although type thereof is not particularly limited so fat that the carriers are those usually used for manufacture of medicaments, examples include, for example, carriers such as excipients, binders, disintegrants, lubricants, and the like. Specific examples include cellulose derivatives, starches, starch derivatives, synthetic polymer compounds, sugars, polyhydric alcohols, fatty acid derivatives, and inorganic substances.

Examples of the cellulose derivatives include crystalline cellulose, methylcellulose, croscarmellose sodium, hydroxypropylcellulose, low substituted hydroxypropylcellulose, hydroxypropylmethylcellulose, carmellose, carmellose sodium, ethylcellulose, carboxymethylethylcellulose, hydroxyethylcellulose, hydroxypropylmethylcellulose phthalate, hydroxypropylmethylcellulose acetate succinate, and cellulose acetate phthalate, crystalline cellulose, methylcellulose, croscarmellose sodium, hydroxypropylcellulose, low substituted hydroxypropylcellulose, hydroxypropylmethylcellulose, carmellose, and carmellose sodium are preferred, and crystalline cellulose, croscarmellose sodium, hydroxypropylcellulose, low substituted hydroxypropylcellulose, hydroxypropylmethylcellulose, carmellose, and carmellose sodium are more preferred.

Examples of the starches include corn starch, partially pregelatinized starch, pregelatinized starch, wheat starch, rice starch, and potate starch, and corn starch is preferred.

Examples of the starch derivatives include sodium carboxymethyl starch, hydroxypropyl starch, dextrin, and pullulan, and sodium carboxymethyl starch is preferred.

Examples of the synthetic polymer compounds include crospovidone, povidone, aminoalkyl methacrylate copolymer E, aminoalkyl methacrylate copolymer RS, methacrylic acid copolymer L, methacrylic acid copolymer S, methacrylic acid copolymer LD, carboxyvinyl polymer, and polyvinyl acetal diethylaminoacetate, and crospovidone and povidone are preferred.

Examples of the sugars include reducing sugars and non-reducing sugars. The reducing sugar is not particularly limited so far that the reducing sugar is any of those described below. Examples include fructose, xylose, lactose, glucose, maltose and maltitol. The non-reducing sugar is not particularly limited so far that the sugar is other than the reducing sugar. Examples include mannitol, sucrose, erythritol, trehalose, glycerin, arabitol, xylitol, ribitol, sorbitol, and inositol, and mannitol, sucrose, erythritol, and trehalose are preferred.

Examples of the polyhydric alcohols include polyvinyl alcohol, stearyl alcohol, cetanol, propylene glycol, and polyethylene glycol, and polyvinyl alcohol is preferred.

Examples of fatty acid derivatives include aluminum stearate, calcium stearate, and magnesium stearate, and magnesium stearate is preferred.

Examples of the inorganic substances include anhydrous calcium hydrogenphosphate, kaolin, hydrated silicon dioxide, light anhydrous silicic acid, synthetic aluminum silicate, synthetic hydrotalcite, dried aluminum hydroxide gel, precipitated calcium carbonate, bentonite, and magnesium aluminometasilicate, and anhydrous calcium hydrogenphosphate is preferred.

Preferred examples of the pharmaceutically acceptable carrier include crystalline cellulose, mannitol, methylcellulose, croscarmellose sodium, corn starch, anhydrous calcium hydrogenphosphate, hydroxypropylcellulose, crospovidone, sucrose, povidone, sodium carboxymethyl starch, low substituted hydroxypropylcellulose, partially pregelatinized starch, hydroxypropylmethylcellulose, erythritol, carmellose, polyvinyl alcohol, trehalose, carmellose calcium, magnesium stearate, and carmellose sodium, more preferred examples include crystalline cellulose, mannitol, croscarmellose sodium, corn starch, anhydrous calcium hydrogenphosphate, hydroxypropylcellulose, crospovidone, sucrose, povidone, sodium carboxymethyl starch, low substituted hydroxypropylcellulose, partially pregelatinized starch, hydroxypropylmethylcellulose, erythritol, carmellose, polyvinyl alcohol, trehalose, carmellose calcium, magnesium stearate, and carmellose sodium, still more preferred examples include crystalline cellulose, mannitol, croscarmellose sodium, corn starch, anhydrous calcium hydrogenphosphate, sucrose, povidone, sodium carboxymethyl starch, low substituted hydroxypropylcellulose, partially pregelatinized starch, hydroxypropylmethylcellulose, erythritol, polyvinyl alcohol, magnesium stearate, and carmellose calcium, and particularly preferred examples include crystalline cellulose, mannitol, croscarmellose sodium, corn starch, anhydrous calcium hydrogenphosphate, sucrose, sodium carboxymethyl starch, low substituted hydroxypropylcellulose, partially pregelatinized starch, hydroxypropylmethylcellulose, erythritol, polyvinyl alcohol, and carmellose calcium.

The pharmaceutical composition of the present invention may contain one or more kinds of pharmaceutically acceptable carriers. However, it may be preferable to exclude a pharmaceutical composition comprising only methylcellulose as the pharmaceutically acceptable carrier, and a pharmaceutical composition comprising only carboxymethylcellulose as the pharmaceutically acceptable carrier. It may also be preferable to exclude a pharmaceutical composition comprising only methylcellulose as the pharmaceutically acceptable carrier, a pharmaceutical composition comprising only methylcellulose and water as the pharmaceutically acceptable carrier, a pharmaceutical composition comprising only carboxymethylcellulose as the pharmaceutically acceptable carrier, and a pharmaceutical composition comprising only carboxymethylcellulose and water as the pharmaceutically acceptable carrier.

Further, it may be preferable to exclude polyoxyethylene hydrogenated castor oil 60, TWEEN 80, hydroxypropylmethylcellulose phthalate, and hydroxypropylmethylcellulose acetate succinate as the pharmaceutically acceptable carrier used for the pharmaceutical composition of the present invention.

Examples of the reducing sugar include monosaccharides and oligosaccharides in which the aldehyde group or keto group in the saccharide molecule exists in a free form or hemiacetal form, and type thereof is not particularly limited, so long that the saccharide has reducing property and reduces the Fehling's reagent solution, ammoniacal silver nitrate solution and the like.

Reducing power of the reducing sugar can be determined by measuring oxidation reduction potential. For example, by measuring electric potential of an aqueous solution of a reducing sugar at a certain constant concentration such as 0.1 mol/L using an oxidation reduction potential meter with an oxidation reduction electrode (for example, measurement with a pH meter produced by TOA DKK (HM-30G) provided with combined electrodes produced by TOA DKK (PST-5721)), and adding the electric potential of the reference electrode to the resulting potential, the oxidation reduction potential of the reducing sugar can be obtained. To ensure accuracy, it is preferable to obtain electric potential of water by measuring electric potential of water used for dissolving the reducing sugar with an oxidation reduction potential meter having oxidation reduction electrodes, and adding the electric potential of the reference electrode to the resulting potential, and to subtract the resulting value from the oxidation reduction potential of the aqueous solution of the reducing sugar to obtain difference of the oxidation reduction potentials. When the pharmaceutical composition of the present invention does not contain any reducing sugar, examples of the reducing sugar made to be not contained in the pharmaceutical composition of the present invention is a reducing sugar having the difference of 50 mV or lower between the oxidation reduction potentials of aqueous solution of the reducing sugar and water used for dissolution, as determined by measuring oxidation reduction potential of, for example, a 0.1 moL/L aqueous solution of the reducing sugar by such a method as mentioned above. It is preferable that a reducing sugar having the difference of the oxidation reduction potentials of 60 mV or lower, more preferably 70 mV or lower, is not allowed to be contained. When the pharmaceutical composition comprising a reducing sugar is prepared, it is sufficient that contact of the compound or salt thereof as an active ingredient and the reducing sugar should be eliminated, and in such a case, type of the reducing sugar is not particularly limited.

Specific examples of the reducing sugar include, for example, fructose, xylose, lactose, glucose, maltose, maltitol, and the like. As the pharmaceutical composition not containing reducing sugar, for example, a pharmaceutical composition not containing a reducing sugar selected from the group consisting of fructose, xylose, lactose, glucose, maltose, and maltitol is preferred. The reducing sugar contained in the carrier containing a reducing sugar as an ingredient (for example, pharmaceutical additives provided as a mixture of two or more kinds of ingredients, and the like) is the same as the reducing sugar explained above.

In the pharmaceutical composition of the present invention, it is preferred that the reducing sugar and the compound represented by the general formula (I) or a salt thereof should not coexist in the pharmaceutical composition, and when they coexist, it is preferred that they should be made coexist so that the reducing sugar and the compound represented by the general formula (I) or a salt thereof should not directly contact with each other. Examples of the method of allowing the compound represented by the general formula (I) or a salt thereof not directly contact with the reducing sugar in the pharmaceutical composition include the methods mentioned below.

Although the pharmaceutically acceptable carrier used in the pharmaceutical composition of the present invention not containing a reducing sugar is not particularly limited so far that the carrier is a pharmaceutically acceptable carrier other than a reducing sugar and/or a carrier containing a reducing sugar as an ingredient, it is preferable not to use both of the reducing sugar and/or the carrier containing a reducing sugar as an ingredient as the pharmaceutically acceptable carrier, and the pharmaceutically acceptable carrier is preferably a dry carrier. Examples of the dry carrier include carriers other than liquid carrier, for example, solid carriers, specifically powdery carriers, and the like.

Examples of the pharmaceutically acceptable carrier used in the pharmaceutical composition of the present invention, which does not contain a reducing sugar, include for example, cellulose derivatives, starches, starch derivatives, synthetic polymer compounds, non-reducing sugars, polyhydric alcohols, fatty acid derivatives, and inorganic substances. Preferred carriers are the same as the aforementioned preferred examples of the pharmaceutically acceptable carrier.

Examples of the pharmaceutically acceptable carrier used in the pharmaceutical composition of the present invention, which contains a reducing sugar, include for example, carriers of which use is pharmaceutically approved, for example, ingredients approved as pharmaceutical additives. Although type thereof is not particularly limited so far that the carrier is those usually used for manufacture of medicaments, examples include cellulose derivatives, starches, starch derivatives, synthetic polymer compounds, sugars, polyhydric alcohols, fatty acid derivatives, and inorganic substances. Preferred carriers are the same as the aforementioned preferred examples of the pharmaceutically acceptable carrier.

As described above, a compound represented by the general formula (I) or a salt thereof can be mixed with a pharmaceutically acceptable carrier such as excipient, binder, disintegrants and lubricant depending on the purpose to prepare a pharmaceutical composition. Although the pharmaceutically acceptable carrier is not particularly limited so far that the carrier is selected from those usually used as excipient, binder, disintegrants, lubricant, or the like, a pharmaceutically acceptable carrier which does not interact with a compound represented by the general formula (I) or a salt thereof over time is preferred. Examples of the interaction caused over period of time include production of decomposition products, coloring, and the like.

It is preferred that the pharmaceutically acceptable carrier and the compound represented by the general formula (I) or a salt thereof should not react to generate decomposition products, when they are made into a pharmaceutical composition. As for generation of decomposition products, for example, total amount of decomposition products observed after equal weights of the pharmaceutically acceptable carrier and the compound represented by the general formula (I) or a salt thereof are stored at 60° C. for 2 weeks is preferably 0.20% or less, still more preferably 0.15% or less. Although method for measuring the decomposition products is not particularly limited so far that the method achieves measurement of the decomposition products, an example includes liquid chromatography (HPLC) and the like.

Examples of stable pharmaceutically acceptable carrier which does not generate decomposition products even when it is mixed with the compound represented by the general formula (I) or a salt thereof include, for example, crystalline cellulose, mannitol, methylcellulose, croscarmellose sodium, corn starch, anhydrous calcium hydrogenphosphate, hydroxypropylcellulose, crospovidone, sucrose, povidone, sodium carboxymethyl starch, low substituted hydroxypropylcellulose, partially pregelatinized starch, hydroxypropylmethylcellulose, erythritol, carmellose, polyvinyl alcohol, trehalose, carmellose calcium, magnesium stearate, and carmellose sodium, and still more preferred examples of the pharmaceutically acceptable carrier include crystalline cellulose, mannitol, croscarmellose sodium, corn starch, anhydrous calcium hydrogenphosphate, sucrose, sodium carboxymethyl starch, low substituted hydroxypropylcellulose, partially pregelatinized starch, hydroxypropylmethylcellulose, erythritol, polyvinyl alcohol, magnesium stearate, and carmellose calcium. One or more kinds of preferred stable pharmaceutically acceptable carriers which do not generate decomposition products with the compound represented by the general formula (I) or a salt thereof can be coexist with at least the compound represented by the general formula (I) or a salt thereof.

In the pharmaceutical composition of the present invention, content of the compound represented by the general formula (I) or a salt thereof may be an appropriate content depending on type or way of use of the pharmaceutically acceptable carrier to be used. The content of the compound represented by the general formula (I) or a salt thereof in the pharmaceutical composition is, as for the upper limit, for example, 1000 mg or less, preferably 750 mg or less, more preferably 500 mg or less, still more preferably 200 mg or less, and as for the lower limit, for example, 1 mg or more, preferably 5 mg or more, more preferably 10 mg or more, still more preferably 20 mg or more.

A property of free from coloring over period of time of a pharmaceutical composition is preferred from a viewpoint that, for example, commercial value of the pharmaceutical composition is not decreased. Coloring of a pharmaceutical composition can be evaluated by, for example, measuring color difference ($\Delta E$) of a pharmaceutical composition comprising a compound represented by the general formula (I) or a salt thereof observed when the composition is stored at 60° C. for 2 weeks. The color difference can be obtained according to the following equations 1 to 4 from, for example, differences of values of L (lightness) and a, b (hue, saturation) of samples before and after storage test under the aforementioned storage condition measured by using a color difference meter (CLR-7100F, Shimadzu). As for degree of coloring, $\Delta E$ as the upper limit is preferably 3.0 or less, more preferably 2.5 or less, still more preferably 2.0 or less, particularly preferably 1.5 or less, most preferably 1.0 or less. As for the lower limit, a value is not particularly limited so long as being 0 or larger.

$$\Delta E = \{(\Delta L)^2 + (\Delta a)^2 + (\Delta b)^2\}^{1/2}$$

$\Delta L$ = (Value of L before storage) − (Value of L after storage)

$\Delta a$ = (Value of a before storage) − (Value of a after storage)

$\Delta b$ = (Value of b before storage) − (Value of b after storage)

By mixing a pharmaceutically acceptable carrier and a compound represented by the general formula (I) or a salt thereof in a state of solution, and then by observing presence or absence of coloring, it can be determined whether the pharmaceutically acceptable carrier and the compound represented by the general formula (I) or a salt thereof react with each other. For this purpose, a solution or suspension of the pharmaceutically acceptable carrier can be added to a solution of the compound represented by the general formula (I) or a salt thereof, and then the mixture can be put into a container and warmed in a sealed state, and presence or absence of coloring can be macroscopically observed to perform the evaluation. Although the warming temperature used in this case is not particularly limited so far that the solution does not boil, an example of a temperature includes around 60° C., for example. Although storage period is not particularly limited, the period is preferably about 6 days.

Although the solvent for dissolving the compound represented by the general formula (I) or a salt thereof is not particularly limited so far that the compound can be dissolved in the solvent, methanol, ethanol, or water is preferred. Although the solvent for dissolving or suspending the pharmaceutically acceptable carrier is not also particularly limited so far that the solvent dissolve or suspend the pharmaceutically acceptable carrier, a solvent is preferred which is used for dissolving the compound represented by the general formula (I) or a salt thereof or which is free from separation to give a uniform mixture when added to a solution of said compound or a salt thereof. For example, examples include methanol, ethanol, water and the like.

Examples of stable pharmaceutically acceptable carrier which does not generate coloring even when mixed with the compound represented by the general formula (I) or a salt thereof include, for example, crystalline cellulose, mannitol, methylcellulose, croscarmellose sodium, corn starch, anhydrous calcium hydrogenphosphate, hydroxypropylcellulose, crospovidone, sucrose, povidone, sodium carboxymethyl starch, low substituted hydroxypropylcellulose, partially pregelatinized starch, hydroxypropylmethylcellulose, erythritol, carmellose, polyvinyl alcohol, trehalose, carmellose calcium, magnesium stearate, and carmellose sodium, and examples of still more preferred pharmaceutically acceptable carrier include crystalline cellulose, mannitol, methylcellulose, croscarmellose sodium, corn starch, anhydrous calcium hydrogenphosphate, hydroxypropylcellulose, crospovidone, sucrose, povidone, sodium carboxymethyl starch, low substituted hydroxypropylcellulose, partially pregelatinized starch, erythritol, polyvinyl alcohol, trehalose, magnesium stearate, and carmellose calcium.

One or more kinds of preferred stable pharmaceutically acceptable carriers which do not cause coloring with the compound represented by the general formula (I) or a salt thereof can be allowed to coexist with at least the compound or a salt thereof.

As for a process of formulation of the pharmaceutical composition of the present invention, it is preferable to prepare preparations in a dosage form of a unit dose containing a certain constant amount of a compound represented by general formula (I) or a salt to establish consistency of administration. Examples of the dosage form of a unit dose include tablets, powders, granules, syrups, suspensions, capsules, film-coated tablets, sugar-coated tablets, injections and the like, which can be prepared to obtain the pharmaceutical composition of the present invention in a conventional manner, and arbitrary preparations for oral administration in a dry state such as tablets, powders, granules, capsules, film-coated tablets, and sugar-coated tablets are preferred. The pharmaceutical composition of the present invention is preferably a preparation in a dry form.

Solid preparations include jelly-like preparations and semi-solid preparations.

As for specific method for manufacturing pharmaceutical preparations, for example, a compound represented by the general formula (I) or a salt thereof and a pharmaceutically acceptable carrier can be mixed, and then the resulting mixture can be molded into plates with a dry granulator (roller compactor, Freund Corporation), and the plates can be granulated by passing them through an appropriate mesh to obtain granules or fine granules. Alternatively, a compound represented by the general formula (I) or a salt thereof and a pharmaceutically acceptable carrier can be mixed, and then water or a solution of a polymer or the like can be added to the mixture, and further the mixture can be granulated with a agitation granulator (vertical granulator, Powlex), and the produced granules can be dried with a fluidized bed granulator (Flow Coater, Freund Corporation) to obtain granules or fine granules.

Capsules can be obtained by filling granules obtained by dry granulation or wet granulation into hard capsules such as gelatin capsules and hydroxypropyl-methylcellulose capsules with, for example, a capsule filling machine (LZ64, SANASI). However, material and form of capsule are not limited to those mentioned above. Tablets can be obtained by compressing the resulting granules with a tableting machine (C/P Correct 12HUK, Kikusui Seisakusho) or the like. The tablets obtained as described above may be made into film-coated tablets by providing film coating with an appropriate coating material or the like, or made into sugar-coated tablets by sugar coating.

Preferred examples of the method for film coating include, for example, a method of spraying a solution dissolving a coating agent such as those exemplified in Development of Drugs, Vol. 12, Materials for manufacturing pharmaceutical preparations, Chapter 2, 2.1.5 Coated products, Hirokawa Shoten, on tablets containing a compound represented by the general formula (I) or a salt thereof with a spray or the like, and drying the coating. As an apparatus for performing this method, a film coating machine comprising spray gun, pan, blower and the like is preferred, and for example, an example includes Doria Coater (Powlex) and the like.

According to physicochemical properties and purpose of use of the coating material used for this film coating, other substances may be added. Pharmaceutically acceptable substances such as plasticizers, dispersing agents and colorants can be appropriately chosen and used for the purpose of film coating in combination with the aforementioned coating material. An amount for applying the film coating is desirably in the range of 1 to 10%, preferably 2 to 20%, in terms of the total weight of the coating base to the weight of the plain tablets containing the compound represented by the general formula (I) or a salt thereof.

When a reducing sugar is used for preparing the pharmaceutical composition comprising a compound represented by the general formula (I) or a salt thereof as an active ingredient, a stable pharmaceutical composition can be prepared by preparing the composition so that the compound represented by the general formula (I) or a salt thereof and the reducing sugar should not directly contact with each other.

Specifically, granules are prepared by dry granulation or wet granulation by using a compound represented by the general formula (I) or a salt thereof and a pharmaceutically acceptable carrier other than a reducing sugar or a carrier containing a reducing sugar, and then a solution of a polymer compound or the like is sprayed on the resulting granules with a manufacturing machine such as a film coating machine (Doria Coater, Freund Corporation), fluidized bed granulator (Flow Coater, Freund Corporation) or rotating fluidized bed coating machine (Multiplex, Powlex) to coat the granules with the polymer or the like. Without preparation of the granules, powder of a compound represented by the general formula (I) or a salt thereof may be coated with a polymer or the like.

Although the substance used for the coating, for example, polymer compound, is not particularly limited so far that the substance is usually used, pharmaceutically acceptable substances are preferred. Specific examples include polymers such as hydroxypropylmethylcellulose, hydroxypropylcellulose, povidone, aminoalkyl methacrylate copolymer, methacrylic acid copolymer, and ethylcellulose, and sugars such as mannitol, erythritol, and sucrose.

By mixing the coated granules containing a compound represented by the general formula (I) or a salt thereof prepared as described above and a reducing sugar and/or a carrier containing a reducing sugar as an ingredient (for example, granules containing a reducing sugar and the like), granules or fine granules can be obtained. Further, by filling the granules obtained by the aforementioned mixing into capsules, capsule preparation can be obtained. By compressing the resulting granules with a tableting machine or the like, tablets can be obtained.

In the case of tablet, for example, as in the preparation of three-layer tablet, a powder layer consisting of substances other than a reducing sugar can be formed on a powder layer containing a compound represented by the general formula (I) or a salt thereof in a mortar of tableting machine, and then a powder layer containing a reducing sugar or a carrier containing a reducing sugar as a component is further formed thereon, and further the layers can be compressed to prepare a tablet. By such a means, direct contact of the reducing sugar and the compound represented by the general formula (I) or a salt thereof can be avoided. As in the case of nucleated tablet, a tablet in which direct contact of the reducing sugar and the compound represented by the general formula (I) or a salt thereof is avoided can also be manufactured by preparing a tablet serving as a nucleus by using powder containing a compound represented by the general formula (I) or a salt thereof, and then coating this nucleus tablet with a substance other than a reducing sugar, and further, at the time of tableting, forming a powder layer containing a reducing sugar in a mortar of a tableting machine, putting the coated nucleus tablet onto the layer, further putting powder containing a reducing sugar thereon, and performing compression molding to make a tablet. Such a pharmaceutical composition prepared by using a compound represented by the general formula (I) or a salt thereof and a pharmaceutically acceptable carrier other than a reducing sugar and/or a carrier containing a reducing sugar as an ingredient, or a pharmaceutical composition in which contact of a reducing sugar and/or a carrier containing a reducing sugar as an ingredient and a compound represented by the general formula (I) or a salt thereof is avoided, which is prepared as described above, is a stable pharmaceutical composition in which generation of decomposition products is reduced or eliminated, and coloring is also reduced or eliminated even after storage, for example, at 60° C. for 2 weeks.

Although amount of a compound represented by the general formula (I) or a salt thereof contained in a unit dosage form of the pharmaceutical composition stabilized as described above is not particularly limited, examples usually include 1 to 2000 mg, preferably 10 to 1000 mg, more preferably 20 to 200 mg. The unit dosage form is usually administered orally, and the dose thereof may be appropriately chosen depending on age, weight, severity of symptoms, and the like of patients. In general, 1 to 2000 mg of a compound represented by the general formula (I) or a salt thereof can be administered per day for adults once or several times as divided portions. As for administration period, administration is generally performed every day for several weeks to several months. However, the daily dose and the administration period may be increased or decreased depending on symptoms of patients.

The present invention provides a method for preparing a pharmaceutical composition comprising a compound represented by the general formula (I) or a salt thereof according to [1] mentioned above as an active ingredient together with a pharmaceutically acceptable carrier, which comprises the step of preparing the pharmaceutical composition by using a carrier other than a reducing sugar and/or a carrier containing a reducing sugar as an ingredient as the pharmaceutically acceptable carrier, or when a reducing sugar and/or a carrier containing a reducing sugar as an ingredient is used as the pharmaceutically acceptable carrier, with eliminating contact of the reducing sugar and the compound represented by the general formula (I) or a salt thereof. Preferred examples of the compound represented by the general formula (I) or a salt thereof contained in the pharmaceutical composition to be prepared include, for example, the compound represented by the general formula (I) or a salt thereof defined in any one of [6] to [32] mentioned above, which are described as preferred embodiments.

The present invention also provides a method for stabilizing a pharmaceutical composition comprising a compound represented by the general formula (I) or a salt thereof according to [1] mentioned above as an active ingredient together with a pharmaceutically acceptable carrier, which comprises the step of preparing the pharmaceutical composition by using a carrier other than a reducing sugar and/or a carrier containing a reducing sugar as an ingredient as the pharmaceutically acceptable carrier, or when a reducing sugar and/or a carrier containing a reducing sugar as an ingredient is used as the pharmaceutically acceptable carrier, with eliminating contact of the reducing sugar and the compound represented by the general formula (I) or a salt thereof. Preferred examples of the compound represented by the general formula (I) or a salt thereof contained in the pharmaceutical composition to be stabilized include, for example, the compound represented by the general formula (I) or a salt thereof defined in any one of [6] to [32] mentioned above, which are described as preferred embodiments.

The present invention further provides a method for storing and/or distributing a pharmaceutical composition comprising a compound represented by the general formula (I) or a salt thereof according to [1] mentioned above as an active ingredient together with a pharmaceutically acceptable carrier, wherein the pharmaceutical composition, which is prepared by using a carrier other than a reducing sugar and/or a carrier containing a reducing sugar as an ingredient as the pharmaceutically acceptable carrier, or when a reducing sugar and/or a carrier containing a reducing sugar as an ingredient is used as the pharmaceutically acceptable carrier, with eliminating contact of the reducing sugar and the compound represented by the general formula (I) or a salt thereof, is stored and/or distributed with maintaining quality of the composition. By this method, quality of a pharmaceutical composition comprising a compound represented by the general formula (I) or a salt thereof as an active ingredient can be maintained, more specifically, decomposition and/or coloring of the active ingredient can be reduced or eliminated during storage and/or distribution thereof. As for the period for which the quality should be maintained, examples of the period for which marked degradation of the quality does not observed include a period of about 1 weeks to 2 years. Preferred examples of the compound represented by the general formula (I) or a salt thereof contained in the pharmaceutical composition of which quality should be maintained include, for example, the compound represented by the general formula (I) or a salt thereof defined in any one of [6] to [32] mentioned above, which are described as preferred embodiments.

EXAMPLES

The present invention will be further specifically explained with reference to preparation examples, examples, comparative examples and test examples. However, the scope of the present invention is not limited to the following examples.

Preparation Example 1

Preparation of 3-[3-amino-4-(indan-2-yloxy)-5-(1-methyl-1H-indazol-5-yl)phenyl]propionic acid 3-[3-Amino-4-(indan-2-yloxy)-5-(1-methyl-1H-indazol-5-yl)phenyl]propionic acid was prepared according to the preparation method of WO03/070686, Example 567.

Preparation Example 2

Preparation of 3-{3-amino-4-[2-(4-methylphenyl)ethyloxy]-5-(naphthalen-2-yl)phenyl}propionic acid 3-{3-Amino-4-[2-(4-methylphenyl)ethyloxy]-5-(naphthalen-2-yl)phenyl}propionic acid was prepared according to the preparation method of WO03/070686, Example 345.

Preparation Example 3

Preparation of 3-[3-amino-4-cyclopentylmethyloxy-5-(1H-indol-5-yl)phenyl]propionic acid 3-[3-Amino-4-cyclopentylmethyloxy-5-(1H-indol-5-yl)phenyl]propionic acid was prepared according to the preparation method of WO03/070686, Example 266.

Preparation Example 4

Preparation of 3-[3-amino-4-cyclopentylmethyloxy-5-(1-methyl-1H-indol-5-yl)phenyl]propionic acid 3-[3-Amino-4-cyclopentylmethyloxy-5-(1-methyl-1H-indol-5-yl)phenyl]propionic acid was prepared according to the preparation method of WO03/070686, Example 269.

Preparation Example 5

Preparation of 3-[3-amino-4-(indan-2-yloxy)-5-(1H-indazol-5-yl)phenyl]propionic acid 3-[3-Amino-4-(indan-2-yloxy)-5-(1H-indazol-5-yl)phenyl]propionic acid was prepared according to the preparation method of WO03/070686, Example 486.

Preparation Example 6

Preparation of methyl 3-[3-amino-4-(indan-2-yloxy)-5-(1-methyl-1H-indazol-5-yl)phenyl]propionate THF (40 ml) was added to methyl 3-[3-bromo-4-(indan-2-yloxy)-5-nitrophenyl]propionate (14.00 g, prepared according to the method of International Patent Publication WO03/70686), 1-methyl-1H-indazol-5-boronic acid (7.62 g, prepared according to the method of International Patent Publication WO03/70686), palladium acetate (75 mg, Wako Pure Chemical Industries) and triphenylphosphine (0.17 g, Wako Pure Chemical Industries), and the mixture was stirred. Then, a solution dissolving tripotassium phosphate (16.97 g, Wako Pure Chemical Industries) in water (27 ml) was added to the above mixture, and the interior of the system was purged with nitrogen. Then, this mixture was stirred for 4 hours at 60° C. to allow the reaction. After confirming the completion of the reaction, the reaction solution was partitioned to obtain the upper layer. The upper layer was cooled to room temperature, ethyl acetate (40 ml) and activated carbon (2.8 g, Japan Envirochemicals) were added thereto, and the mixture was further stirred for 1 hour at room temperature. The suspension was filtered to obtain a filtrate, and the residue on the filter was washed with ethyl acetate (20 ml) to obtain the wash solution. The filtrate and the wash solution were combined and concentrated under reduced pressure to obtain a concentrate (44 g). Then, acetone (140 ml) was added to the concentrate. The mixture was stirred and water (140 ml) was added thereto over 1 hour with stirring. The mixture was further stirred for another 1 hour at room temperature. Then, this mixture was filtered, the solid on the filter was washed with water (70 ml), and wet solid was obtained. This wet solid was dried under reduced pressure at 50° C. to obtain crystals of methyl 3-[4-(indan-2-yloxy)-3-(1-methyl-1H-indazol-5-yl)-5-nitrophenyl]propionate (15.7 g).

To methyl 3-[4-(indan-2-yloxy)-3-(1-methyl-1H-indazol-5-yl)-5-nitrophenyl]propionate (13.0 g), THF (138 ml), stabilized nickel (4.42 g, NIKKI CHEMICAL) and water (4 ml) were added, the mixture was stirred, then the interior of the system was purged with hydrogen, and the reaction was allowed under a hydrogen atmosphere at 50° C. for 7 hours with stirring. After confirming the completion of the reaction, the reaction solution was purged with nitrogen and filtered to obtain a filtrate, and the residue on the filter was washed with THF (34 ml) to obtain a wash solution. The filtrate and the wash solution were combined, activated carbon (2.6 g, Japan Envirochemical) was added to the combined solution, and the mixture was stirred for 1 hour at room temperature. The suspension was filtered to obtain a filtrate, and the residue on the filter was washed with THF (34 ml) to obtain a wash solution. Then, the resulting filtrate and the wash solution were combined, water (207 ml) was added to the combined solution over 1 hour, and the mixture was stirred for another 1 hour under ice cooling. Then, this mixture was filtered, and the solid on the filter was washed with water (68 ml) to obtain wet solid. This wet solid was dried under reduced pressure at 50° C. to obtain crystals of methyl 3-[3-amino-4-(indan-2-yloxy)-5-(1-methyl-1H-indazol-5-yl)phenyl]propionate (10.3 g).

Preparation Example 7

Preparation of Type a Crystals of Compound 1 of the Present Invention

Methanol (45 ml) was added to methyl 3-[3-amino-4-(indan-2-yloxy)-5-(1-methyl-1H-indazol-5-yl)phenyl]propionate (10.0 g) obtained in Preparation Example 6, and the mixture was stirred. Then, a 2 N aqueous solution of sodium hydroxide (17.0 ml) was added to the above solution, and the mixture was stirred for 3 hours at 60° C. to perform alkali hydrolysis. After the reaction, the reaction solution was cooled to 35° C., and a 2 N aqueous solution of hydrochloric acid (17.0 ml) was added thereto over 2 hours, which was further stirred for 16 hours at 35° C. Then, this mixture was filtered, and the solid on the filter was washed with a mixture of water (27 ml) and methanol (13 ml) to obtain wet solid. This wet solid was dried under reduced pressure at 50° C. to obtain 9.2 g of crystals.

Preparation Example 8

Preparation of Type B Crystals of Compound 1 of the Present Invention 1

Acetone (17 ml) was added to the type A crystals of Compound 1 of the present invention (1.0 g) prepared according to Preparation Example 7 and the mixture was heated on a water bath at 60° C. to dissolve the crystals. Then, the solution was stirred overnight at room temperature. The generated precipitates were filtered and solid was obtained on the filter. Then, the solid was dried under reduced pressure at 50° C. to obtain 0.55 g of crystals.

Preparation Example 9

Preparation of Type B Crystals of Compound 1 of the Present Invention 2

Dichloromethane (31 ml) was added to the type A crystals of Compound 1 of the present invention (1.0 g) prepared according to Preparation Example 7, and the mixture was heated on a water bath at 40° C. to dissolve the crystals. Then, the solution was stirred overnight at room temperature. The generated precipitates were filtered, and solid was obtained on the filter. Then, the solid was dried under reduced pressure at 50° C. to obtain 0.81 g of crystals.

The crystals showed a spectrum which is substantially identical to that of FIG. 5 in a differential scanning calorimetric analysis according to Test Example 2 that will be described later, and thus were confirmed to be type B crystals of Compound 1 of the present invention.

Preparation Example 10

Preparation of Type B Crystals of Compound 1 of the Present Invention 3

Methanol (45 ml) was added to the type A crystals of Compound 1 of the present invention (10.0 g) prepared according to Preparation Example 7, and the mixture was stirred. Then, a 2 N aqueous solution of sodium hydroxide (17.0 ml) was added to the mixture, and the mixture was stirred for 1 hour at 60° C. This mixture was cooled to 35° C., and a 2 N aqueous solution of hydrochloric acid (7.0 ml) was added thereto over 30 minutes. After confirming that pH of the mixture reached 7 to 9, the seed crystals of the type B crystals of Compound 1 of the present invention (0.1 g) prepared according to Preparation Example 8 were immediately added, and the mixture was further stirred for 10 minutes. Then, a 2 N aqueous solution of hydrochloric acid (10.0 ml) was added to this mixture over 1 hour, and the mixture was further stirred for 2 hours at 35° C. Then, this mixture was filtered and the solid on the filter was washed with a mixture of water (27 ml) and methanol (13 ml) to obtain wet solid. This wet solid was dried under reduced pressure at 50° C. to obtain 9.7 g of white crystals.

The crystals showed a spectrum which is substantially identical to that of FIG. 4 in a powder X-ray diffraction measurement according to Test Example 1 that will be described later, and thus were confirmed to be type B crystals of Compound 1 of the present invention. Also, the crystals showed a spectrum which is substantially identical to that of FIG. 5 in a differential scanning calorimetric analysis according to Test Example 2 that will be described later, and thus were confirmed to be type B crystals of Compound 1 of the present invention.

Preparation Example 11

Preparation of Type B Crystals of Compound 1 of the Present Invention 4

Methanol (360.0 ml) was added to methyl 3-[3-amino-4-(indan-2-yloxy)-5-(1-methyl-1H-indazol-5-yl)phenyl]propionate (80.0 g) obtained by a process in accordance with Preparation Example 6, and the mixture was stirred. Then, water (36.2 ml) and a 2 N aqueous solution of sodium hydroxide (99.7 ml) were added to the mixture, and the resultant solution was subjected to alkali hydrolysis with stirring at 60° C. for 3 hours. After the reaction, impurities such as fine dusts in the reaction solution were separated by filtration, water (180.2 ml) was added, and then the mixture was adjusted to 35° C. A 2 N aqueous solution of hydrochloric acid (10.7 ml) was added to the mixture over 8 minutes, and after confirming that pH of the mixture reached 7.9, the seed crystals of the type B crystals of Compound 1 of the present invention (0.08 g) prepared according to Preparation Example 8 were immediately added, and the resultant was stirred for 4 minutes. Then, a 2 N aqueous solution of hydrochloric acid (89.0 ml) was added to this mixture over 111 minutes, and the mixture was stirred for 14.3 hours at 35° C. Then, this mixture was filtered, and the solid on the filter was washed with a mixture of water (213.4 ml) and methanol (106.7 ml) to obtain wet solid. To this wet solid, water (213.4 ml) and methanol (106.7 ml) were added again to form a mixture, and the mixture was stirred for 37 minutes at 18 to 20° C. Then, this mixture was filtered, and the solid on the filter was washed with a mixture of water (21.3 ml) and methanol (10.7 ml) to obtain wet solid. This wet solid was dried under reduced pressure at 50° C. to obtain 76.28 g of white crystals.

These crystals showed a spectrum which is substantially identical to that of FIG. 5 in a differential scanning calorimetric analysis according to Test Example 2 that will be described later, and thus were confirmed to be type B crystals of Compound 1 of the present invention.

Preparation Example 12

Preparation of Mixed Crystals of Compound 1 of the Present Invention 1

0.9 g of type A crystals of Compound 1 of the present invention prepared according to Preparation Example 7 and 0.1 g of type B crystals prepared according to Preparation Example 8 were mixed using a mortar and a pestle to obtain a mixture containing 90% of type A crystals and 10% of type B crystals.

Preparation Example 13

Preparation of Mixed Crystals of Compound 1 of the Present Invention 2

0.1 g of type A crystals of Compound 1 of the present invention prepared according to Preparation Example 7 and 0.9 g of type B crystals prepared according to Preparation Example 8 were mixed using a mortar and a pestle to obtain a mixture containing 10% of type A crystals and 90% of type B crystals.

Example 1

The compound obtained according to the method of Preparation Example 7 (10 g) and crystalline cellulose (10 g, Asahi Kasei Chemicals) were mixed in a chemical mill for 3 minutes to obtain mixed powder.

Example 2

The compound obtained according to the method of Preparation Example 7 (10 g) and D-mannitol (10 g, Towa Chemical Industry) were mixed in a chemical mill for 3 minutes to obtain mixed powder.

Example 3

The compound obtained according to the method of Preparation Example 7 (10 g) and methylcellulose (10 g, Shin-Etsu Chemical) were mixed in a chemical mill for 3 minutes to obtain mixed powder.

Example 4

The compound obtained according to the method of Preparation Example 7 (10 g) and croscarmellose sodium (10 g, Asahi Kasei Chemicals) were mixed in a chemical mill for 3 minutes to obtain mixed powder.

Example 5

The compound obtained according to the method of Preparation Example 7 (10 g) and anhydrous calcium hydrogenphosphate (10 g, Kyowa Chemical Industry) were mixed in a chemical mill for 3 minutes to obtain mixed powder.

Example 6

The compound obtained according to the method of Preparation Example 7 (10 g) and corn starch (10 g, Nihon Shokuhin Kako) were mixed in a chemical mill for 3 minutes to obtain mixed powder.

Example 7

The compound obtained according to the method of Preparation Example 7 (10 g) and hydroxypropylcellulose (10 g, Nippon Soda) were mixed in a chemical mill for 3 minutes to obtain mixed powder.

Example 8

The compound obtained according to the method of Preparation Example 7 (10 g) and crospovidone (10 g, BASF) were mixed in a chemical mill for 3 minutes to obtain mixed powder.

Example 9

The compound obtained according to the method of Preparation Example 7 (10 g) and sucrose (10 g, Mitsui Sugar) were mixed in a chemical mill for 3 minutes to obtain mixed powder.

Example 10

The compound obtained according to the method of Preparation Example 7 (10 g) and povidone (10 g, BASF) were mixed in a chemical mill for 3 minutes to obtain mixed powder.

Example 11

The compound obtained according to the method of Preparation Example 7 (10 g) and sodium carboxymethyl starch (10 g, DMV) were mixed in a chemical mill for 3 minutes to obtain mixed powder.

Example 12

The compound obtained according to the method of Preparation Example 7 (10 g) and low substituted hydroxypropylcellulose (10 g, Shin-Etsu Chemical) were mixed in a chemical mill for 3 minutes to obtain mixed powder.

Example 13

The compound obtained according to the method of Preparation Example 7 (10 g) and partially pregelatinized starch (10 g, Asahi Kasei Chemicals) were mixed in a chemical mill for 3 minutes to obtain mixed powder.

Example 14

The compound obtained according to the method of Preparation Example 7 (10 g) and hydroxypropylmethylcellulose (10 g, Shin-Etsu Chemical) were mixed in a chemical mill for 3 minutes to obtain mixed powder.

Example 15

The compound obtained according to the method of Preparation Example 7 (10 g) and erythritol (10 g, Nikken Fine Chemicals) were mixed in a chemical mill for 3 minutes to obtain mixed powder.

Example 16

The compound obtained according to the method of Preparation Example 7 (10 g) and carmellose (10 g, Gotoku Chemical) were mixed in a chemical mill for 3 minutes to obtain mixed powder.

Example 17

The compound obtained according to the method of Preparation Example 7 (10 g) and polyvinyl alcohol (10 g, Shin-Etsu Chemical) were mixed in a chemical mill for 3 minutes to obtain mixed powder.

Example 18

The compound obtained according to the method of Preparation Example 7 (10 g) and trehalose (10 g, Hayashibara) were mixed in a chemical mill for 3 minutes to obtain mixed powder.

Example 19

The compound obtained according to the method of Preparation Example 7 (10 g) and carmellose calcium (10 g, Gotoku Chemical) were mixed in a chemical mill for 3 minutes to obtain mixed powder.

Example 20

The compound obtained according to the method of Preparation Example 7 (10 g) and carmellose sodium (10 g, Daiichi Kogyo Seiyaku) were mixed in a chemical mill for 3 minutes to obtain mixed powder.

Example 21

The compound obtained according to the method of Preparation Example 10 (10 g) and D-mannitol (10 g, Towa Chemical Industry) were mixed in a chemical mill for 3 minutes to obtain mixed powder.

Example 22

The compound obtained according to the method of Preparation Example 10 (10 g) and crystalline cellulose (10 g, Asahi Kasei Chemicals) were mixed in a chemical mill for 3 minutes to obtain mixed powder.

Example 23

The compound obtained according to the method of Preparation Example 10 (10 g) and povidone (10 g, BASF) were mixed in a chemical mill for 3 minutes to obtain mixed powder.

Example 24

The compound obtained according to the method of Preparation Example 10 (10 g) and sodium carboxymethyl starch (10 g, DMV) were mixed in a chemical mill for 3 minutes to obtain mixed powder.

Example 25

The compound obtained according to the method of Preparation Example 10 (30 g), erythritol (60 g, Nikken Fine Chemicals), corn starch (138 g, Nihon Shokuhin Kako), carmellose (10 g, Gotoku Chemical) and polyvinyl alcohol (10 g, Shin-Etsu Chemical) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 7.

Example 26

The compound obtained according to the method of Preparation Example 10 (30 g), trehalose (60 g, Hayashibara), corn starch (138 g, Nihon Shokuhin Kako), carmellose calcium (10 g, Gotoku Chemical) and hydroxypropylmethylcellulose (10 g, Shin-Etsu Chemical) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 7.

Example 27

The compound obtained according to the method of Preparation Example 7 (30 g), trehalose (60 g, Hayashibara), low substituted hydroxypropylcellulose (Shin-Etsu Chemical) 138 g, partially pregelatinized starch (10 g, Asahi Kasei Chemicals) and polyvinyl alcohol (10 g, Shin-Etsu Chemical) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 7.

Example 28

The compound obtained according to the method of Preparation Example 7 (30 g), erythritol (60 g, Nikken Fine Chemicals), corn starch (138 g, Nihon Shokuhin Kako), carmellose calcium (10 g, Gotoku Chemical) and carmellose sodium (10 g, Dai-ichi Kogyo Seiyaku) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 7.

Example 29

The compound obtained according to the method of Preparation Example 7 (30 g), trehalose (60 g, Hayashibara), corn starch (138 g, Nihon Shokuhin Kako), partially pregelatinized starch (10 g, Asahi Kasei Chemicals) and polyvinyl alcohol (10 g, Shin-Etsu Chemical) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 7.

Example 30

The compound obtained according to the method of Preparation Example 7 (30 g), trehalose (60 g, Hayashibara), low substituted hydroxypropylcellulose (Shin-Etsu Chemical) 138 g, carmellose (10 g, Gotoku Chemical) and carmellose sodium (10 g, Dai-ichi Kogyo Seiyaku) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 7.

Example 31

The compound obtained according to the method of Preparation Example 10 (30 g), crystalline cellulose (60 g, Asahi Kasei Chemicals), D-mannitol (138 g, Towa Chemical Industry), methylcellulose (10 g, Shin-Etsu Chemical) and croscarmellose sodium (10 g, Asahi Kasei Chemicals) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 7.

Example 32

The compound obtained according to the method of Preparation Example 7 (30 g), crystalline cellulose (60 g, Asahi Kasei Chemicals), D-mannitol (138 g, Towa Chemical Industry), povidone (10 g, BASF) and sodium carboxymethyl starch (10 g, DMV) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 7.

Example 33

The compound obtained according to the method of Preparation Example 7 (30 g), crystalline cellulose (60 g, Asahi Kasei Chemicals), anhydrous calcium hydrogenphosphate (138 g, Kyowa Chemical Industry), methylcellulose (10 g, Shin-Etsu Chemical) and crospovidone (10 g, BASF) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 7.

Example 34

The compound obtained according to the method of Preparation Example 7 (30 g), crystalline cellulose (60 g, Asahi Kasei Chemicals), anhydrous calcium hydrogenphosphate (138 g, Kyowa Chemical Industry), hydroxypropylcellulose (10 g, Nippon Soda) and sodium carboxymethyl starch (10 g, DMV) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 7.

Example 35

The compound obtained according to the method of Preparation Example 7 (30 g), crystalline cellulose (60 g, Asahi Kasei Chemicals), anhydrous calcium hydrogenphosphate (138 g, Kyowa Chemical Industry), povidone (10 g, BASF) and croscarmellose sodium (10 g, Asahi Kasei Chemicals) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 7.

Example 36

The compound obtained according to the method of Preparation Example 7 (30 g), crystalline cellulose (60 g, Asahi Kasei Chemicals), sucrose (138 g, Mitsui Sugar), methylcellulose (10 g, Shin-Etsu Chemical) and sodium carboxymethyl starch (10 g, DMV) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 7.

Example 37

The compound obtained according to the method of Preparation Example 7 (30 g), crystalline cellulose (60 g, Asahi Kasei Chemicals), sucrose (138 g, Mitsui Sugar), hydroxypropylcellulose (10 g, Nippon Soda) and croscarmellose sodium (10 g, Asahi Kasei Chemicals) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 7.

Example 38

The compound obtained according to the method of Preparation Example 7 (30 g), crystalline cellulose (60 g, Asahi Kasei Chemicals), sucrose (138 g, Mitsui Sugar), povidone (10 g, BASF) and crospovidone (10 g, BASF) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 7.

Example 39

The compound obtained according to the method of Preparation Example 10 (30 g), crystalline cellulose (60 g, Asahi Kasei Chemicals), anhydrous calcium hydrogenphosphate (138 g, Kyowa Chemical Industry), hydroxypropylcellulose (10 g, Nippon Soda) and crospovidone (10 g, BASF) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 10.

Example 40

The compound obtained according to the method of Preparation Example 10 (30 g), corn starch (60 g, Nihon Shokuhin Kako), D-mannitol (138 g, Towa Chemical Industry), methylcellulose (10 g, Shin-Etsu Chemical) and croscarmellose sodium (10 g, Asahi Kasei Chemicals) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 7.

Example 41

The compound obtained according to the method of Preparation Example 10 (30 g), corn starch (60 g, Nihon Shokuhin Kako), anhydrous calcium hydrogenphosphate (138 g, Kyowa Chemical Industry), hydroxypropylcellulose (10 g, Nippon Soda) and sodium carboxymethyl starch (10 g, DMV) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 10.

Example 42

The compound obtained according to the method of Preparation Example 10 (30 g), erythritol (60 g, Nikken Fine Chemicals), corn starch (138 g, Nihon Shokuhin Kako), carmellose (10 g, Gotoku Chemical) and polyvinyl alcohol (10 g, Shin-Etsu Chemical) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 10.

Example 43

The compound obtained according to the method of Preparation Example 10 (30 g), trehalose (60 g, Hayashibara), corn starch (138 g, Nihon Shokuhin Kako), carmellose calcium (10 g, Gotoku Chemical) and hydroxypropylmethylcellulose (10 g, Shin-Etsu Chemical) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 10.

Example 44

The compound obtained according to the method of Preparation Example 10 (1000 g), crystalline cellulose (500 g, Asahi Kasei Chemicals), D-mannitol (138 g, Merck), povidone (100 g, BASF) and sodium carboxymethyl starch (100 g, DMV) were mixed with a high speed mixer (Fukae Kogyo) at a blade revolution number of 135 RPM. After the mixing, purified water (500 g) was added to the mixture, and the mixture was granulated at the same revolution number. The produced granules were dried with Flow Coater (Freund Corporation) at an intake temperature of 70° C., and after drying, granulated by passing them through a 813 μm mesh. Magnesium stearate (30 g, Merck) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 10.

Comparative Example 1

The compound obtained according to the method of Preparation Example 7 (10 g) and xylose (10 g) were mixed in a chemical mill for 3 minutes to obtain mixed powder.

Comparative Example 2

The compound obtained according to the method of Preparation Example 7 (10 g) and lactose (10 g) were mixed in a chemical mill for 3 minutes to obtain mixed powder.

Comparative Example 3

The compound obtained according to the method of Preparation Example 7 (10 g) and glucose (10 g) were mixed in a chemical mill for 3 minutes to obtain mixed powder.

Comparative Example 4

The compound obtained according to the method of Preparation Example 7 (10 g) and maltose (10 g) were mixed in a chemical mill for 3 minutes to obtain mixed powder.

Comparative Example 5

The compound obtained according to the method of Preparation Example 7 (30 g), lactose (60 g, DMV), low substituted hydroxypropylcellulose (Shin-Etsu Chemical) 138 g, carmellose calcium (10 g, Gotoku Chemical) and polyvinyl alcohol (10 g, Shin-Etsu Chemical) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 7.

Comparative Example 6

The compound obtained according to the method of Preparation Example 7 (30 g), lactose (60 g, DMV), synthetic aluminium silicate (138 g, Kyowa Chemical Industry), partially pregelatinized starch (10 g, Asahi Kasei Chemicals) and carmellose sodium (10 g, Dai-ichi Kogyo Seiyaku) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 7.

Comparative Example 7

The compound obtained according to the method of Preparation Example 7 (30 g), lactose (60 g, DMV), corn starch (138 g, Nihon Shokuhin Kako), partially pregelatinized starch (10 g, Asahi Kasei Chemicals) and carmellose sodium (10 g, Dai-ichi Kogyo Seiyaku) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 7.

Comparative Example 8

The compound obtained according to the method of Preparation Example 7 (30 g), lactose (60 g, DMV), synthetic aluminium silicate (138 g, Kyowa Chemical Industry), carmellose calcium (10 g, Gotoku Chemical) and polyvinyl alcohol (10 g, Shin-Etsu Chemical) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 7.

Comparative Example 9

The compound obtained according to the method of Preparation Example 7 (30 g), glucose (60 g, Wako Pure Chemical Industries), crystalline cellulose (138 g, Asahi Kasei Chemicals), sodium carboxymethyl starch (10 g, DMV) and povidone (10 g, BASF) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 7.

Comparative Example 10

The compound obtained according to the method of Preparation Example 7 (30 g), xylose (60 g, Wako Pure Chemical Industries), crystalline cellulose (138 g, Asahi Kasei Chemicals), sodium carboxymethyl starch (10 g, DMV) and povidone (10 g, BASF) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 7.

Comparative Example 11

The compound obtained according to the method of Preparation Example 7 (30 g), fructose (60 g, Wako Pure Chemical Industries), crystalline cellulose (138 g, Asahi Kasei Chemicals), sodium carboxymethyl starch (10 g, DMV) and povidone (10 g, BASF) were mixed in Mechanomill (Okada Seiko) at a blade revolution number of 500 RPM. After the mixing, purified water (40 g) was added to the mixture, and the mixture was granulated at the same revolution number. The produced granules were dried by leaving stand at 50° C. for 8 hours, and after drying, granulated by passing them through a 600 μm mesh. Magnesium stearate (2 g, Taihei Chemical Industrial) was added to the granules, and mixed in a V shape blender for 5 minutes to obtain powder for tableting. The powder was compressed by using 12R mortar and pestle having a diameter of 8 mm to obtain tablets (plain tablets) each having a weight of 250 mg and containing 30 mg of the compound obtained according to the method of Preparation Example 7.

Experimental Example 1

The mixed powders obtained in Example 1 to 24 and Comparative Example 1 to 4 were each put into a glass bottle in an amount of 1 g, and after a lid was put on the bottle, stored at 60° C. for 2 weeks under a closed state. Total amounts of decomposition products observed after the storage are shown in Table 1.

TABLE 1

| Example | | Total amount of decomposition products (%) |
|---|---|---|
| Example | 1 | 0.15 |
| | 2 | 0.13 |
| | 3 | 0.16 |
| | 4 | 0.14 |
| | 5 | 0.14 |
| | 6 | 0.13 |
| | 7 | 0.17 |
| | 8 | 0.16 |
| | 9 | 0.13 |
| | 10 | 0.16 |
| | 11 | 0.15 |
| | 12 | 0.13 |
| | 13 | 0.14 |
| | 14 | 0.13 |
| | 15 | 0.15 |
| | 16 | 0.17 |
| | 17 | 0.15 |
| | 18 | 0.20 |
| | 19 | 0.13 |
| | 20 | 0.19 |
| | 21 | 0.06 |
| | 22 | 0.06 |
| | 23 | 0.06 |
| | 24 | 0.09 |
| Comparative Example | 1 | 1.58 |
| | 2 | 0.24 |
| | 3 | 0.80 |
| | 4 | 0.24 |

The compound obtained according to the method of Preparation Example 7 was extracted from each powder used for the experiment with a 50% acetonitrile aqueous solution, and the total amounts of decomposition products were obtained by HPLC under the following conditions.

HPLC Conditions
Detector: Ultraviolet absorptiometer (measurement wavelength: 235 nm)
Column: YMC-Pack Pro $C^{18}$, internal diameter: 4.6 mm, length: 15 cm (YMC)
Column temperature: Constant temperature around 40° C.
Mobile phase A: 50 mmol/L Monosodium phosphate aqueous solution
Mobile phase B: Acetonitrile
Feed of mobile phases: The mobile phases were fed so that a linear gradient of the mobile phase A ratio of 65% to 20% and the mobile phase B ratio of 35% to 80% should be formed over 45 minutes after the start of the experiment. From the point 45 minutes after the start to the end of experiment (60 minutes), the ratio of the mobile phase A was maintained to be 65%, and the ratio of the mobile phase B was maintained to be 35%.
Flow rate: 1.0 mL/minute As shown in Table 1, the total amounts of decomposition products observed after the storage were 0.20% or less and stable in all of Examples 1 to 24. Whilst, all of Comparative Examples 1 to 4 gave values exceeding 0.2%.

Experimental Example 2

The tablets obtained in Example 25 to 44 and Comparative Example 5 to 11 were each put into a glass bottle, and after a lid was put on the bottle, stored at 60° C. for 2 weeks under a closed state. Total amounts of decomposition products observed after the storage are shown in Table 2.

TABLE 2

| Example | | Total amount of decomposition products (%) |
|---|---|---|
| Example | 25 | 0.14 |
| | 26 | 0.14 |
| | 27 | 0.19 |
| | 28 | 0.18 |
| | 29 | 0.14 |
| | 30 | 0.18 |
| | 31 | 0.15 |
| | 32 | 0.18 |
| | 33 | 0.13 |
| | 34 | 0.17 |
| | 35 | 0.15 |
| | 36 | 0.14 |
| | 37 | 0.17 |
| | 38 | 0.16 |
| | 39 | 0.16 |
| | 40 | 0.17 |
| | 41 | 0.16 |
| | 42 | 0.19 |
| | 43 | 0.15 |
| | 44 | 0.06 |
| Comparative Example | 5 | 0.98 |
| | 6 | 3.68 |
| | 7 | 0.75 |
| | 8 | 4.18 |
| | 9 | 15.79 |
| | 10 | 83.64 |
| | 11 | 2.37 |

The tablets used for the experiment were ground, and the compound obtained according to the method of Preparation Example 7 was extracted from each obtained powder with a 50% acetonitrile aqueous solution. The total amounts of decomposition products were obtained by HPLC under the following conditions.

HPLC Conditions
Detector: Ultraviolet absorptiometer (measurement wavelength: 235 nm)
Column: YMC-Pack Pro $C^{18}$, internal diameter: 4.6 mm, length: 15 cm (YMC)
Column temperature: Constant temperature around 40° C.
Mobile phase A: 50 mmol/L Monosodium phosphate aqueous solution
Mobile phase B: Acetonitrile
Feed of mobile phases: The mobile phases were fed so that a linear gradient of the mobile phase A ratio of 65% to 20% and the mobile phase B ratio of 35% to 80% should be formed over 45 minutes after the start of the experiment. From the point 45 minutes after the start to the end of experiment (60 minutes), the ratio of the mobile phase A was maintained to be 65%, and the ratio of the mobile phase B was maintained to be 35%.
Flow rate: 1.0 mL/minute As shown in Table 2, it was confirmed that the total amounts of decomposition products observed after the storage were less than 0.20% in all the tablets of Examples 25 to 44, which contained no reducing sugar, whereas the total amounts of decomposition products were extremely large in the tablets of Comparative Examples 5 to 11 which contained a reducing sugar.

Experimental Example 3

The tablets obtained in Example 25 to 44 and Comparative Example 5 to 11 were each put into a glass bottle, and after a lid was put on the bottle, stored at 60° C. for 2 weeks under a closed state. Color differences ($\Delta E$) of the tablets observed after the storage are shown in Table 3.

TABLE 3

|  | | Color difference ($\Delta E$) |
|---|---|---|
| Example | 25 | 1.56 |
|  | 26 | 1.01 |
|  | 27 | 2.76 |
|  | 28 | 1.94 |
|  | 29 | 1.76 |
|  | 30 | 2.08 |
|  | 31 | 2.44 |
|  | 32 | 0.58 |
|  | 33 | 1.06 |
|  | 34 | 1.39 |
|  | 35 | 0.32 |
|  | 36 | 1.82 |
|  | 37 | 2.66 |
|  | 38 | 2.45 |
|  | 39 | 2.78 |
|  | 40 | 0.69 |
|  | 41 | 0.59 |
|  | 42 | 2.60 |
|  | 43 | 1.29 |
|  | 44 | 0.23 |
| Comparative Example | 5 | 5.97 |
|  | 6 | 25.72 |
|  | 7 | 6.13 |
|  | 8 | 23.78 |
|  | 9 | 25.71 |
|  | 10 | 70.01 |
|  | 11 | 32.40 |

Color difference ($\Delta E$) was measured for the tablets used for the experiment with a color difference meter (CLR-7100F, Shimadzu) provided with a condenser lens of 6 mm. As shown in Table 3, all of the tablets of Example 25 to 44 containing no reducing sugar gave $\Delta E$ lower than 3.0, and gave no change of appearance, whereas the tablets of Comparative Example 5 to 11 containing a reducing sugar gave a large value of $\Delta E$ and marked coloring.

Experimental Example 4

The compounds of Preparation Examples 2 to 5 and 7 were each weighed in an amount of 10 mg in a stoppered test tube, added with methanol (2 mL), dissolved in the methanol, and then further added with a glucose aqueous solution (1 mL) of 10 mg/mL concentration to prepare sample solutions. Separately, the compounds of Preparation Examples 2 to 5 and 7 were each weighed in an amount of 10 mg in a stoppered test tube, added with methanol (2 mL), dissolved in the methanol, and then further added with purified water (1 mL) to prepare control solutions. The prepared sample solutions and the control solutions were stored in an incubator (Minijet Oven, Toyama Sangyo) at 60° C. for 6 days. Degrees of the coloring of the solutions after the storage are shown in Table 4.

TABLE 4

|  | Sample solution after storage at 60° C. for 6 days | Control solution after storage at 60° C. for 6 days |
|---|---|---|
| Compound of Preparation Example 2 | + | − |
| Compound of Preparation Example 3 | ++ | − |
| Compound of Preparation Example 4 | ++ | − |
| Compound of Preparation Example 5 | + | − |
| Compound of Preparation Example 7 | ++ | − |

−: No coloring
+: Coloring
++: Marked coloring

The compounds of Preparation Examples 2 to 5 and 7, which are representative examples of the compound represented by the general formula (I), all gave coloring of solutions thereof by the influence of glucose, which is a reducing sugar.

Experimental Example 5

The compound obtained according to the method of Preparation Example 7 was weighed in an amount of 10 mg in a stoppered test tube, added with methanol (2 mL) for dissolution, and then further added with a 10 mg/mL aqueous solution of each of additives shown in Table 5 (1 mL) to prepare a sample solution. Separately, the compound obtained according to the method of Preparation Example 7 was weighed in an amount of 10 mg in a stoppered test tube, added with methanol (2 mL) for dissolution, and then further added with purified water (1 mL) to prepare a control solution. The prepared sample solutions and the control solution were stored in an incubator (Minijet Oven, Toyama Sangyo) at 60° C. for 6 days. Degrees of the coloring of the solutions after the storage are shown in Table 5.

TABLE 5

| Additive | Sample solution after storage at 60° C. for 6 days | Control solution after storage at 60° C. for 6 days |
|---|---|---|
| D-Mannitol | − | − |
| Erythritol | − | − |
| Trehalose | − | − |
| Sucrose | − | − |
| Fructose | + | − |
| Xylose | ++ | − |
| Lactose | + | − |
| Maltose | + | − |

−: No coloring
+: Coloring
++: Marked coloring

The compound obtained according to the method of Preparation Example 7 gave coloring of the solution thereof by the influence of fructose, xylose, lactose, and maltose, which are reducing sugars, but gave no coloring with D-mannitol, erythritol, trehalose and sucrose, which are non-reducing sugars.

Effect of the pharmaceutical composition of the present invention in which the compound represented by the general formula (I) consists of type B crystals of Compound 1 of the present invention can also be confirmed by the same method as mentioned above.

Experimental Example 6

The tablets obtained in Example 31 were ground in a mortar, 500.37 mg of the ground tablets were put into a 20-mL volumetric flask, and purified water was added to make the volume 20 mL. This solution was filtered through a 0.45-μm membrane filter to obtain a filtrate. This filtrate was measured in a volume of 1 mL in a test tube, and added with 1 mL of a copper reagent (prepared immediately before use by mixing 1 mL of Solution A prepared by adding purified water to 15 g of copper sulfate pentahydrate to a volume of 100 mL and 25 mL of Solution B prepared by dissolving 25 g of anhydrous sodium carbonate, 25 g of potassium sodium tartrate tetrahydrate, 20 g of sodium hydrogencarbonate and 200 g of anhydrous sodium sulfate in purified water in a volume of 1000 mL), and the test tube was stoppered, heated for 20 minutes on a boiling water bath, and then rapidly cooled for 5 minutes. The total volume of the cooled solution was transferred to a 10-mL volumetric flask, and added with 1 mL of the Nelson reagent solution (prepared by dissolving 25 g of ammonium molybdate tetrahydrate in 900 mL of purified water, adding 42 g of concentrated sulfuric acid and 3 g of disodium arsenate heptahydrate (dissolved in 50 mL of purified water beforehand) to the solution, and making the total volume of the mixture 1000 mL with water), the total volume of the mixture was made 10 mL in the volumetric flask by adding purified water, and the mixture was left for 15 minutes to obtain a sample solution. Absorbance of the resulting sample solution was measured at 500 nm by using purified water as blank, and found to be 0.0327.

Separately, 5.1 mg/L, 10.2 mg/L, and 30.7 mg/L glucose aqueous solutions were prepared, and absorbances thereof were measured at 500 nm by using purified water as blank, and found to be 0.0323, 0.0517, and 0.1079, respectively.

A calibration curve was prepared from the above results, and reducing sugar content (in terms of glucose) in tablets obtained in Example 31 was calculated and found to be 0.18% by weight.

Experimental Example 7

The tablets obtained in Example 44 were ground in a mortar, 501.98 mg of the ground tablets were put into a 20-mL volumetric flask, and purified water was added to make the volume 20 mL. This solution was filtered through a 0.45-μm membrane filter to obtain a filtrate. This filtrate was measured in a volume of 1 mL in a test tube, and added with 1 mL of a copper reagent (prepared immediately before use by mixing 1 mL of Solution A prepared by adding purified water to 15 g of copper sulfate pentahydrate to a volume of 100 mL and 25 mL of Solution B prepared by dissolving 25 g of anhydrous sodium carbonate, 25 g of potassium sodium tartrate tetrahydrate, 20 g of sodium hydrogencarbonate and 200 g of anhydrous sodium sulfate in purified water in a volume of 1000 mL), and the test tube was stoppered, heated for 20 minutes on a boiling water bath, and then rapidly cooled for 5 minutes. The total volume of the cooled solution was transferred to a 10-mL volumetric flask, and added with 1 mL of the Nelson reagent solution (prepared by dissolving 25 g of ammonium molybdate tetrahydrate in 900 mL of purified water, adding 42 g of concentrated sulfuric acid and 3 g of disodium arsenate heptahydrate (dissolved in 50 mL of purified water beforehand) to the solution, and adjusting the total volume of the mixture 1000 mL with water), the total volume of the mixture was made 10 mL in the volumetric flask by adding purified water, and the mixture was left stand for 15 minutes to obtain a sample solution. Absorbance of the resulting sample solution was measured at 500 nm by using purified water as blank, and found to be 0.0360.

Separately, 5.1 mg/L, 10.2 mg/L, and 30.7 mg/L glucose aqueous solutions were prepared, and absorbances thereof were measured at 500 nm by using purified water as blank, and found to be 0.0323, 0.0517, and 0.1079, respectively.

A calibration curve was prepared from the above results, and reducing sugar content (in terms of glucose) in tablets obtained in Example 44 was calculated and found to be 0.23% by weight.

Experimental Example 8

The tablets obtained in Examples 31 to 38 and 44 were each ground in a mortar, about 0.1 g of the ground tablets were put into a moisture heating evaporator (AQUA SOLID EVAPORATOR, Model LE-20S, Hiranuma Sangyo), and heated to 150° C., and moisture in the sample was introduced by using a nitrogen as a carrier into a titration flask of moisture content analyzer (AQUACOUNTER, Model AQV-7SF, Hiranuma Sangyo) containing methanol for moisture content measurement (Hayashi Pure Chemical Industry) beforehand. After the introduction, moisture content was measured by titration using a regent solution for moisture content measurement (Hydranal Composite 2, Hayashi Pure Chemical Industry). The measured moisture contents are shown in Table 6.

TABLE 6

| Example | Moisture content (weight %) |
| --- | --- |
| 31 | 1.4 |
| 32 | 1.5 |
| 33 | 1.7 |
| 34 | 1.6 |
| 35 | 1.8 |
| 36 | 1.3 |
| 37 | 1.5 |
| 38 | 1.7 |
| 44 | 1.5 |

Test Example 1

Powder X-Ray Diffraction

Powder X-ray diffraction analysis was conducted for the type A crystals of Compound 1 of the present invention obtained according to Preparation Example 7 of the present specification and the type B crystals of Compound 1 of the present invention obtained according to Preparation Example 10.

Measurement Conditions

X-ray diffraction apparatus: XRD-6000 manufactured by SHIMADZU

X-ray source: CuKα (40 kV, 30 mA)

Scan mode: continuous

Scan rate: 2°/min

Scanning step: 0.02°

Scan driving axis: θ-2 θ

Scan range: 5° to 40°

Scattering slit: 1°

Incident slit: 0.30 mm

The results of the measurement are as follows.

Type A crystals of Compound 1 of the present invention obtained in accordance with Preparation Example 7 were measured, and the spectrum shown in FIG. 1 was obtained. For the powder X-ray diffraction spectrum of the type A crystals of Compound 1 of the present invention, characteristic peaks were observed at 2θ s of 6.9°, 14.4°, 16.4°, 18.2°, 25.0° and 27.5°. Peaks were also observed at any or all of 20.0°, 20.7°, 22.9° and 25.4°, and any of these can also be construed at least as characteristic peaks. Furthermore, peaks were also observed at any or all of 10.2°, 12.7°, 15.0° or 23.8°, and any of these can also be construed at least as characteristic peaks.

Figure 4:
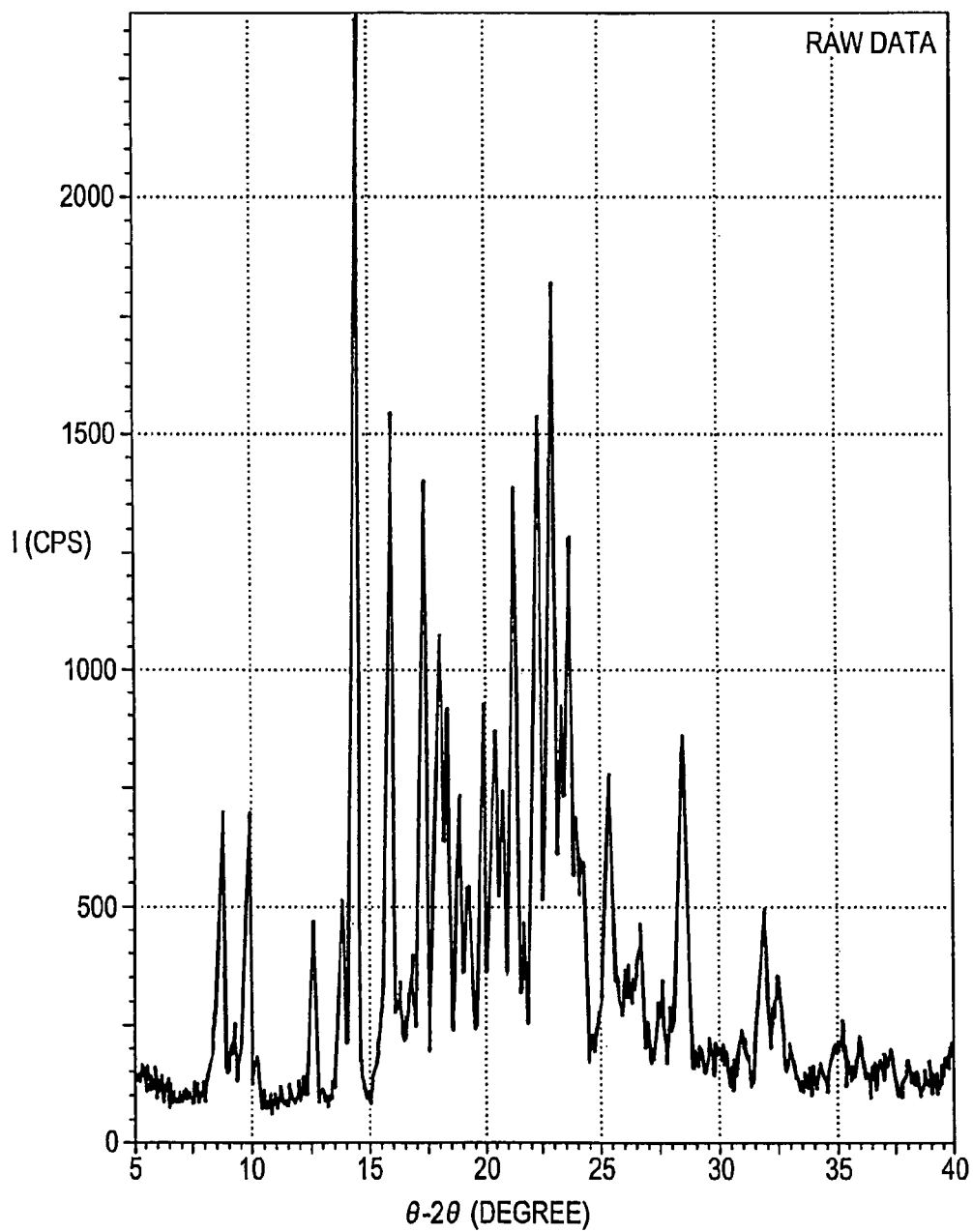
FIG. 4 A figure depicting powder X-ray diffraction spectrum of type B crystal of Compound 1 of the present invention. In the figure, the vertical axis indicates intensity (CPS), and the horizontal axis indicates 2θ (°).

Type B crystals of Compound 1 of the present invention obtained in accordance with Preparation Example 10 were measured, and the spectrum shown in FIG. 4 was obtained. For the powder X-ray diffraction spectrum of the type B crystals of Compound 1 of the present invention, characteristic peaks were observed at 2θ s of 14.4°, 15.9°, 17.3°, 22.2° and 22.9°. Peaks were also observed at any or all of 8.6°, 9.8°, 21.2°, 23.6° and 28.4°, and any of these can also be construed at least as characteristic peaks. Furthermore, peaks were also observed at any or all of 12.6°, 18.0°, 18.3°, 18.8°, 19.2°, 19.8°, 20.4°, 25.3°, 26.60 and 31.8°, and any of these can also be construed at least as characteristic peaks.

Test Example 2

Differential Scanning Calorimetry 1 to 3 mg of the crystals obtained in Preparation Examples 7 and 8 of the present specification were each placed in an open aluminum pan, and measurement was performed in a dry nitrogen atmosphere from 50° C. to 220° C. at a heating rate of 10° C./min, using a PYRIS Diamond DSC differential scanning calorimetric measurement apparatus manufactured by Perkin-Elmer. Alternatively, measurement was performed from 50° C. to 220° C. at a heating rate of 10° C./min, using a DSC3200 DSC differential scanning calorimetric measurement apparatus manufactured by Bruker AXS.

The results are as follows.

Figure 2:
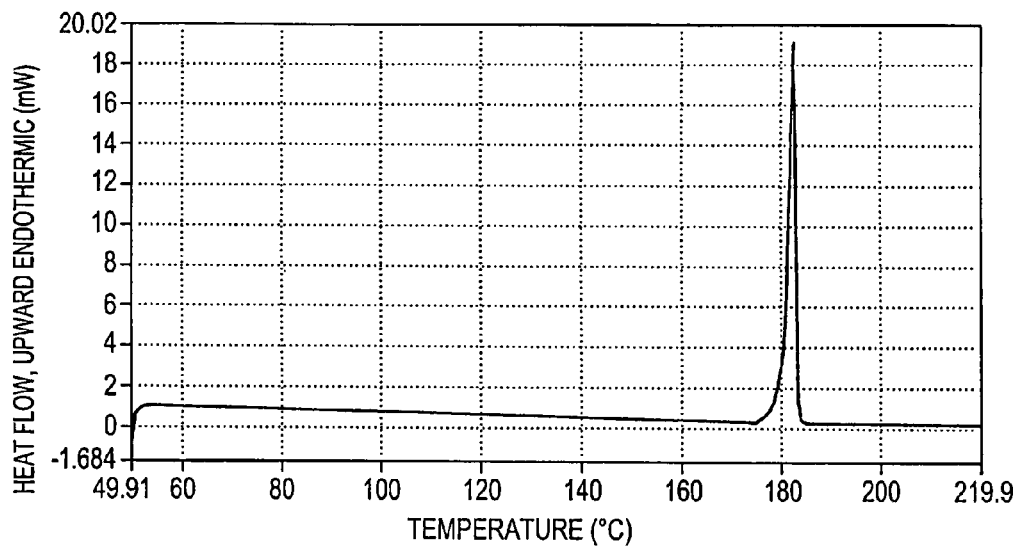
FIG. 2 A figure depicting differential scanning calorimetry of type A crystal of Compound 1 of the present invention. In the figure, the vertical axis indicates mW, and the horizontal axis indicates temperature (° C.).

Measurement was made with the type A crystals of Compound 1 of the present invention obtained in accordance with Preparation Example 7, and as a result, the chart shown in FIG. 2 was obtained. In the differential scanning calorimetric analysis of the type A crystals of Compound 1 of the present invention, an endothermic peak was observed at about 182° C. Additionally, any particular peak suggesting the existence of a hydrate or a solvate was not observed.

Figure 5:
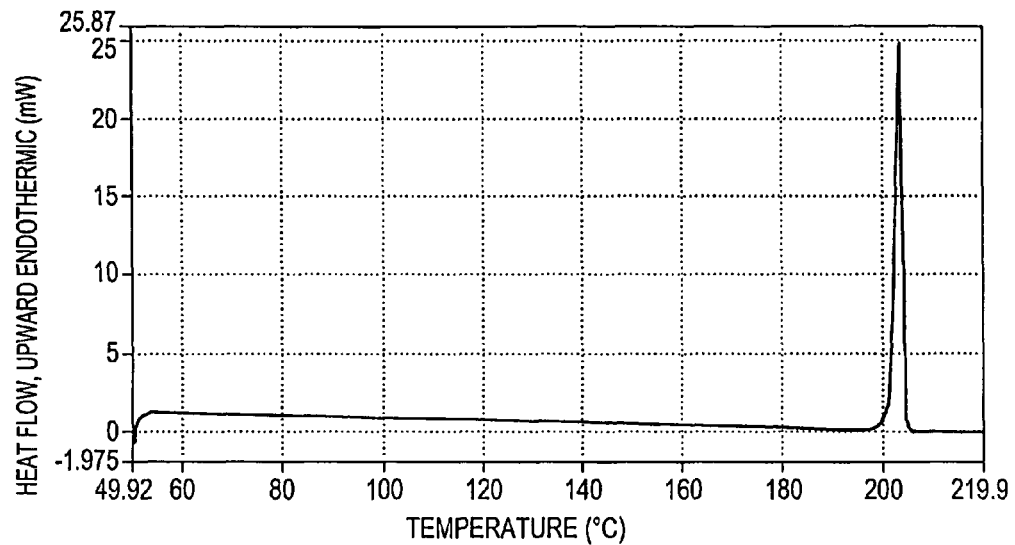
FIG. 5 A figure depicting differential scanning calorimetry of type B crystal of Compound 1 of the present invention. In the figure, the vertical axis indicates mW, and the horizontal axis indicates temperature (C).

Furthermore, measurement was made with the type B crystals of Compound 1 of the present invention obtained in accordance with Preparation Example 8, and as a result, the chart shown in FIG. 5 was obtained. In the differential scanning calorimetric analysis of the type B crystals of Compound 1 of the present invention, an endothermic peak was observed at about 203° C. Additionally, any particular peak suggesting the existence of a hydrate or a solvate was not observed.

According to the present invention, there is no particular problem if the compounds of the present invention are in the form of hydrate or solvate, but it is more preferred that they are anhydrides or non-solvates.

Test Example 3

Infrared Absorption Spectroscopic Analysis

For the crystals obtained in accordance with Preparation Examples 7 and 10 of the present specification, measurement was performed by the potassium bromide disk method.

The results are as follows.

Figure 3:
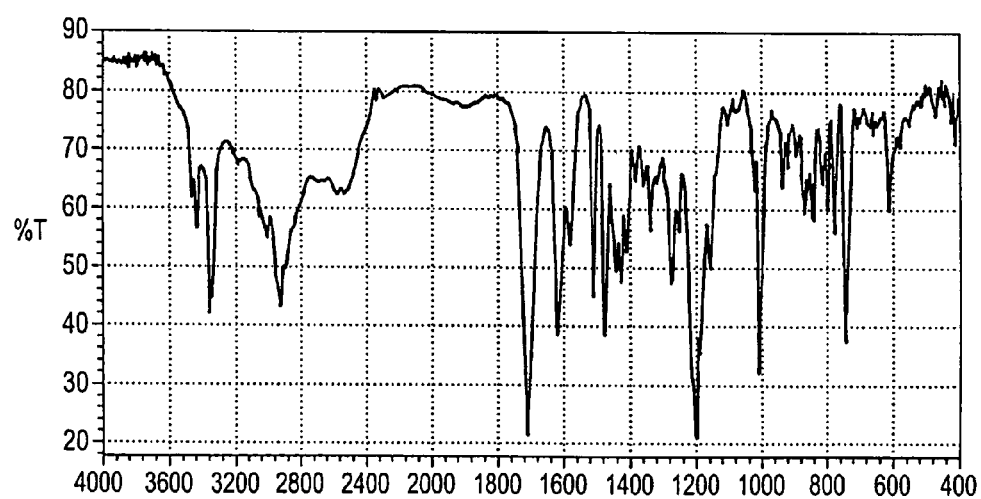
FIG. 3 A figure depicting infrared absorption spectrum of type A crystal of Compound 1 of the present invention. In the figure, the vertical axis indicates transmittance (%), and the horizontal axis indicates $cm^{-1}$.

Measurement was performed for the type A crystals of Compound 1 of the present invention obtained in accordance with Preparation Example 7, and as a result, a spectrum shown in FIG. 3 was obtained. As a result, in the infrared absorption spectrum of the type A crystals of Compound 1 of the present invention, significant infrared absorption bands were observed at wave numbers 3361, 2938, 1712, 1204, 1011 and 746 $cm^{-1}$. Infrared absorption bands were also observed at any or all of 3443, 3349, 1620, 1515, 1480 and 1278 $cm^{-1}$, and any of these can also be construed at least as characteristic peaks. Furthermore, infrared absorption bands were also observed at any or all of 3473, 1585, 1432, 1343, 1159, 781 and 615 $cm^{-1}$, and any of these can also be construed at least as characteristic peaks.

Figure 6:
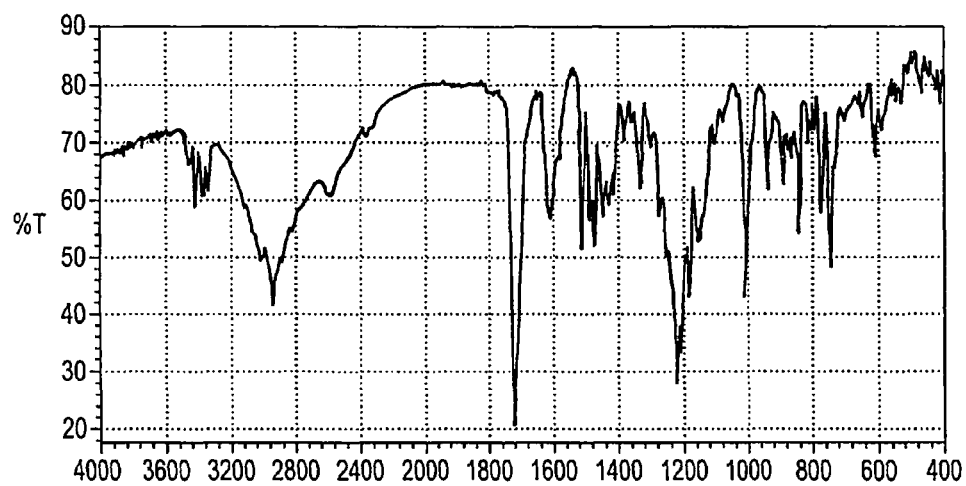
FIG. 6 A figure depicting infrared absorption spectrum of type B crystal of Compound 1 of the present invention. In the figure, the vertical axis indicates transmittance (%), and the horizontal axis indicates $cm^{-1}$.

Further, measurement was performed for the type B crystals of Compound 1 of the present invention obtained by in accordance with Preparation Example 10, and as a result, a spectrum shown in FIG. 6 was obtained. As a result, in the infrared absorption spectrum of the type B crystals, significant infrared absorption bands were observed at wave numbers 2939, 1720, 1224, 1016 and 751 $cm^{-1}$. Infrared absorption bands were also observed at any or all of 3407, 3358, 1513, 1476 and 852 $cm^{-1}$, and any of these can also be construed at least as characteristic peaks. Further, infrared absorption bands were also observed at any or all of 3447, 3325, 1615, 1339, 1157, 945, 783 and 617 $cm^{-1}$, and any of these can also be construed at least as characteristic peaks.

Test Example 4

Scanning Electron Microscope (SEM) Observation

The crystals obtained in Preparation Examples 7 and 8 of the present specification were observed with SEM.

Figure 7:
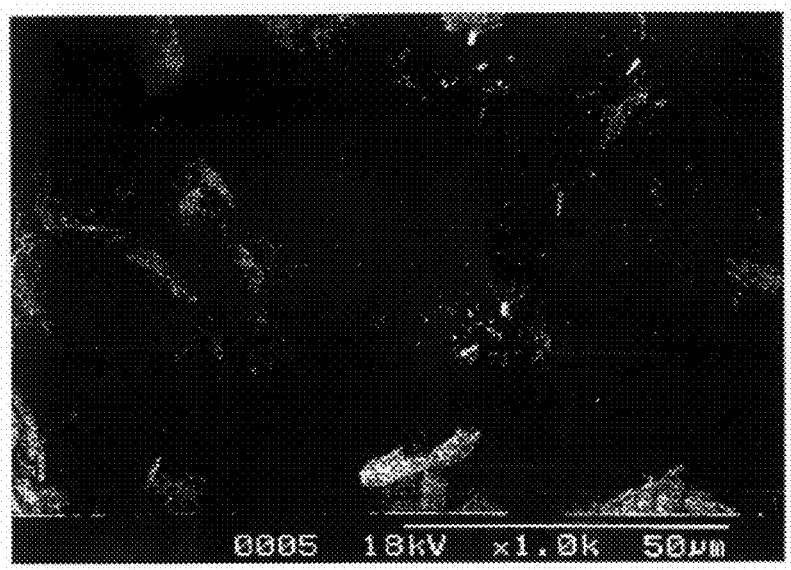
FIG. 7 A scanning electron microphotograph (SEM) showing crystal morphology of type A crystal of Compound 1 of the present invention.

Measurement was made for the type A crystals of Compound 1 of the present invention of Preparation Examples 7, and as a result, a SEM photograph shown in FIG. 7 was obtained.

Figure 8:
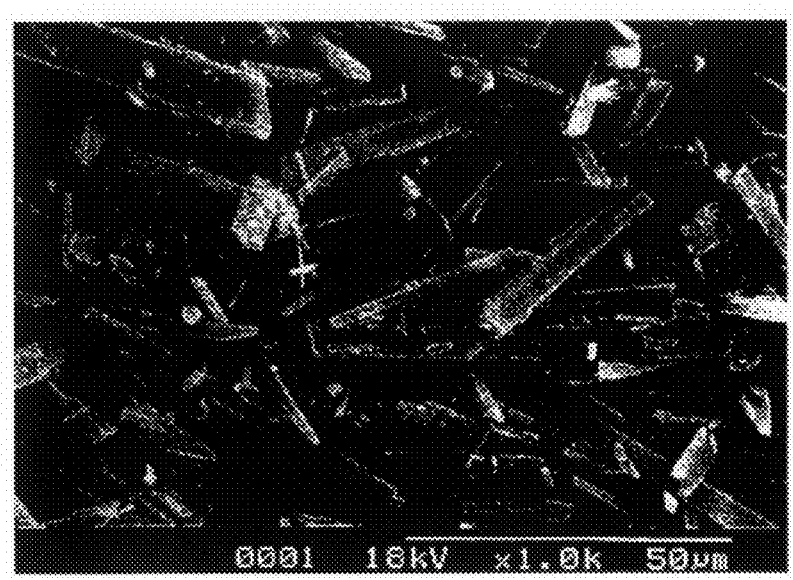
FIG. 8 A scanning electron microphotograph (SEM) showing crystal morphology of type B crystal of Compound 1 of the present invention.

Measurement was made for the type B crystals of Compound 1 of the present invention of Preparation Examples 8, and as a result, a SEM photograph shown in FIG. 8 was obtained.

Nevertheless, these photographs are presented only for referential purposes, and the properties of any of the crystals of the present invention are neither intended to be defined by the electron microscopic images, nor need not be limited thereto.

INDUSTRIAL APPLICABILITY

According to the present invention, a compound useful for therapeutic treatment or prophylactic treatment of inflammatory diseases, autoimmune diseases, allergic diseases, pain, and the like can be provided as a preparation having superior stability.

What is claimed is:

1. A pharmaceutical composition comprising a type A crystal, type B crystal or mixtures thereof of 3-[3-amino-4-(indan-2-yloxy)-5-(1-methyl-1H-indazol-5-yl)phenyl]propionic acid as an active ingredient, together with at least one pharmaceutically acceptable carrier (A) and optionally other pharmaceutically acceptable carrier(s) (B), wherein the at least one pharmaceutically acceptable carrier (A) is selected from the group consisting of crystalline cellulose, mannitol, croscarmellose sodium, corn starch, anhydrous calcium hydrogenphosphate, sucrose, low substituted hydroxypropylcellulose, partially pregelatinized starch, hydroxypropylmethylcellulose, erythritol, polyvinyl alcohol, and carmellose calcium, (a) the composition does not substantially contain, as the pharmaceutically acceptable carrier, a reducing sugar and/or a carrier containing a reducing sugar as an ingredient, or (b) wherein when the pharmaceutically acceptable carrier(s) (B) is a reducing sugar or a carrier containing a reducing sugar as an ingredient, contact of the reducing sugar and said active ingredient is eliminated;

wherein the type A crystal has characteristic peaks at 2θ of 6.9±0.2° 14.4±0.2° 16.4±0.2°, 18.2±0.2°, 25.0±0.2° and 27.5±0.2° in a powder X-ray diffraction spectrum, and wherein the type B crystal has characteristic peaks at 2θ of 14.4±0.2° 15.9±0.2° 17.3±0.2°, 22.2±0.2° and 22.9±0.2° in a powder X-ray diffraction spectrum.

2. The pharmaceutical composition according to claim 1, which does not substantially contain a reducing sugar or a carrier containing a reducing sugar as an ingredient as the pharmaceutically acceptable carrier(s) (B).

3. The pharmaceutical composition according to claim 2, wherein the pharmaceutical composition is a pharmaceutical composition in a dry form.

4. The pharmaceutical composition according to any one of claims 1, 2 and 3 which is in the form of a solid preparation.

* * * * *